(12) United States Patent
Shinohara et al.

(10) Patent No.: US 10,679,394 B2
(45) Date of Patent: Jun. 9, 2020

(54) INFORMATION PROCESSING DEVICE, INFORMATION PROCESSING METHOD, COMPUTER PROGRAM PRODUCT, AND BIOSIGNAL MEASUREMENT SYSTEM

(71) Applicants: Michinari Shinohara, Kanagawa (JP); Hideaki Yamagata, Kanagawa (JP)

(72) Inventors: Michinari Shinohara, Kanagawa (JP); Hideaki Yamagata, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 16/255,892

(22) Filed: Jan. 24, 2019

(65) Prior Publication Data
US 2019/0236824 A1 Aug. 1, 2019

(30) Foreign Application Priority Data

Jan. 30, 2018 (JP) .................................. 2018-014142
Nov. 22, 2018 (JP) .................................. 2018-219725
Dec. 26, 2018 (JP) .................................. 2018-243640

(51) Int. Cl.
*G06T 11/60* (2006.01)
*H04N 13/167* (2018.01)
(Continued)

(52) U.S. Cl.
CPC .......... *G06T 11/60* (2013.01); *A61B 5/04008* (2013.01); *A61B 5/0476* (2013.01);
(Continued)

(58) Field of Classification Search
CPC ... G06T 11/206; G06T 11/60; G06T 2210/41; A61B 5/7425; A61B 5/743; A61B 6/463; A61B 8/463
See application file for complete search history.

(56) References Cited

U.S. PATENT DOCUMENTS

| | | | |
|---|---|---|---|
| 5,213,562 A * | 5/1993 | Monroe | A61B 5/0482 600/28 |
| 2004/0066389 A1* | 4/2004 | Skyba | A61B 8/08 345/619 |

(Continued)

FOREIGN PATENT DOCUMENTS

| | | |
|---|---|---|
| JP | 2009-118910 | 6/2009 |
| JP | 2015-171548 | 10/2015 |

(Continued)

OTHER PUBLICATIONS

U.S. Appl. No. 16/113,501, filed Aug. 27, 2018.

*Primary Examiner* — Jeffery A Brier
(74) *Attorney, Agent, or Firm* — Harness, Dickey & Pierce, P.L.C.

(57) ABSTRACT

An information processing device includes a first display control unit, and a second display control unit. The first display control unit is configured to display, in a display device, a first intensity distribution which is at least per unit time and which is regarding a biosignal coming from a particular source. The second display control unit configured to display, side-by-side in the display device, a first image which has a shape of the source and on which a second intensity distribution of the biosignal corresponding to time corresponding to a point or an area specified in the first intensity distribution is superimposed, and second images which have the shape of the source and on which second intensity distributions of the biosignal before and after the time are superimposed.

21 Claims, 53 Drawing Sheets

(51) Int. Cl.
  *A61B 5/0476* (2006.01)
  *A61B 5/00* (2006.01)
  *A61B 5/04* (2006.01)
  *G06T 11/20* (2006.01)
  *A61B 5/055* (2006.01)

(52) U.S. Cl.
  CPC .......... *A61B 5/7425* (2013.01); *G06T 11/206* (2013.01); *H04N 13/167* (2018.05); *A61B 5/055* (2013.01); *G06T 2200/24* (2013.01); *G06T 2210/41* (2013.01)

(56) References Cited

U.S. PATENT DOCUMENTS

| | | |
|---|---|---|
| 2012/0101398 A1 | 4/2012 | Ramanathan et al. |
| 2013/0109996 A1* | 5/2013 | Turnbull ............ A61B 5/04012 600/544 |
| 2014/0005563 A1 | 1/2014 | Ramanathan et al. |
| 2018/0268588 A1 | 9/2018 | Shinohara et al. |
| 2018/0325483 A1 | 11/2018 | Shinohara et al. |
| 2019/0290185 A1* | 9/2019 | Sarma ................. A61B 5/4094 |

FOREIGN PATENT DOCUMENTS

| | | | |
|---|---|---|---|
| JP | 2018-089336 | 6/2018 | |
| JP | 2018-153612 | 10/2018 | |
| JP | 2018-153614 | 10/2018 | |
| WO | WO-2018089806 A1 * | 5/2018 | ............. A61B 5/00 |
| WO | 2018/100889 A1 | 6/2018 | |
| WO | 2018/168722 A1 | 9/2018 | |
| WO | 2018/168864 A1 | 9/2018 | |

* cited by examiner

FIG.9

Annotation List ▼

☑ Show Markup on wave ——————— 560a

| No. | | File | Time | Event | MEMO | Cluster |
|---|---|---|---|---|---|---|
| 2 ☐ | | 001 | 00:09:30 | 🔥 | normal spike | B |
| 1 ☐ | | 001 | 00:05:00 | 🔥 | strong spike | A |
| 0 ☐ | | 000 | 00:00:00 | 🔥 | Dr.memo | A |

[ COMPLETION OF ANALYSIS ]

560

FIG.20
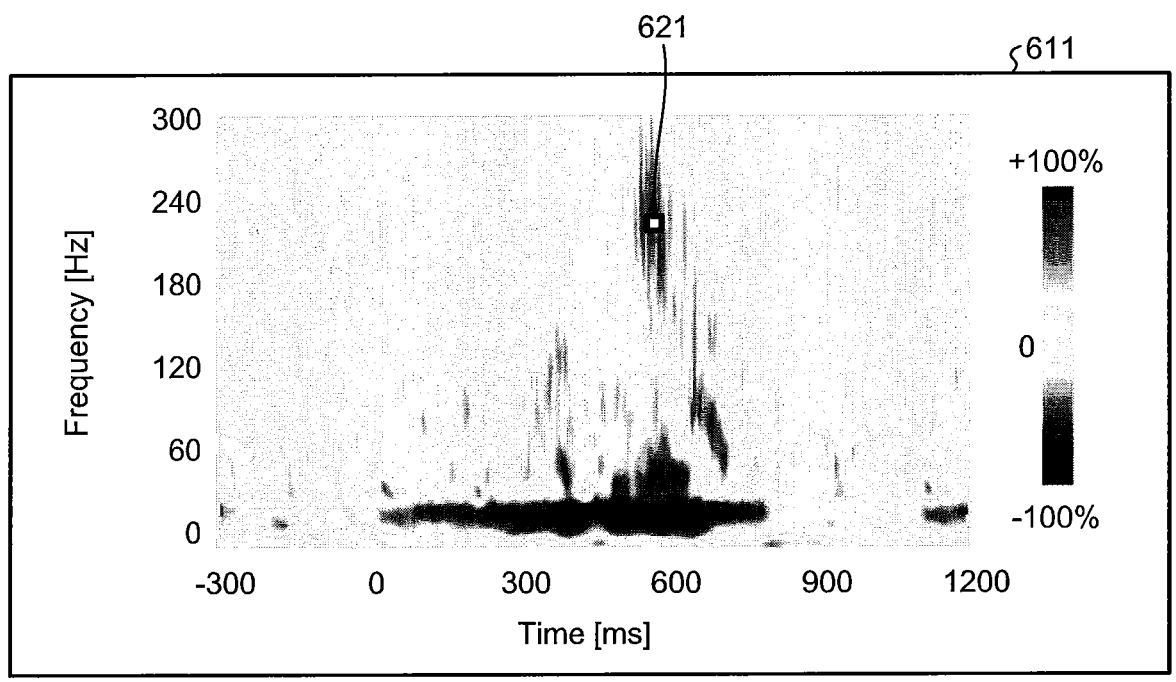
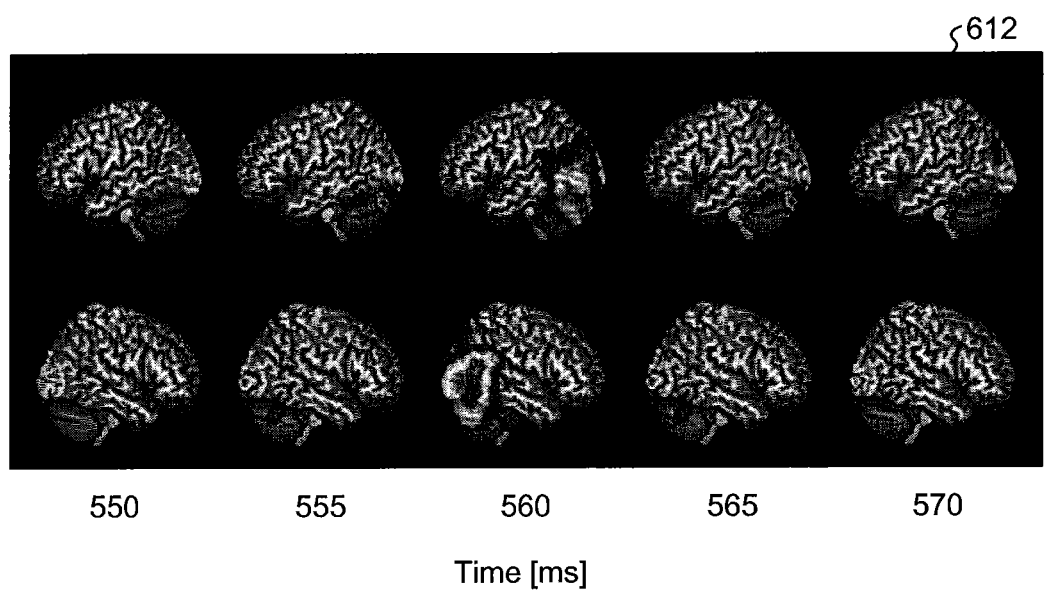

SPEECH AREA

VISUAL AREA

SPEECH AREA +
VISUAL AREA

REVERSAL OF SPEECH
AREA + VISUAL AREA

INFORMATION PROCESSING DEVICE, INFORMATION PROCESSING METHOD, COMPUTER PROGRAM PRODUCT, AND BIOSIGNAL MEASUREMENT SYSTEM

CROSS-REFERENCE TO RELATED APPLICATIONS

The present application claims priority under 35 U.S.C. § 119 to Japanese Patent Application No. 2018-14142, filed on Jan. 30, 2018, Japanese Patent Application No. 2018-219725, filed on Nov. 22, 2018, and Japanese Patent Application No. 2018-243640, filed on Dec. 26, 2018. The contents of which are incorporated herein by reference in their entirety.

BACKGROUND OF THE INVENTION

1. Field of the Invention

The present invention relates to an information processing device, an information processing method, a computer program product, and a biosignal measurement system.

2. Description of the Related Art

In order to perform a brain surgery, it is necessary to identify the target site that represents the site of brain disorder and that is to be excised, and it is necessary to identify the conservation sites that should be conserved without excision. The conservation sites include the visual area, the auditory area, the somatosensory area, the motor area, and the speech area. In case the conservation sites are excised by mistake, it results in the impairment of the senses and the motions of the person. Hence, as far as a brain surgery is concerned, the identification of the target site and the conservation sites is an extremely critical factor. In order to examine in advance the activity of the brain with the aim of performing a brain surgery, the physical phenomena inside the brain are measured using magneto-encephalography, electro-encephalography, fMRI (which stands for functional Magnetic Resonance imaging), or fNIRS (which stands for functional Near-Infrared Spectroscopy). Of those technologies, in fMRI or fNIRS, the blood flow inside the brain is measured and biosignals are obtained. However, judging from the nature of the blood flow, there is restriction on measuring the activity of the brain as far as precision is concerned. On the other hand, in magneto-encephalography or electro-encephalography, the electrical activity of the brain and the magnetic field generated due to the electrical activity can be measured, and biosignals can be measured as waveforms.

As a technology for analyzing the activity of the bran using waveforms obtained as a result of the measurement as described above; a technology has been disclosed in which waveforms are displayed and, in order to enable analysis at the waveform level and in order to make it easier to understand the correspondence between the sensor positions and the waveforms, the display colors of the sensors are varied in a corresponding manner to the display of the waveforms (see Japanese Patent Application Laid-open No. 2009-118910). However, even if the measured biosignals are displayed as waveforms, is not possible to identify the conservation sites inside the brain. In that regard, with the advancement in the technology, a technology disclosed in which, instead of indicating the activity of the brain using waveforms, tree fire position inside the brain (the position of the generation source (the signal source) for generating the biosignals) is identified from the information about the waveforms and is displayed in a superimposed manner on the images indicating the shape of the brain measured using MRI (which stands for Magnetic Resonance Imaging). As a result, the site at which the biosignals are generated in the brain becomes strikingly obvious, thereby making the clinical examination easier. Herein, the fire implies that the neurons in the brain perform activity getting stimulated by other neurons.

As the next the attention is currently focused on the manner in which the signal source identified inside the brain moves around. In order to check the manner in which the signal source identified inside the brain moves around, videos have been often used till now.

However, if a video is used to check the manner in which the signal source identified inside the brain moves around, not only it is hard to understand the time of the most intense fire (the time of the most intense generation of biosignals), but it is also difficult to compare the state of the fire with the fire at earlier and later times. Moreover, when a video is used alone, although it is easier to get an intuitive understanding, it is illustrated for performing a detailed analysis with many people during a conference.

SUMMARY OF THE INVENTION

An information processing device includes a first display control unit, and a second display control unit. The first display control unit is configured to display, in a display device, a first intensity distribution which is at least per unit time and which is regarding a biosignal coming from a particular source. The second display control unit configured to display, side-by-side in the display device, a first image which has a shape of the source and on which a second intensity distribution of the biosignal corresponding to time corresponding to a point or an area specified in the first intensity distribution is superimposed, and second images which have the shape of the source and on which second intensity distributions of the biosignal before and after the time are superimposed.

BRIEF DESCRIPTION OF THE DRAWINGS

FIG. 9 is a diagram of the updated annotation list;

FIG. 20 is a diagram illustrating an example of the state in which the state of the brain corresponding to the specified position in the heat map is displayed in the center of the stereogram;

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
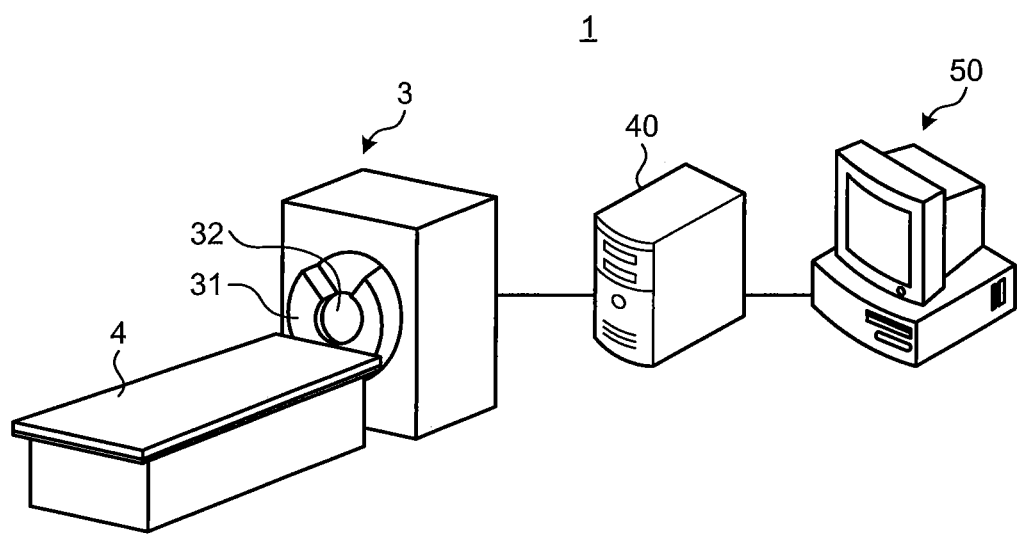
FIG. 1 is a diagrammatic illustration of a biosignal measurement system according to an embodiment.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An embodiment has an object to provide an information processing device, an information processing method, a computer program product, and a biosignal measurement system that enable displaying still images, which indicate the activity of the brain, in a frame-by-frame advancing manner or a frame-by-frame rewinding manner, thereby making it easier to analyze the activity of the brain.

An exemplary embodiment of an information processing device, an information processing method, a computer program product, and a biosignal measurement system is described below in detail with reference to the accompanying drawings. Herein, although the invention is described with reference to the embodiment described below for a complete and clear disclosure, the appended claims are not to be thus limited but are to be construed as embodying all modifications and alternative constructions that may occur to one skilled in the art that fairly fall within the basic teaching herein set forth.

(Overview of Biosignal Measurement System)

FIG. 1 is a diagrammatic illustration of the biosignal measurement system according to the embodiment. Thus, explained below with reference to FIG. 1 the overview of a biosignal measurement system 1 according to the embodiment.

The biosignal measurement system 1 measures a plurality of types of biosignals (for example, MEG signals (MEG stands for magneto-encephalography) and EEG signals (EEG stands for electro-encephalography)) of the subject being tested, and displays the biosignals.

The target biosignals for measurement are not limited to magneto-encephalography signals or electro-encephalography signals. Alternatively, for example, electrical signals generated due to the activity of the heart (electrical signals expressible as an electrocardiogram) can also be treated as the target biosignals for measurement. As illustrated in FIG. 1, the biosignal measurement system 1 includes a measurement device 3 that measures one or more types of biosignals of the subject being tested; a server 40 that records therein one or more types of biosignals measured by the measurement device 3; and an information processing device 50 that analyzes one or more types of biosignals recorded in the server 40. Meanwhile, in FIG. 1, the server 40 and the information processing device 50 are illustrated to be different devices. Alternatively, for example, at least some of the functions of the server 40 can be incorporated in the information processing device 50.

In the example illustrated in FIG. 1, the subject being tested (the subject being measured) lies down on a measurement table 4 with electrodes (or sensors) for electro-encephalography attached to his or her head region, and then puts the head region in a recessed portion 32 of a dewar 31 of the measurement device 3. The dewar 31 is a holder made of liquid helium and having a cryogenic environment. On the inside of the recessed portion 32 of the dewar 31, a number of magnetic sensors meant for electro-encephalography are installed. The measurement device 3 collects electro-encephalography signals from the electrodes, collects magneto-encephalography signals from the magnetic sensors, and outputs data containing the electro-encephalography and the magneto-encephalography signals (hereinafter, called "measurement data") to the server 40. The measurement data output to the server 40 is read and displayed in the information processing device 50 for analysis purposes. Generally, the dewar 31, which has built-in magnetic sensors, and the measurement table 4 are installed inside a magnetic shield room. However, in FIG. 1, as a matter of convenience, the magnetic shield room is not illustrated.

The information processing device 50 displays waveforms of the magneto-encephalography signals, which are obtained from a plurality of magnetic sensors, and waveforms of the electro-encephalography signals, which are obtained from a plurality of electrodes, in a synchronized manner on the same time axis. The electro-encephalography signals are signals in which the electrical activity of the nerve cells (the flow of ionic charge generated due to the dendritic outgrowth of neurons at the time of synapse transmission) is expressed as voltage values among the electrodes. The magneto-encephalography signals are signals that represent the minute fluctuation in electrical fields that is attributed to the electrical activity of the brain. The cerebral magnetic field is detected by a high-sensitivity SQUID sensor (SQUID stands for Superconducting Quantum Interference Device). Herein, the electro-encephalography signals and the magneto-encephalography signals are examples of "biosignals".

(Hardware Configuration of Information Processing Device)

Figure 2:
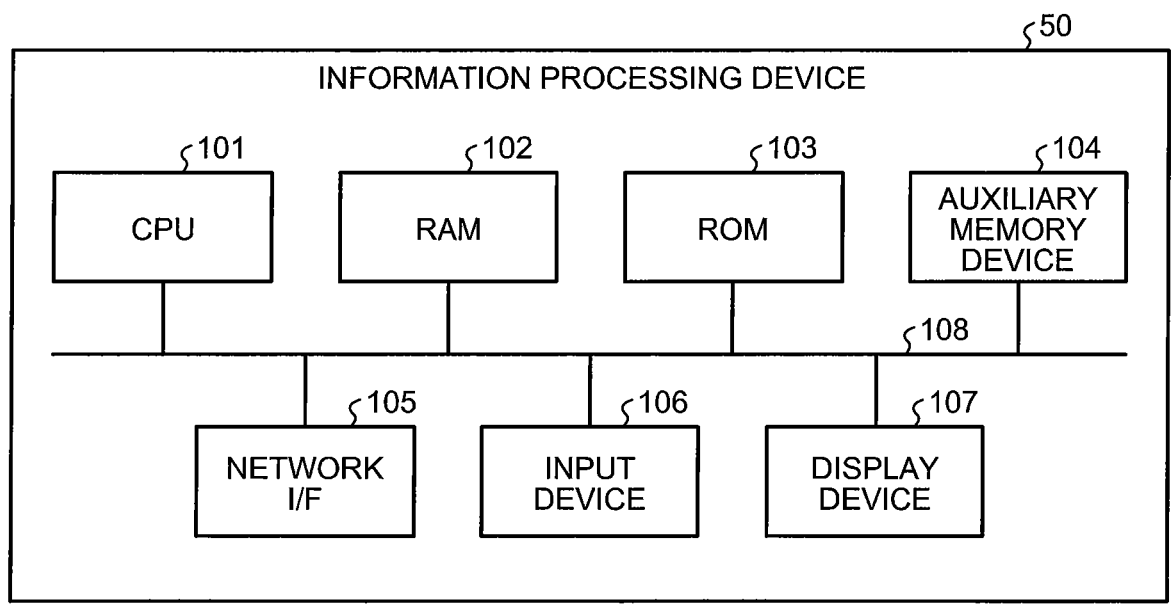
FIG. 2 is a diagram illustrating an exemplary hardware configuration of an information processing device according to the embodiment.

FIG. 2 is a diagram illustrating an exemplary hardware configuration of the information processing device according to the embodiment. Thus, explained with reference to FIG. 2 is a hardware configuration of the information processing device 50 according to the embodiment.

As illustrated in FIG. 2, the information processing device 50 includes a central processing unit (CPU) 101, a random access memory (RAM) 102, a read only memory (ROM) 103, an auxiliary memory device 104, a network interface (I/F) 105, an input device 106, and a display device 107. Moreover, these constituent elements are connected to each other by a bus 108.

The CPU 101 is an arithmetic device that controls the overall operations of the information processing device 50 and performs a variety of information processing. The CPU 101 executes an information display program stored in the ROM 103 or the auxiliary memory device 104, and controls the display operation for displaying a measurement/collection screen and an analysis screen (such as a time-frequency analysis screen).

The RAM 102 is a volatile memory device that is used as the work area of the CPU 101, and that is used to store major control parameters and information. The ROM 103 is a nonvolatile memory device that is used to store basic t-output programs. For example, the information display program can be stored in the ROM 103.

The auxiliary memory device 104 is a memory device such as a hard disk drive (HDD) or a solid state drive (SSD). For example, the auxiliary memory device 104 is used to store control programs meant for controlling the operations of the information processing device 50, and to store a variety data and files necessary for the operations of the information processing device 50.

The network I/F 105 is a communication interface t at enables communication with devices, such as the server 40, installed in the network. For example, the network I/F 105 is implemented using a TCP/IP-compatible NIC (NIC stands for Network Interface Card, and TCP/IP stands for Transmission Control Protocol/Internet Protocol).

The input device 106 is a user interface such as the input function of a touch-sensitive panel, a keyboard, a mouse, or operation buttons. The display device 107 is a display device for displaying a variety of information. For example, the display device 107 is implemented using the display function of a touch-sensitive panel, or liquid crystal display (LCD), or an organic electroluminescence (EL) display. The display device 107 is used to display the measurement/collection screen and the analysis screen, and the screens are updated according to the input-output operations performed via the input device 106.

Meanwhile, the hardware configuration of the information processing device 50 as illustrated in FIG. 2 is only exemplary, and the information processing device 50 can include other devices. Moreover, for example, the information processing device 50 illustrated in FIG. 2 has a hardware configuration under the assumption that a personal computer is used. However, that is not the only possible case. Alternatively, a mobile terminal such as a tablet can also be used as the information processing device 50. In that case, the network I/F 105 can be a communication interface having the wireless communication function.

(Functional Block Configuration of Information Processing Device)

Figure 3:
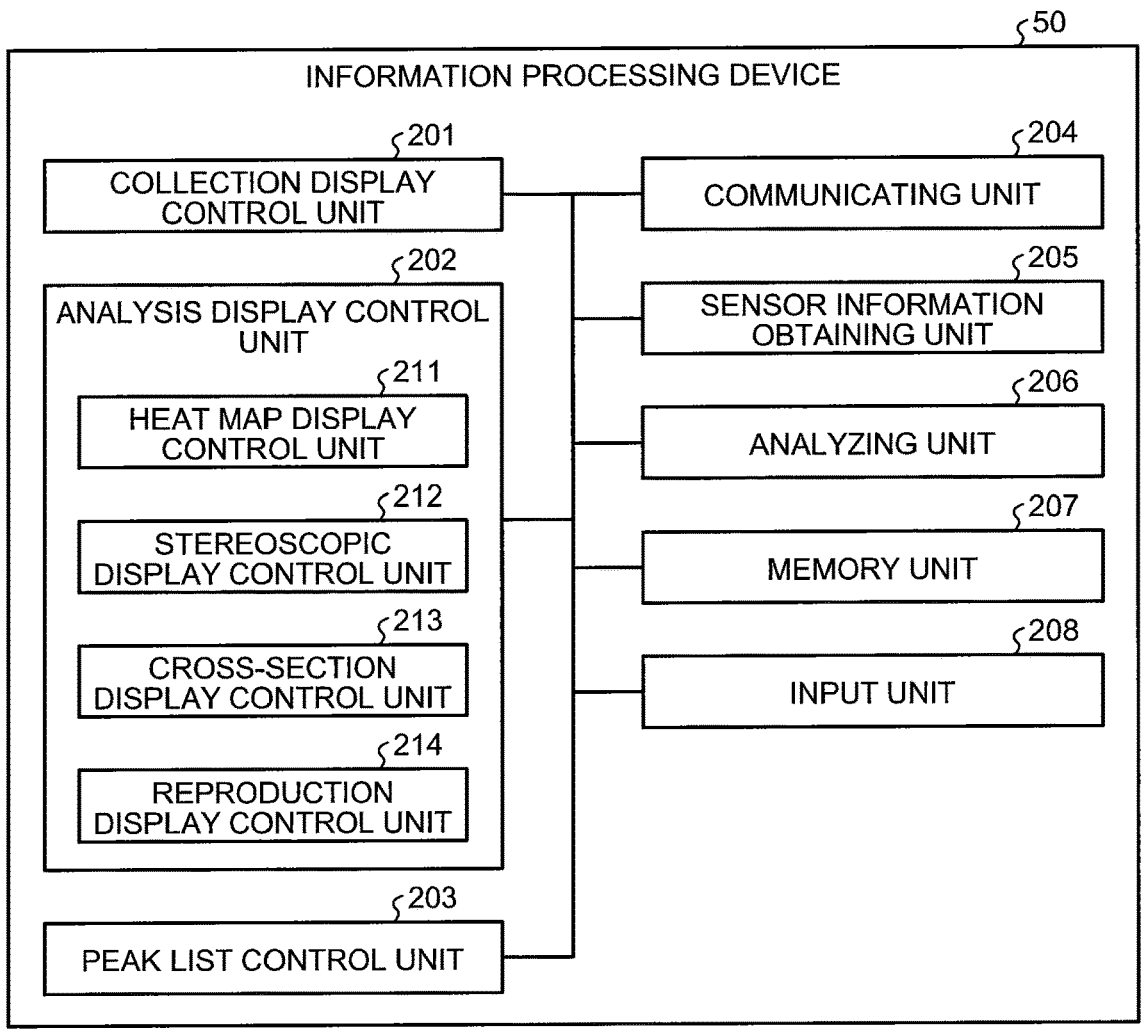
FIG. 3 is a diagram illustrating an exemplary functional block configuration of the information processing device according to the embodiment.

FIG. 3 is a diagram illustrating an exemplary functional block configuration of the information processing device according to the embodiment. Thus, explained with reference to FIG. 3 is a functional block configuration of the information processing device 50 according to the embodiment.

As illustrated in FIG. 3, the inform on processing device 50 includes a collection display control unit 201, an analysis display control unit 202, a peak list control unit 203 (a peak control unit), communicating unit 204, sensor information obtaining unit an analyzing unit 206 (a calculating unit) a memory unit 207, and an input unit 208.

The collection display control unit 201 is a functional unit that controls, according to a method explained later with reference to FIGS. 5 to 10, the screen display during an operation for collecting sensor information.

The analysis display control unit 202 is a functional unit that controls, according to a method described later with reference to FIGS. 11 to 59, the screen display of the signal intensities of the biosignals as calculated by ale analyzing unit 206 from sensor information (electro-encephalography signals or magneto-encephalography signals) obtained by the sensor information obtaining unit 205. As illustrated in FIG. 3, the analysis display control unit 202 includes a heat map display control unit 211 (a first display control unit), a stereoscopic display control unit 212 (a second display control unit), a cross-section display control unit 213 (a third display control unit), and a reproduction display control unit 214.

The heat map display control unit 211 functional unit that controls the screen display of a heat map 611 in a time-frequency analysis screen 601 described later with reference to FIG. 11. The stereoscopic display control unit 212 is a functional unit that controls the screen display of a stereogram 612 in the time-frequency analysis screen 601. The cross-section display control unit 213 is a functional unit that controls the screen display or a head region trihedral figure 613 in the time-frequency analysis screen 601. The reproduction display control unit 214 is a functional unit that controls the reproduction and display according to an operation input performed with respect to a reproduction control panel 615 in the time-frequency analysis screen 601.

The peak list control unit 203 is a functional unit that extracts peaks of the signal intensities satisfying the set conditions, and registers the peaks in a peak list 614 in the time-frequency analysis screen 601 described later with reference to FIG. 11.

The communicating unit 204 is a functional unit that performs data communication with the measurement device 3 or the server 40. The communicating unit 204 is implemented using the network I/F 105 illustrated in FIG. 2.

The sensor information obtaining unit 205 is a functional unit that obtains sensor information (electro-encephalography signals or magneto-encephalography signals) via the communicating unit 204. The analyzing unit 206 analyzes the sensor information (the measured signals) obtained from the sensor information obtaining unit 205, and calculates signals indicating the signal intensities in each region of the brain (hereinafter, such signals too are sometimes called "biosignals").

The memory unit 207 is a functional unit that is used to store the data of biosignals that indicate the signal intensities calculated by the analyzing unit 206. The memory unit 207 is implemented using the RAM 102 or the auxiliary memory device 104 illustrated in FIG. 2.

The input unit 208 is a functional unit that receives input operations regarding annotation information attached to the sensor information, and receives a variety input operations with respect to the time-frequency analysis screen 601. The input unit 208 is implemented using the input device 106 illustrated in FIG. 2.

The collection display control unit 201, the analysis display control unit 202, the peak list control unit 203, the sensor information obtaining unit 205, and the analyzing unit 206 are implemented when the CPU 101 reads a computer program from one ROM 103, loads in the RAM 102, and executes it. Alternatively, instead of using a computer program representing software, some or all of the collection display control unit 201, the analysis display control unit 202, the peak list control unit 203, the sensor information obtaining unit 205, and the analyzing unit 206 can be implemented using hardware circuitry such as an application specific integrated circuit (ASIC) or a field-programmable gate array (FPGA).

Meanwhile, the functional units illustrated in FIG. 3 are meant to illustrate the functions in a conceptual manner, and the configuration is not limited to the configuration illustrated in FIG. 3. Alternatively, for example, the functional units that are illustrated as independent functional units in FIG. 3 can be configured as a single functional unit. In contrast, the functions of a single functional unit illustrated in FIG. 3 can be divided into a plurality of functions, and thus the functional unit can be configured as a plurality of functional units.

(Operations in Start Screen)

Figure 4:
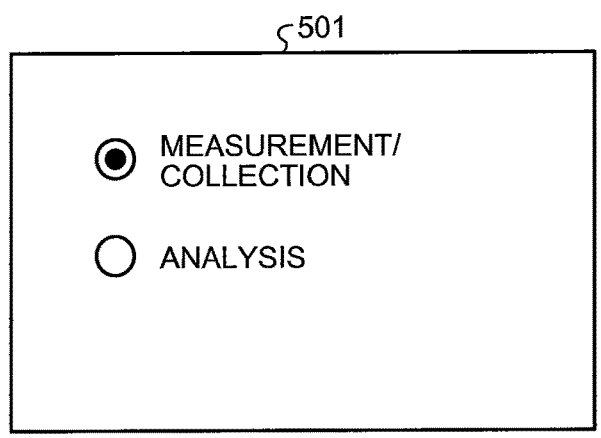
FIG. 4 is a diagram illustrating an example of a start screen displayed in the information processing device according to the embodiment.

FIG. 4 is a diagram illustrating an example of a start screen displayed in the information processing device according to the embodiment. Thus, explained below with FIG. 4 are the operations performed in a start screen 501.

In the start screen 501, a "measurement/collection" selection button and an "analysis" selection button are displayed. In the case of performing magneto-encephalography measurement and electro-encephalography measurement, data measurement/collection and data analysis is often performed using separate constituent elements. For example, when the measurement engineer (the person in charge of measurement) selects the "measurement/collection" selection button, the data measured in the measurement device 3 gets sequentially stored in the server 40, and is read and displayed in the information processing device 50. After the end of measurement/collection, when a doctor selects the "analysis" selection button, the collected measurement data is read and analyzed.

(Operation During Measurement/Collection)

Figure 5:
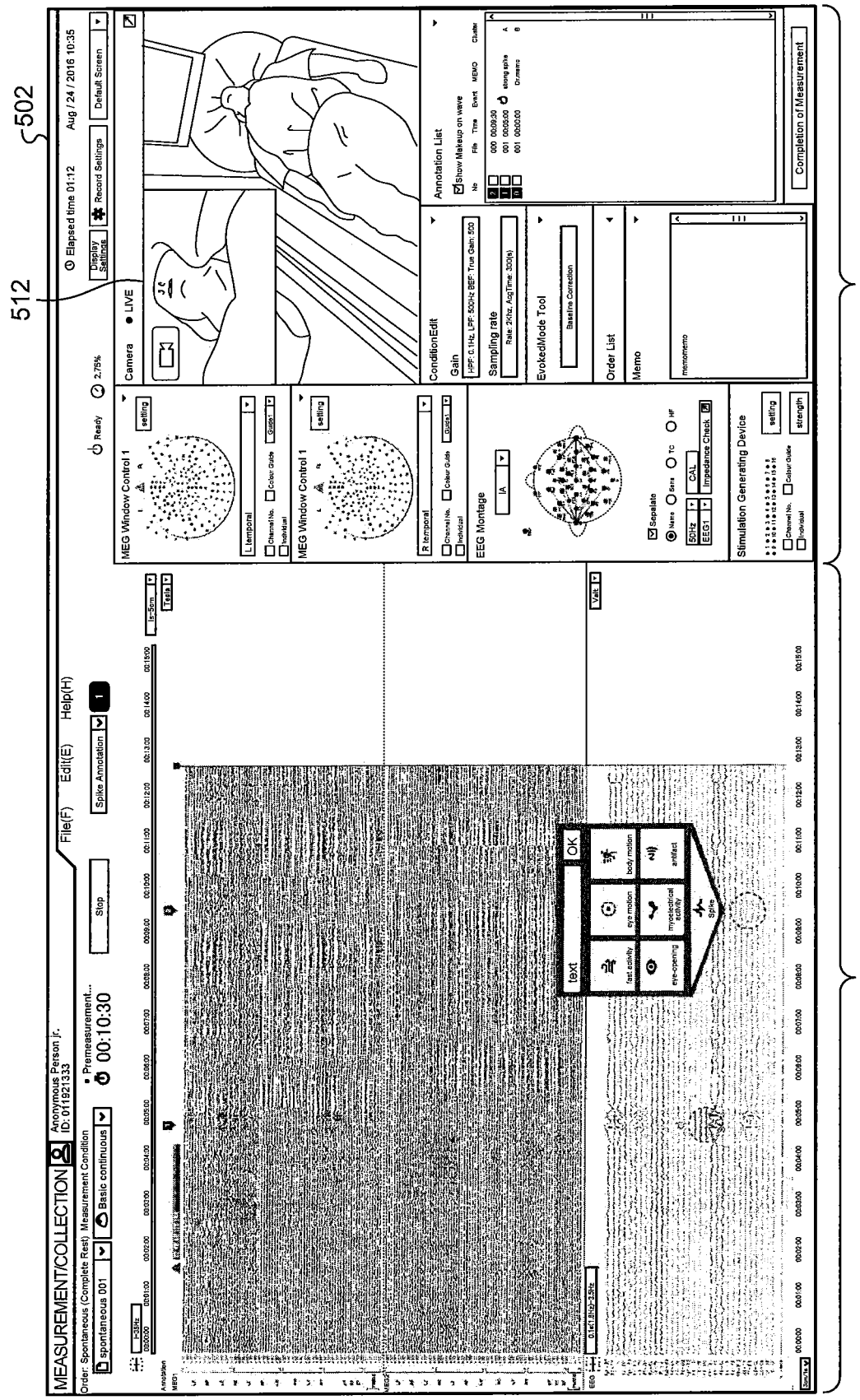
FIG. 5 is a diagram illustrating an example of a measurement/collection screen.

FIG. 5 is a diagram illustrating an example of the measurement/collection screen. As illustrated in FIG. 5, measurement/collection screen 502 includes an area 511a for displaying the signal waveforms of the measured biosignals (herein, magneto-encephalography signals and electro-encephalography signals), and includes an area 511b for displaying monitoring information other than the signal waveforms. The area 511a for displaying the signal waveforms is positioned on the left-hand side of the screen when viewed by the person in charge of measurement, and the area 511b for displaying monitoring information other than the signal waveforms is positioned on the right-hand side of the screen when viewed by the person in charge of measurement. As a result, the eye movement of the person in charge of measurement in accordance with the movement of the waveforms that are detected and displayed in real time (from the left-hand side toward the right-hand side) is economical, and the movement of the mouse from the area 511a on the left-hand side of the screen to the area 511b on the right-hand side of the screen is also economical; thereby enabling achieving enhancement in the work efficiency.

In the area 511b of the display screen, a monitoring window 512 is displayed to enable confirmation of the condition of the subject being measured. As a result of displaying the live footage of the subject being measured; as described later, it becomes possible to achieve enhancement in checking the signal waveforms and in the reliability of the assessment. In FIG. 5, it is illustrated that the entire measurement/collection screen 502 is displayed on the display screen single monitor display (the display device 107). However, alternatively, the left-side area 511a and the right-side area 511b can be separately displayed in two or more monitor displays.

Figure 6:
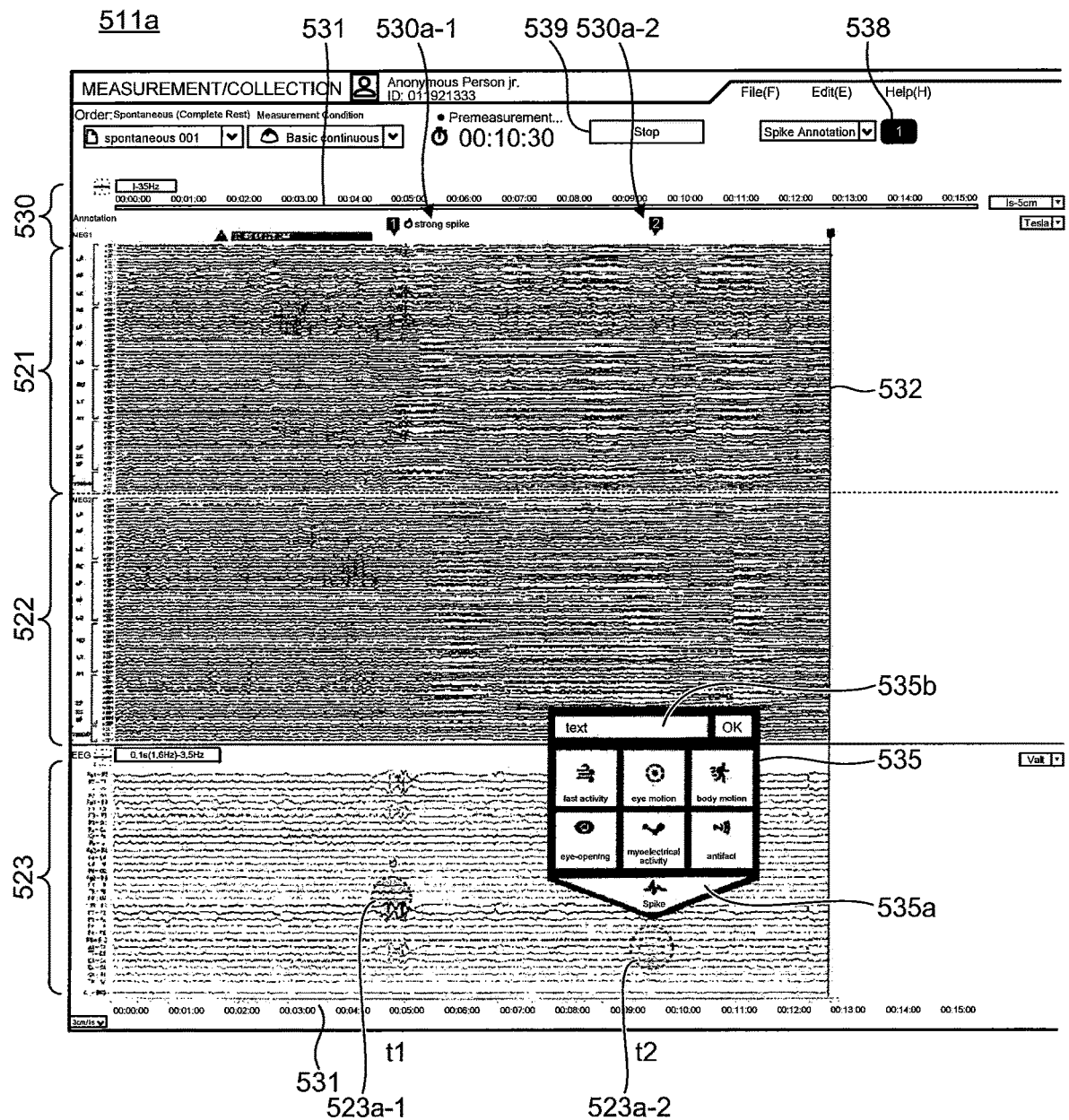
FIG. 6 is an enlarged view of the left-side area of the measurement/collection screen.

FIG. 6 is an enlarged view of the left side area of the measurement/collection screen. The area 511a includes a first display area 530 for displaying time information of signal detection in the horizontal direction (a first direction) of the screen; and includes second display areas 521 to 523 for displaying, in parallel, a plurality of signal waveforms based on signal detection in the vertical direction (a second direction) of the screen.

In the example illustrated in FIG. 6, the time information displayed in the first display area 530 represents a timeline including the display of time along a time axis 531. Alternatively, only a strip shaped axis can be displayed without displaying the time (in numbers); or only the time (in numbers) can be displayed without displaying the axis. Moreover, instead of displaying the time axis 531 in the first display area 530 positioned on the upper side of the screen, the time axis 531 can be displayed on the lower side of the second display area 523, and the timeline can be displayed.

In the area 511a, a plurality of signal waveforms obtained from a plurality of sensors of the same type or the signal waveforms of a plurality of types of signals obtained from a plurality of types of sensor groups are displayed in a synchronized manner on the same time axis 531. In the example illustrated in FIG. 6, the waveforms of a plurality of magneto-encephalography signals obtained from the right-hand side of the head region of the subject being measured are displayed in parallel in the second display area 521, and the waveforms of a plurality of magneto-encephalography signals obtained from the left-hand side of the head region of the subject being measured are displayed in parallel in the second display area 522. The waveforms of a plurality of electro encephalography signals are displayed in parallel in the second display area 523. The waveforms of a plurality of electro-encephalography signals represent voltage signals measured among the electrodes. Each signal waveform is displayed after being associated with the identification number or the channel number of the sensor that obtained the concerned signal.

After the measurement is started and the measurement information is collected from each sensor, the signal waveforms get displayed from the extreme left toward the extreme right in each of the second display areas 521 to 523 of the area 511a as time advances. A line 532 indicates the time of measurement (current time), and moves from the left-hand side toward the right-hand side of the screen. Once the signal waveforms are displayed to the extreme right of the area 511a (i.e., the extreme right of the time axis 531), the signal waveforms gradually disappear from the extreme left of the screen toward the right-hand side, and new signal waveforms are sequentially displayed from the left-hand side toward the right-hand side at the positions from which the earlier signal waveforms had disappeared. Moreover, the line 532 also moves from the extreme left toward the right-hand side. Along with that, also in the first display area 530 extending in the horizontal direction, the advancement of time is displayed on the time axis 531 in accordance with the advancement of the measurement. Such measurement/collection is carried on until an end button 539 is pressed.

It is a feature of the embodiment that, when the person in charge of measurement (the person in charge of collection) observes any waveform disturbance in the signal waveforms during data collection or observes any difference in the amplitude, he or she can mark the point of interest or the range of interest on the signal waveforms. The point to be marked or the range to be marked can be specified by a pointer operation or a clicking operation of the mouse. The specified point or the specified range gets highlighted on the signal waveforms in the second display areas 521 to 523, and is displayed along the time axis 531 of the first display area 530 at the time position or over the time range corresponding to the specification result. The marking information containing the display on the time axis 531 is stored along with signal waveform data. A specified point corresponds to a particular time, and a specified range corresponds to a certain range including a particular time.

In the example illustrated in FIG. 6, at a time t1, a range including one or more channels is specified in the second display area 523, and a time period including the time t1 is highlighted at a marking 523a-1. In connection with the display of the marking 523a-1, an annotation 530a-1 indicating the specification result is displayed at the corresponding time position in the first display area 530. At a time t2, a different waveform position or the vicinity of that different waveform position is marked in the second display area 523, and a marking 523a-2 is highlighted at that position (the time t2) or in the surrounding area (at least either a time range is specified or a plurality of waveforms is specified). At the same time, an annotation 530a-2 is displayed at the corresponding time position (the time range) in the first display area 530. Herein, an annotation implies adding related information to particular data as an explanatory note. In the embodiment, an annotation is displayed as an explanatory note based on at least the specified time information, and is displayed as an explanatory note in a corresponding manner to the display position of the waveforms based on at least the time information. In the case of displaying a plurality of channels, an annotation can be displayed as an explanatory note in a corresponding manner to the concerned channel information.

As an example, the annotation 530a-1, which is added in the first display area 530 at the time t1 includes an annotation identification number and information indicating the attribute of the waveforms. In this example, an annotation number "1" is displayed along with an icon indicating the attribute of the waveforms and along with text information "strong spike".

At the time t2, when the person in charge of measurement specifies a different waveform position or the surrounding area, the marking 523a-2 gets highlighted at the specified point; and an annotation number "2" gets displayed at the corresponding time position in the first display area 530. Moreover, at the highlighted point, a popup window 535 is displayed for enabling attribute selection. The popup window 535 includes selection buttons 535a for selecting various attributes and includes an input box 535b for inputting comments and additional information. The selection buttons 535a include waveform attributes such as "fast activity", "eye motion", "body motion", and "spike" that indicate the cause for waveform disturbance. Since the condition of the subject being measured can be checked in the monitoring window 512 of the area 511b of the screen, the person in charge of measurement can appropriately select the attribute indicating the cause for waveform disturbance. For example, when there is a spike in the waveform, it can be determined whether the spike indicates the medical condition of epilepsy or whether the spike is attributed to a body motion (such as sneezing) of the subject being measured.

The same operation is performed at the time t1 too. With reference to FIG. 6, the selection button 535a indicating "spike" is selected in the popup window 535, and the annotation 530a-1 is displayed in the first display area 530 in response to the input of "strong spike" in the input box 535b. Due to such a display form, when a plurality of signal waveforms is displayed in a synchronized manner on the same time axis 531, not only the point of interest or the range of interest of the signal waveforms can be easily identified by visual confirmation, but the basic information of the point of interest can also be easily understood.

Meanwhile, alternatively, either some part or all of the annotation 530a-1, such as at least either the attribute icon or the text information, can be displayed also near the marking 523a-1 that is done on the signal waveforms in the second display area 523. However, the addition of an annotation on the signal waveforms may sometimes hamper the checking of the waveform shape. Hence, in the case of displaying annotations on the signal waveforms in the second display areas 521 to 523, it is desire to enable selection of whether to display or hide the annotations.

A counter box 538 displays the cumulative number of annotations corresponding to the spikes. Every time the "spike" is selected, the counter value in the counter box 538 is incremented, so that the total number of spikes from the start of recording up to the current time (the line 532) can be understood in one glance.

Figure 7:
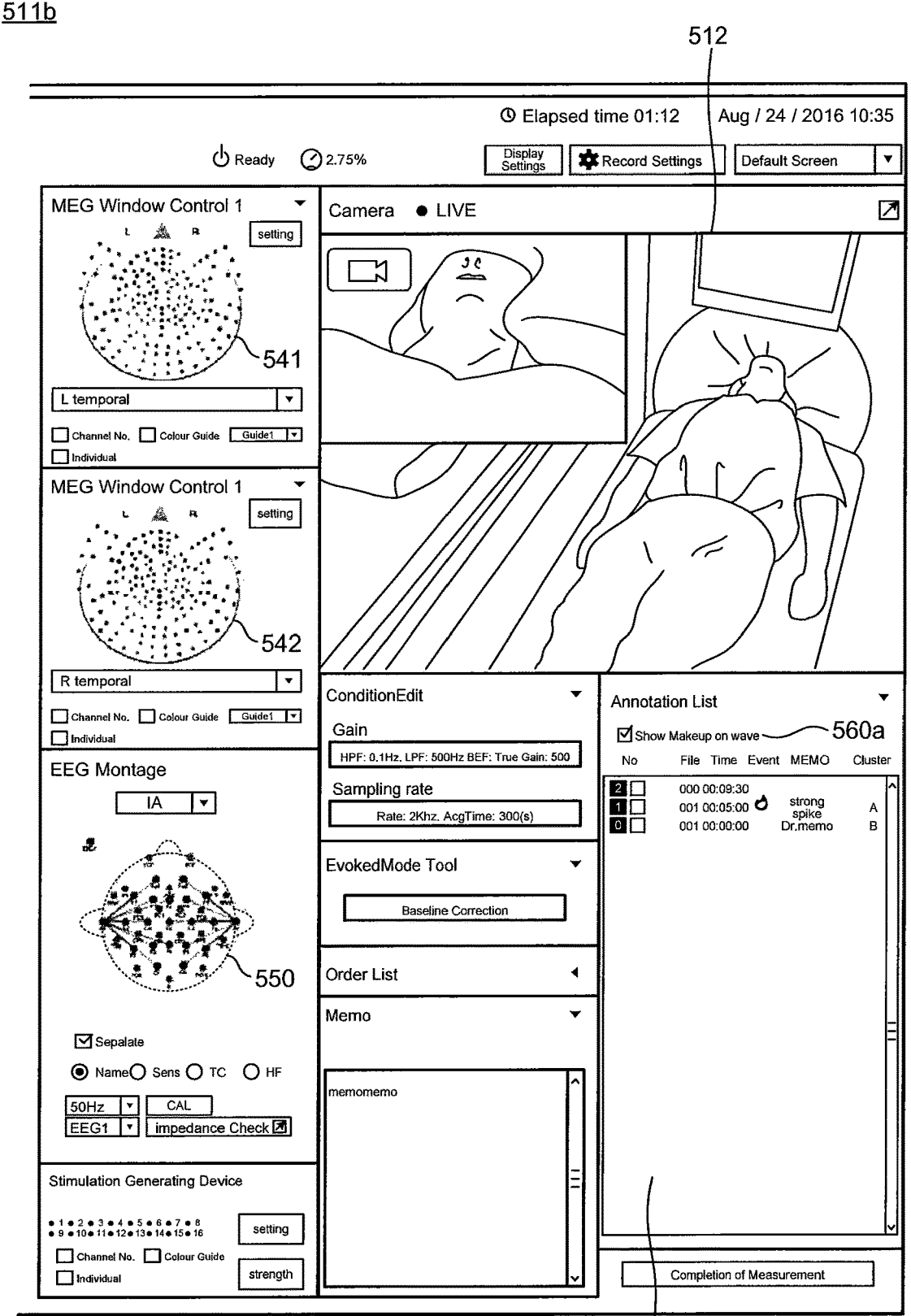
FIG. 7 is an enlarged view of the right-side area or the measurement/collection screen.

FIG. 7 is an enlarged view of the right-side area of the measurement/collection screen. In FIG. 7 is illustrated the state at the same time (the same point of time on the line 532) as in FIG. 6. In the monitoring window 512 of the area 511b is displayed the live footage of the subject being measured who is lying down on the measurement table 4 with the head region put inside the measurement device 3. In the area 511b, magneto-encephalography distribution charts 541 and 542, an electro-encephalography chart 550, and an annotation list 560 are displayed that correspond to the signal waveforms in the second display areas 521 to 523. The annotation list 560 is a list of annotations marked on the signal waveforms illustrated in FIG. 6. Every time a position or a range is specified on the signal waveforms in one of the second display areas 521 to 523 and every time an annotation is attached, the corresponding information is added to the annotation list 560. In the measurement/collection screen 502, the addition and display of annotations in the annotation list 560 is performed, for example, in descending order (by displaying new data on top). However, that is not the only possible case. That is, there is no issue in displaying the annotation list in ascending order as long as it is possible to understand the correspondence relationship with the annotations displayed along with the time axis 531 in the first display area 530. Moreover, not only the display sequence can be varied, but sorting can also be done on an item-by-item basis.

In the example illustrated in FIG. 7, in the annotation list 560, time information corresponding to the annotation number "1" is written along with the attached annotation information. As the annotation information, the attribute information indicating a "spike" and the text "strong spike" are recorded. Moreover, at the point of time at which the marking 523a-1 is highlighted, the time information corresponding to the annotation number "2" is written. Herein, an "annotation" may be a set including an annotation number, time information, and annotation information; or may include only annotation information; or may be a set including annotation information and either an annotation number or time information.

In the vicinity of the annotation list 560, a selection box 560a is placed for enabling display/hide selection. When the option of hiding is selected in the selection box 560a, annotations other than the highlighted markings on the signal waveform are hidden, but the annotations along the time axis 531 of the first display area 530 are displayed on a continuing basis. As a result, the annotation information is made recognizable without blocking the visibility of the signal waveforms.

Figure 8:
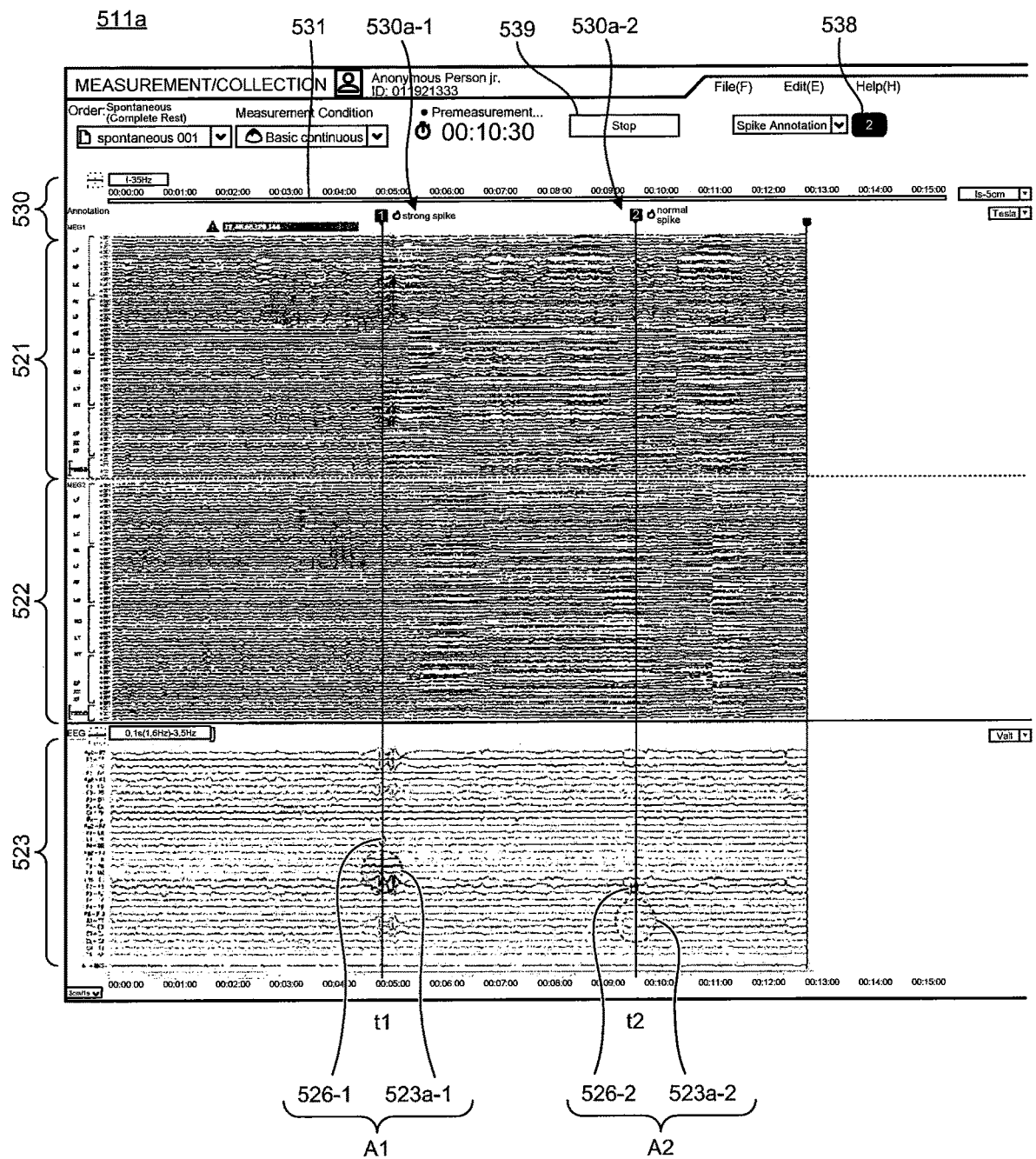
FIG. 8 is a diagram illustrating the state attained immediately after the input of annotation information.

FIG. 8 is a diagram illustrating the state attained immediately after the input of annotation information. More particularly, in FIG. 8 is illustrated the screen displayed immediately after the selection of "spike" from the popup window 535 at the time t2 and the input of text "normal spike". When an "OK" button is selected from the popup window 535 illustrated in FIG. 6, the popup window 535 closes and the annotation 530a-2 gets displayed at the corresponding time position in the first display area 530 as illustrated in FIG. 8. In a corresponding manner to the annotation number "2", the attribute icon representing "spike" and the text information "normal spike" is displayed. At the same time, the value of the counter box 538 is incremented. Moreover, an attribute icon 526-2 is displayed in the vicinity of the highlighted marking 523a-2. In this example, an attribute icon 526-1 is displayed in the vicinity of the marking 523a-1 too. However, as described above, it is possible to select whether to display or hide the attribute icons 526-1 and 526-2. An annotation A1 including the marking 523a-1 and the attribute icon 526-1 as well as an annotation A2 including the marking 523a-2 and the icon 526-2 is also included in the annotation information.

FIG. 9 is a diagram of the updated annotation list. As a result of adding an annotation, which corresponds to the marking 523a-2, in the area 511a on the left-hand side of the measurement collection screen 502; the annotation list 560 gets updated. A note "normal spike" gets added corresponding to the annotation number "2".

In an identical manner, every time a particular point or a particular range on the signal waveforms is specified in the area 511a during the measurement, the specified point is highlighted, and annotation information is displayed along the time axis 531 in the first display area 530. In the area 511b, annotation information gets sequentially added to the annotation list 560.

In the annotation list 560 and in the area 511a meant for signal waveform display, the display of annotation numbers is not mandatory and can be skipped. As long as the attached annotation can be identified, any arbitrary information can be used as identification information. For example, an attribute icon, an attribute string (such as "strong spike"), and a time in the vicinity of the time axis 531 can be displayed in a corresponding manner. Moreover, in the area 511a, a file number (the number displayed in a "File" item in FIG. 9) can also be displayed.

When the end button 539 (see FIG. 8) is pressed and the measurement is over, the highlighted points specified in the second display areas 521 to 523 are stored in a corresponding manner to the signal waveforms. The annotation. Information that is displayed at the corresponding time positions in the first display area 530 is also stored in a corresponding manner to the annotation numbers and the times. Moreover, related information such as the counter value of the counter box 538 and the content of the annotation list 560 is also stored. As a result of storing such display information, even when the person in charge of measurement and the analyst are two different persons, the analyst can easily recognize the problematic points and perform analysis.

Figure 10:
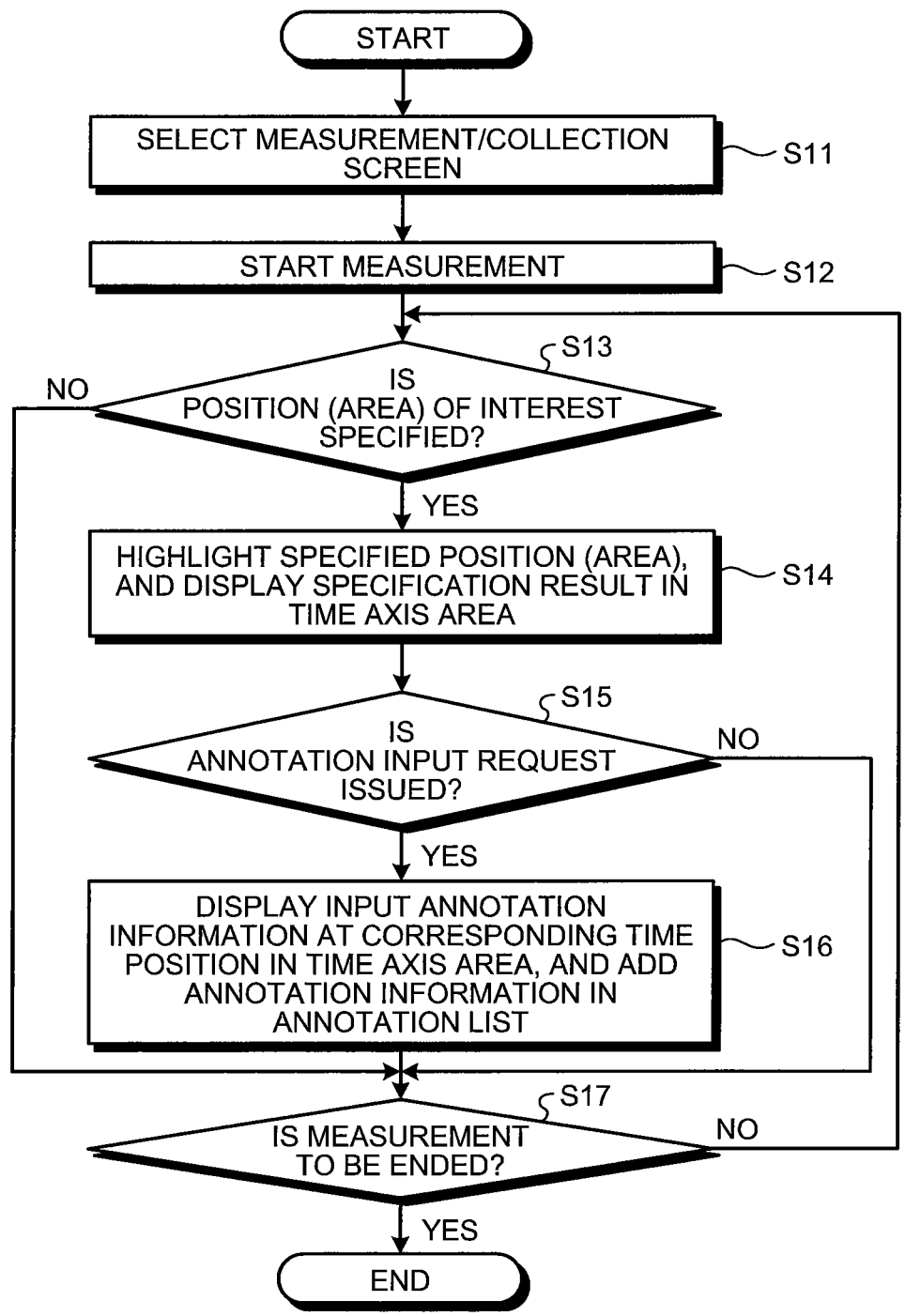
FIG. 10 is a flowchart for explaining an example of a measurement collection operation performed in the information processing device according to the embodiment.

FIG. 10 is a flowchart for explaining an example of a measurement collection operation performed in the information processing device according to the embodiment. Thus, explained below with reference to FIG. 10 is the measurement collection operation performed in the information processing device 50 according to the embodiment.

When "measurement/collection" is selected in the start screen 501 illustrated FIG. 4 (Step S11), the measurement is started and the waveforms of a plurality of signals are displayed in synchronization along the same time axis (Step S12). Herein, "a plurality of signal waveforms" include the signal waveforms detected by a plurality of sensors of the same type, and include a plurality of waveforms detected by a plurality of types of sensors. In this example, the waveforms of a plurality of biosignals include: the waveforms of magneto-encephalography signals obtained from a group of magnetic sensors corresponding to the right temporal region of the subject being measured; the waveforms of magneto-encephalography signals is obtained from a group of magnetic sensors corresponding to the left temporal region of the subject being measured; and the waveforms of electro-encephalography signals obtain from the electrodes meant for electro-encephalography of the subject being measured. However, that is not the only possible case. As far as the selection of sensors is concerned, defying the right-side sensor group and the left-side group, sensors can be arbitrarily selected from the regions such as the parietal region, the frontal lobe, and the temporal lobes. For example, in "MEG Window Control 1" illustrated in FIG. 7, if sensors for the frontal lobe are selected, the other sensors are selected in "MEG Window Control 2".

In the information processing device 50 it is determined whether or not a point interest or a range of interest is specified on the displayed signal waveforms (Step S13). If point of interest or a range of interest is specified (Yes at Step S13), then the specified point (range) is highlighted in the display areas for displaying the waveforms (i.e., the second display areas 521 to 523), and the specification result is displayed at the corresponding time position in the time axis area (the first display area 530) (Step S14). The specification result includes the information indicating that there was specification or includes identification information of the specification. Either at the same time of displaying the specification result in the time axis area, or before or after displaying the specification result in the time axis area, it is determined whether or not a request for inputting an annotation is issued (Step 15). If a request for inputting an annotation is issued (Yes at Step S15), the input annotation information is displayed at the corresponding time position in the time axis area and is added in the annotation list (Step S16). Then, it is determined whether or not a measurement end command is input (Step S17). Herein, if point (range) of interest is not specified (No at Step S13) or if a request for inputting an annotation is not issued (No at Step 15), then the system control proceeds to Step S17 for determination about ending the measurement. Until a measurement end command is input (Yes at Step S17), the operations at Steps S13 to S16 are performed in a repeated manner.

As a result of implementing such an information display method, when the signals are collected from a plurality of sensors, the measurement/collection screen 502 having a high degree of readability of signal information is provided.

(Analysis Operation Using Time-Frequency Analysis Screen)

Figure 11:
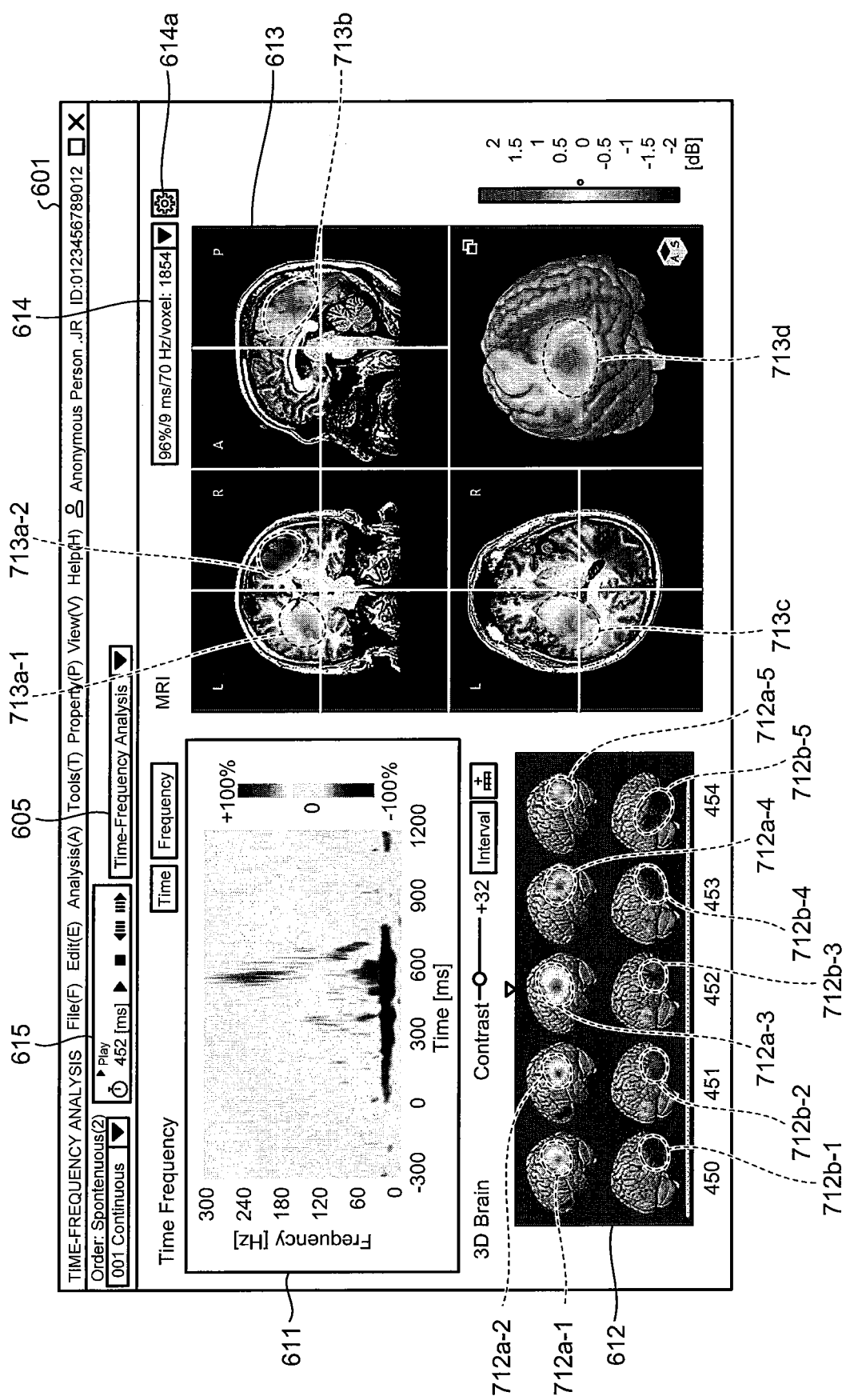
FIG. 11 is a diagram illustrating an example of a time-frequency analysis screen.
Figure 12:
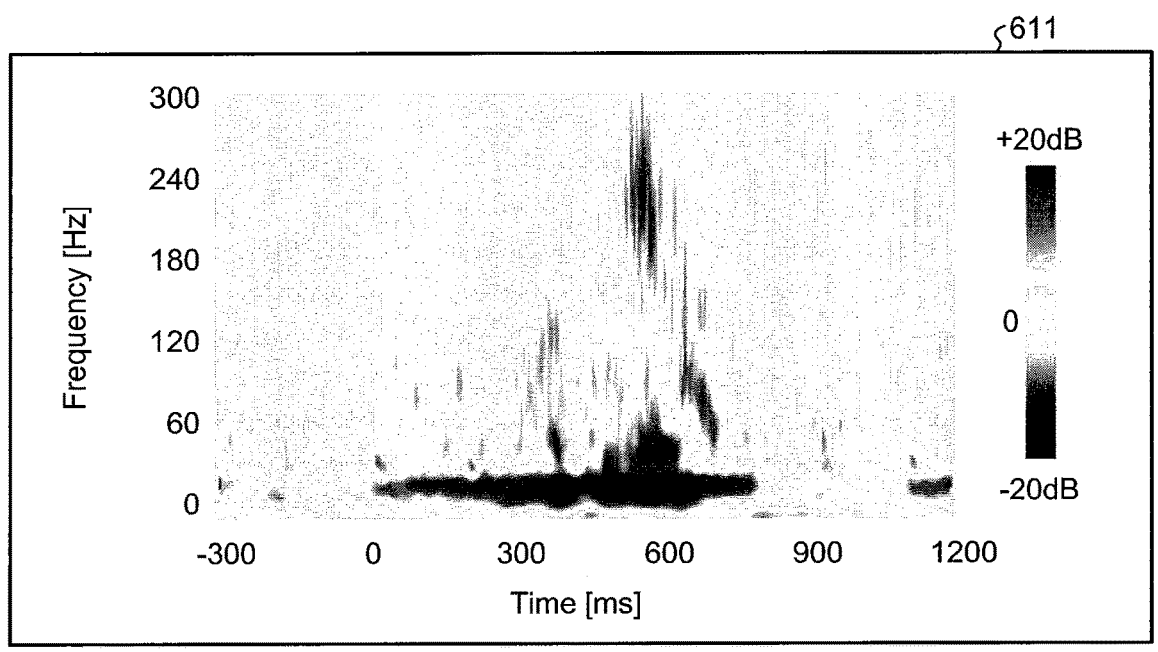
FIG. 12 is a diagram illustrating an example of a heat map in which a range described with decibel.

FIG. 11 is a diagram illustrating an example of the time-frequency analysis screen. Explained below with reference to FIG. 11 is an analysis operation performed using the time-frequency analysis screen 601 displayed in the information processing device 50.

In the start screen 501 illustrated in FIG. 4, when the "analysis" selection button is pressed, the analyzing unit 206 analyzes the sensor information (electro-encephalography signals or magneto-encephalography signals) obtained as a result of the measurement/collection operation performed using the measurement/collection screen 502, and biosignals indicating the signal intensity at each position inside the brain (an example of a biological site, and an example of a source). Examples of the method for calculating the signal intensities include spatial filtering that is a known method. Alternatively, some other method can also be implemented. In the start screen 501 illustrated in FIG. 4, when the "analysis" selection button is selected, the analysis display control unit 202 displays the time-frequency analysis screen 601, which is illustrated in FIG. 11, in the display device 107. As illustrated in FIG. 11, the time-frequency analysis screen 601 is used to display an analysis screen switching list 605, the heat map 611, the stereogram 612, the head region trihedral figure 613, the peak list 614, and the reproduction control panel 615. The main objective of performing analysis and measurement using the time-frequency analysis screen 601 is to identify and display the sites such as the visual area, the auditory area, the somatosensory area, the motor area, and the speech area that are vital for survival of a person. A peak list setting button 614a displayed on the right-hand side of the peak list 614 is meant for displaying a window for setting the conditions regarding the peaks that get registered in the peak list 614. Regarding the setting performed in response to the pressing of the peak list setting button 614a, the explanation is given later. Moreover, regarding the display and the operations of the heat map 611, the stereogram 612, the head region trihedral figure 613, the peak list 614, and the reproduction control panel 615; the detailed explanation is given later.

The analysis screen switching list 605 is a list that enables selection of various analysis screens. Examples of the analysis screens selectable from the analysis screen switching list 605 include the time-frequency analysis screen 601 meant for analyzing the biosignals using time and frequency according to the embodiment, and include an analysis screen meant for performing dipole estimation for estimating and analyzing sites, such as an epilepsy site, from the biosignals. In the embodiment, the explanation is given about the analysis operation performed using the time-frequency analysis screen 601.

<Regarding Heat Map>

Figure 13:
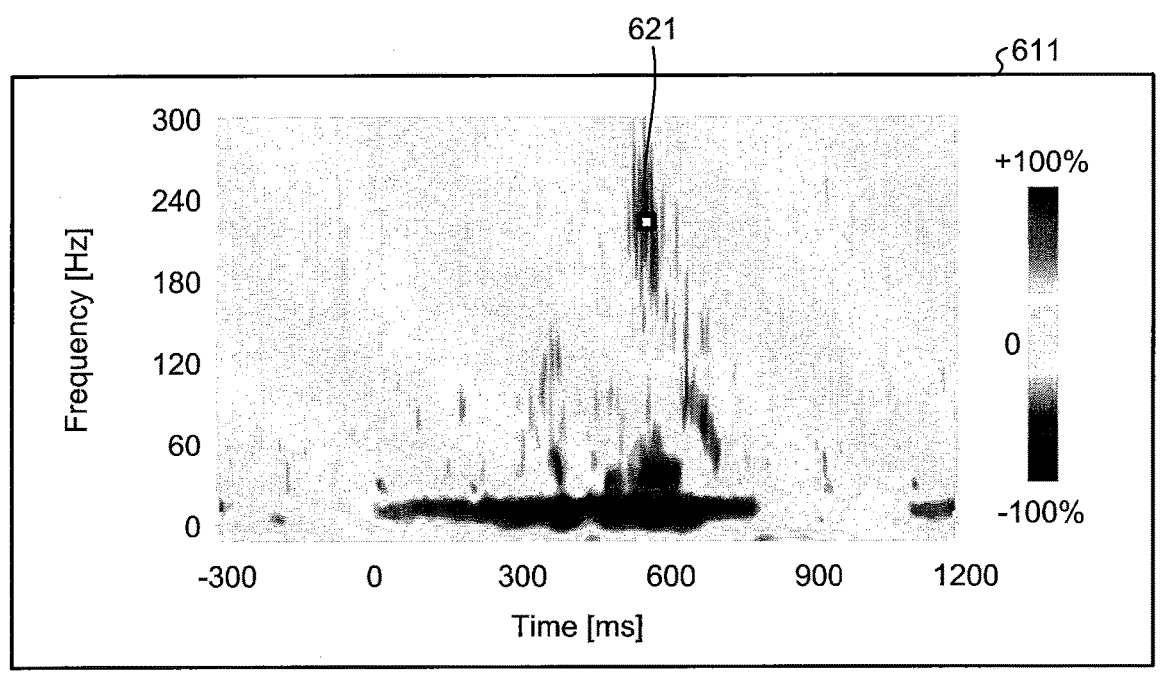
FIG. 13 is a diagram illustrating an example of the state in which a particular position is specified in a heat map.
Figure 14:
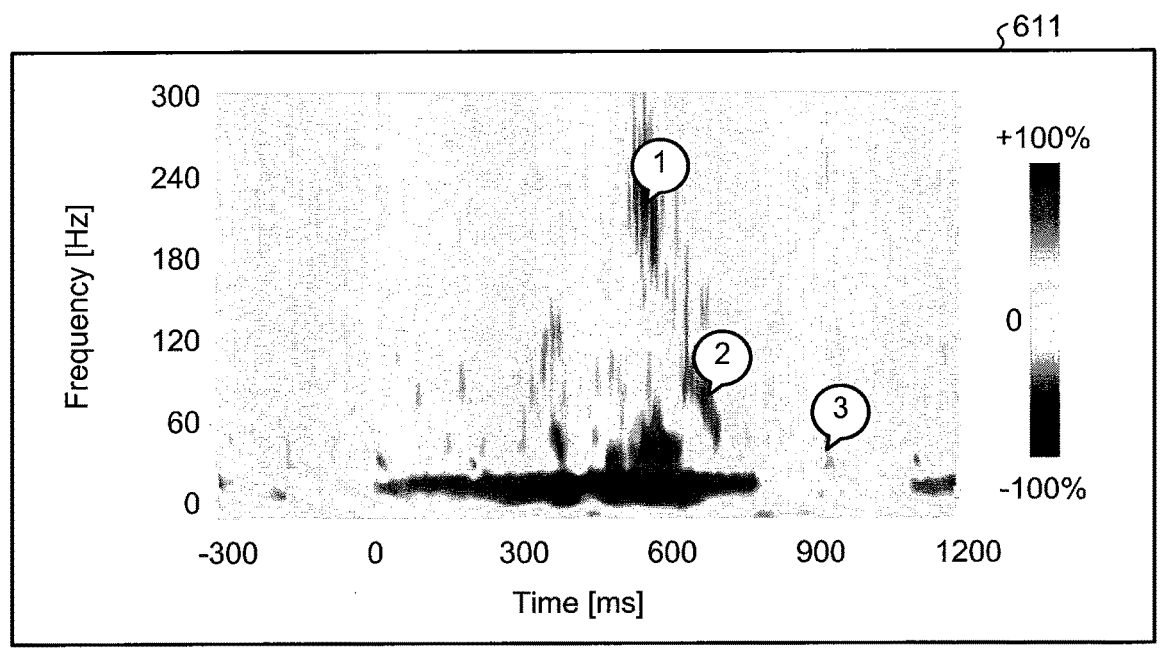
FIG. 14 is a diagram illustrating an example of the state in which three peak positions from a peak list are displayed in the heat map.
Figure 15:
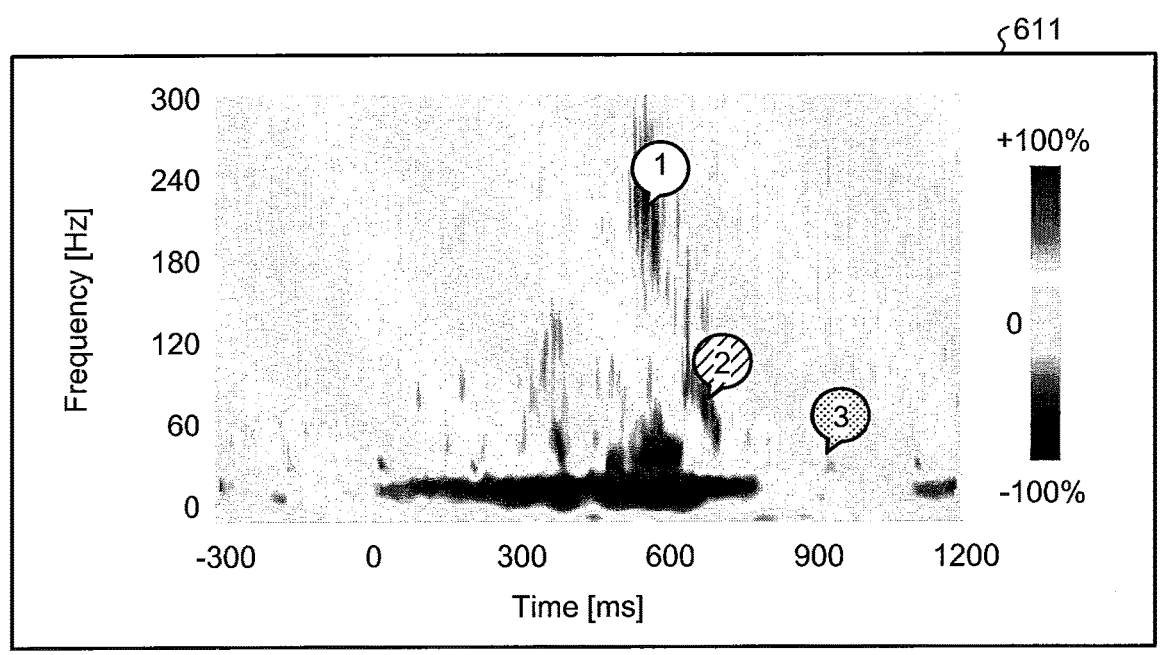
FIG. 15 is a diagram illustrating an example of the state in which the display forms in the heat map are varied according to the information about the peaks.
Figure 16:
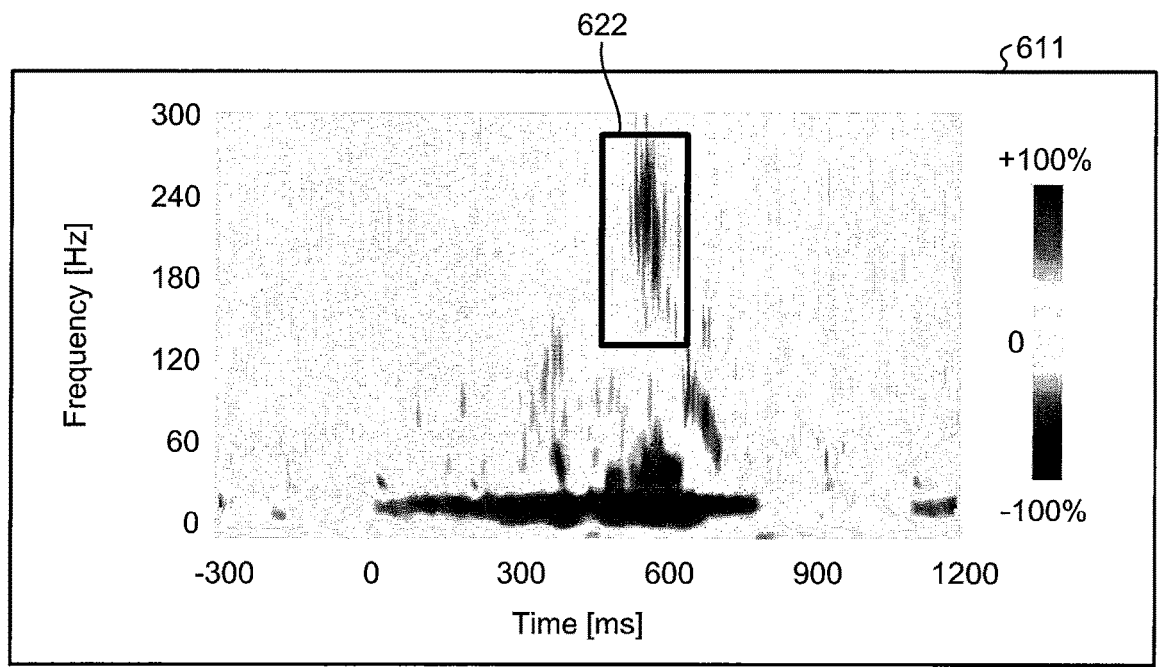
FIG. 16 is a diagram illustrating an example of the state in which a particular range is specified in the heat map.
Figure 17:
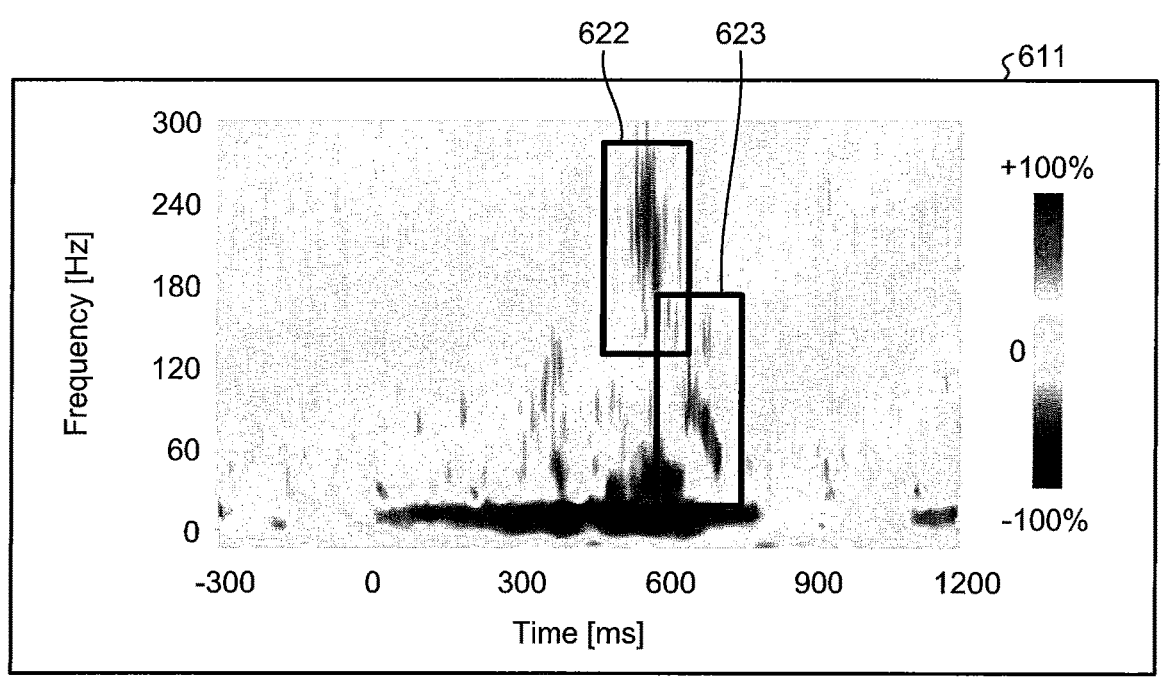
FIG. 17 is a diagram illustrating an example of the state in which a plurality of particular ranges is specified in the heat map.
Figure 18:
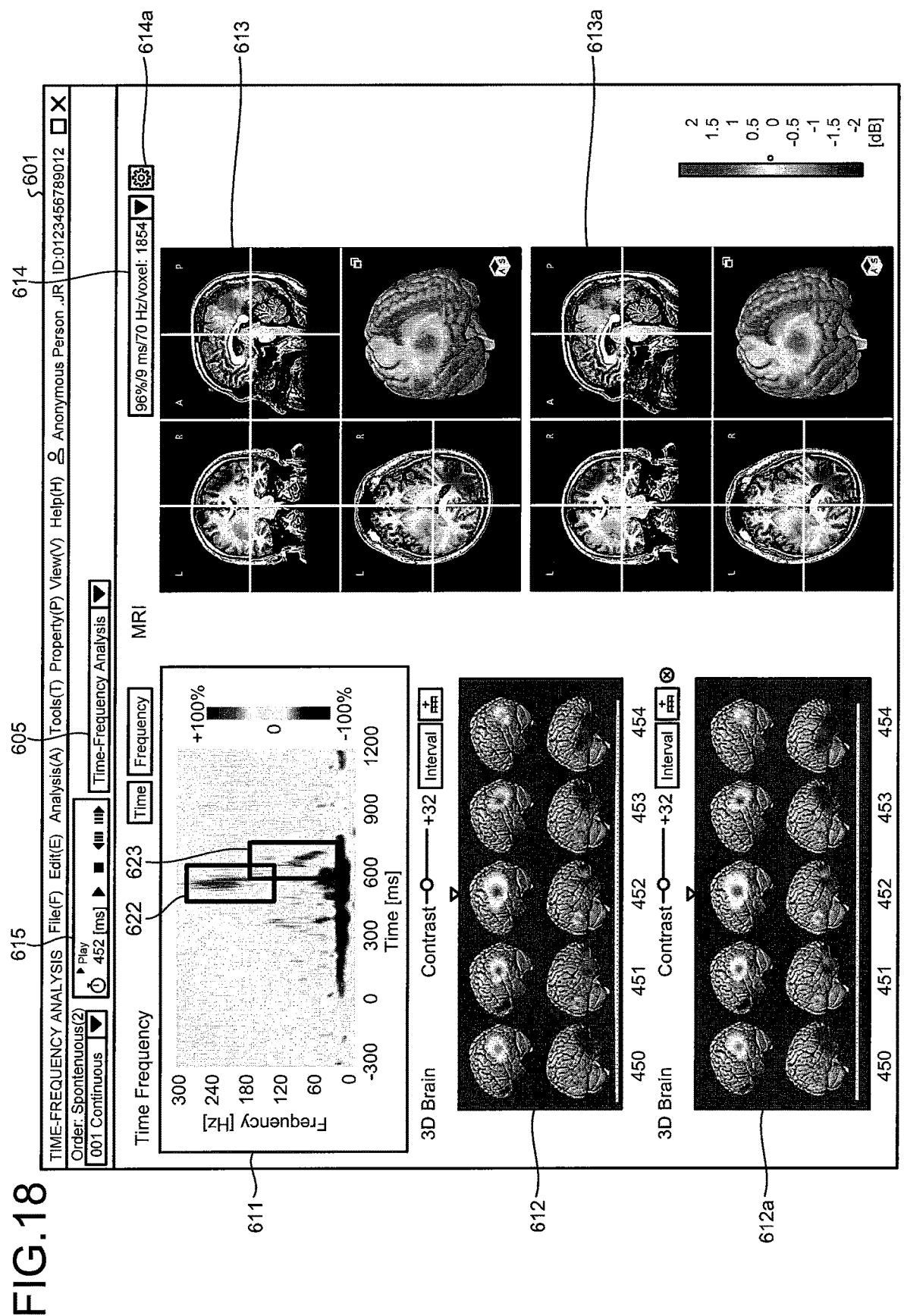
FIG. 18 is a diagram illustrating an example of the state in which a stereogram and a head region trihedral figure are added in the time-frequency analysis screen.

FIG. 13 is a diagram illustrating an example of the state in which a particular position is specified in the heat map. FIG. 14 is a diagram illustrating an example of the state in which three peak positions from the peak list are displayed in the heat map. FIG. 15 is a diagram illustrating an example of the state in which the display forms in the heat map are varied according to the information about the peaks. FIG. 16 is a diagram illustrating an example of the state in which a particular range is specified in the heat map. FIG. 17 is a diagram illustrating an example of the state in which a plurality of particular ranges is specified in the heat map. FIG. 18 is a diagram illustrating an example or the state in which a stereogram and a head region trihedral figure are added in the time-frequency analysis screen. Explained below with reference to FIGS. 12 to 17 are the operations performed regarding the heat map 611 in the time-frequency analysis screen 601.

As illustrated in FIG. 11, regarding the heat map 611, time-frequency analysis is performed with respect to biosignals indicating the signal intensity at each position inside the brain as calculated by the an analyzing unit 206; the horizontal axis represents the time (the time from the trigger time), the vertical axis represents the frequency; and the distribution of signal intensities of the biosignals as identified using the times and the frequencies (a first intensity distribution) is illustrated using colors. In the example illustrated in FIG. 11, for example, the signal intensities are indicated by an increase or a decrease with reference to a predetermined standard. For example, as far as the predetermined standard is concerned, when there is no stimulation to the subject being tested, the average value of the signal intensities is assumed to be 0[%]. In the present embodiment, illustration is made with 0±100 [%], but this is not the limitation, and the display may be made while changing the range. Further, instead of unit [%], illustration may be made width [db] (decibel) as in the heat map 611 in FIG. 12, for example. Moreover, in the heat map 611, for example, when some sort of stimulation is given (such as giving a physical impact, moving an arm, uttering a word, or listening to a sound) to the subject being tested at a time 0 [ms], the state of post-stimulation activity of the brain is indicated at the later times than the time 0 [ms]; and the state of pre-stimulation activity of the brain is indicated at the earlier times than the time 0 [ms]. Meanwhile, the operation of displaying the heat map 611 is controlled by the heat map display control unit 211.

As illustrated in FIG. 13, the analyst can perform an operation input (clicking or tapping) using the input unit 208 and specify a particular position (point) in the heat map 611. As illustrated in FIG. 13, the heat map display control unit 211 displays the specified position as, for example, a specified portion 621. Herein, although the specified portion 621 is illustrated as a white blank rectangle, that is not the only possible case; and the specified portion. 621 can be illustrated in some other display form.

Moreover, in the heat map 611 illustrated in FIG. 13, although the position that is specified by performing an operation input using the input unit 208 is displayed, it is alternatively possible to display a heat map using the time and the frequency of the peak selected from among the peaks registered in the peak list 614 and to display the concerned peak position. Alternatively, for example, the positions of N number of upper-level peaks from the peak selected in the peak list 614 can be displayed in the heat map 611. In the example illustrated in FIG. 14, the positions of the upper three peaks are displayed. Meanwhile, the manner of displaying the positions of the peaks can be decided depending on the settings. For example, other than the examples given above, it is possible to switch to the setting of not displaying the peaks, or to the setting of displaying the peaks having the signal intensity of M or higher.

As illustrated in FIG. 15, regarding a plurality of peaks displayed in the heat map 611, the display form can be varied according to the attribute information of those peaks. In the example illustrated in FIG. 15, numbers are assigned to the displayed peaks, and the display portions of the numbers are set to have mutually different colors.

As described above, when particular positions are specified in the heat map 611, the distribution of signal intensities of the biosignals corresponding to the times and the frequencies at the specified positions is displayed as a heat map (different than the heat map in the heat map 611) as follows: for example, as illustrated in FIG. 11, in the stereogram 612 of the bran, sites 712a-1 to 712a-5 and sites 712b-1 to 712b-5 are displayed; and, in the head region trihedral FIG. 613 of the brain, sites 713a-1, 713a-2, 713b, 713c, and 713d are displayed. More particularly, the signal intensities of the biosignals corresponding to the times and the frequencies at the specified positions in the heat map 611 are displayed as a heat map having red and blue colors.

As illustrated in FIG. 16, the analyst can perform a dragging operation or a swiping operation using the input unit 208, and specify a particular range in the heat map 611. As illustrated in FIG. 16, for example, the heat map display control unit 211 displays the specified range as a specified area 622 of a rectangular shape having the dimensions defined by the dragging operation. Although the specified area 622 is illustrated as a white blank rectangle, that is not the only possible case; and the specified area 622 can be illustrated in some other display form such as a round shape or a free shape.

In this way, when a particular range is specified in the heat map 611, the distribution of the average of the signal intensities of the biosignals corresponding to the times and the frequencies included in the specified range is displayed as a heat map (different than the heat map in the heat map 611) as follows: for example, as illustrated in FIG. 11, in the stereogram 612 of the brain, the sites 712a-1 to 712a-5 and the sites 712b-1 to 712b-5 are displayed; and, in the head region trihedral figure 613 of the brain, the sites 713a-1, 713a-2, 713b, 713c, and 713d are displayed.

As illustrated in FIG. 17, the analyst can perform an additional operation (such as a dragging operation using right clicking, or a new swipe operation) using the in unit 208, and additionally specify a specified area, such as a specified area 623, other than the already specified specified area 622. In that case, as the stereogram and the head region trihedral figure for the newly-specified specified area 623; a stereogram 612a and a head region trihedral figure 613a are displayed as illustrated in FIG. 18. Then, the distribution of the average of the signal intensities of the biosignals corresponding to the times and the frequencies included in the specified area 623 is displayed as a heat map (different than the heat map in the heat map 611) in the stereogram 612a of the brain and the head region trihedral figure 613a of the brain. If a plurality of sets of specified information is received in the heat map 611, then the stereogram 612 and the head region trihedral figure 613 corresponding to each set of information are displayed from top to bottom in the sequence of reception of the sets of information. In the example illustrated in FIG. 18, it is illustrated that the specified areas 622 and 623 are selected in that order. As a result of such a display, it becomes easier to get an intuitive understanding. Meanwhile, if a plurality of selected sets of information is received in the heat map 611, then the stereogram 612 and the head region trihedral figure 613 corresponding to each set of information can be alternatively displayed from bottom to top in the sequence of reception of the sets of information. In that case, the stereogram 612 and the head region trihedral figure 613 corresponding to the lastly-specified selection area are displayed right below the heat map 611. Hence, it becomes possible to reduce the eye movement among the heat map 611, the stereogram 612, and the head region trihedral figure 613. Meanwhile, in the case of specifying a plurality of positions in the neat map 611, the specification is not limited to the ranges such as the specified areas 622 and 623, and it is also possible to specify a plurality of point positions such as the specified portion 621. In this way, when a plurality of positions (points or areas) is specified in the heat map 611, it becomes possible to compare the distributions of the signal intensities of the biosignals corresponding to the specified times and frequencies.

<Regarding Stereogram>

Figure 19:
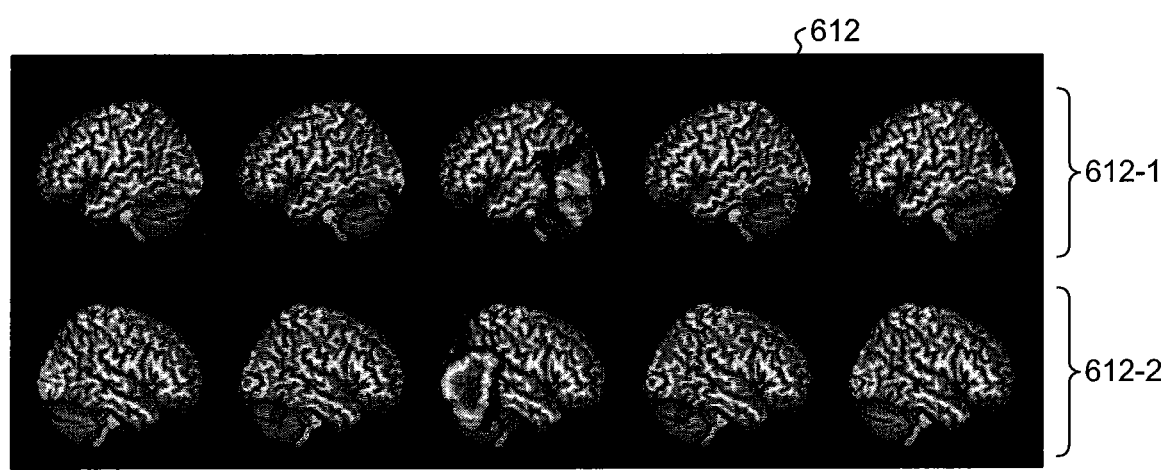
FIG. 19 is a diagram illustrating an example of the stereogram in the time-frequency analysis screen.
Figure 21:
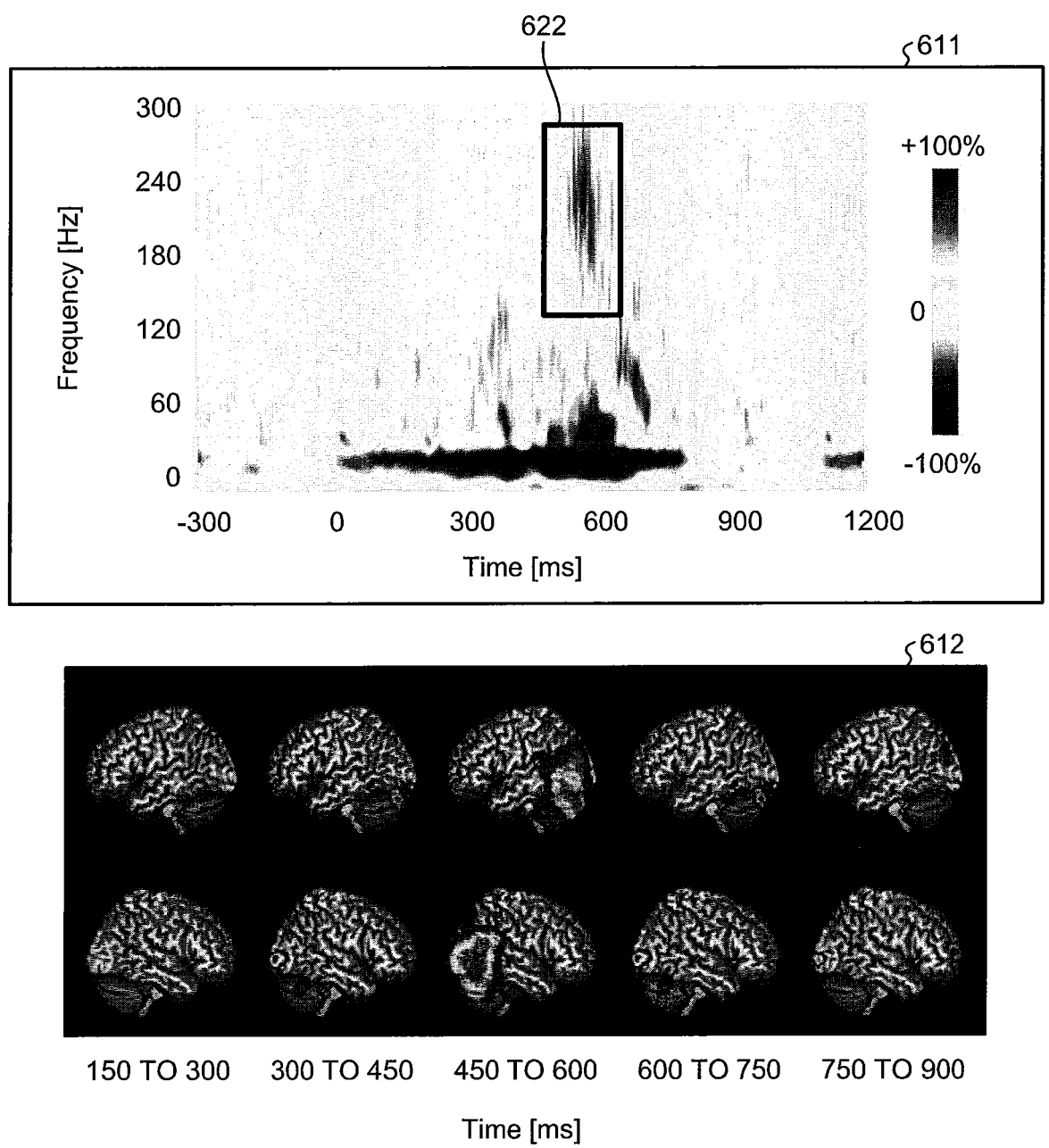
FIG. 21 is a diagram illustrating an example of the state in which the state of the brain corresponding to the specified range in the heat map is displayed in the center of the stereogram.
Figure 22:
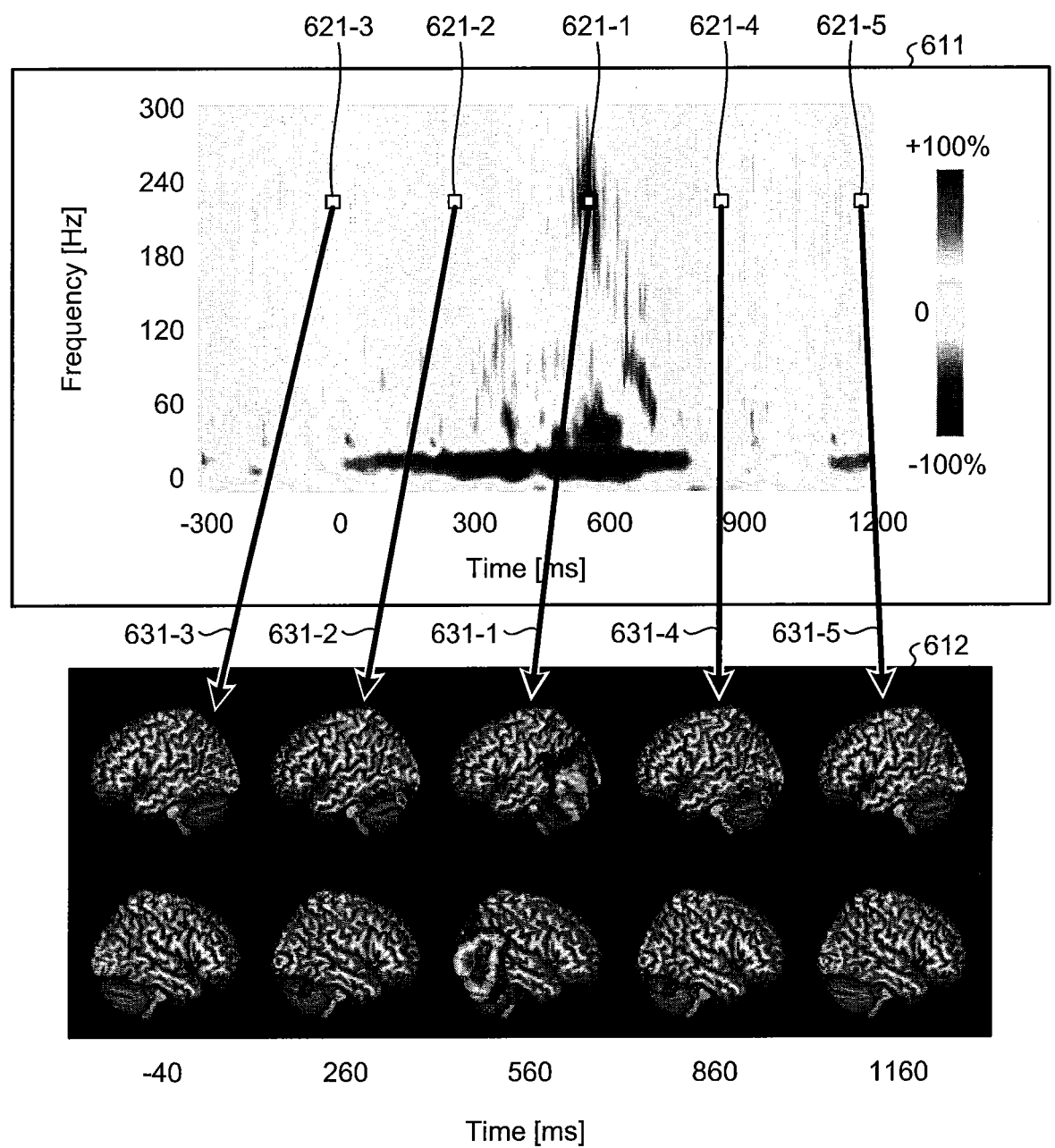
FIG. 22 is a diagram illustrating an example of the state in which line segments indicate which brain image displayed in the stereogram corresponds to which time and frequency.
Figure 23:
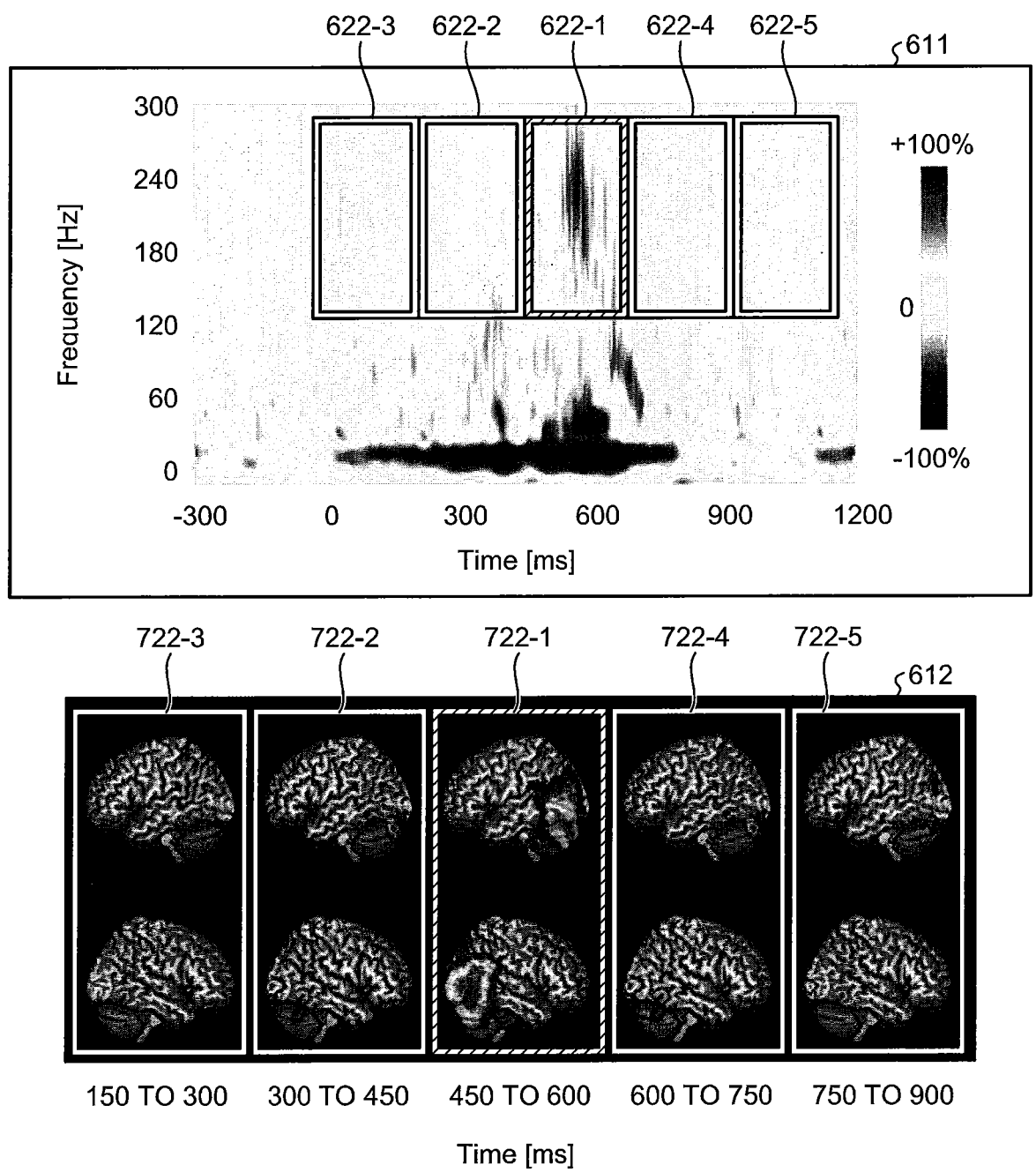
FIG. 23 is a diagram illustrating an example of the state in which rectangular areas indicate which brain image displayed in the stereogram corresponds to which time and frequency.
Figure 24:
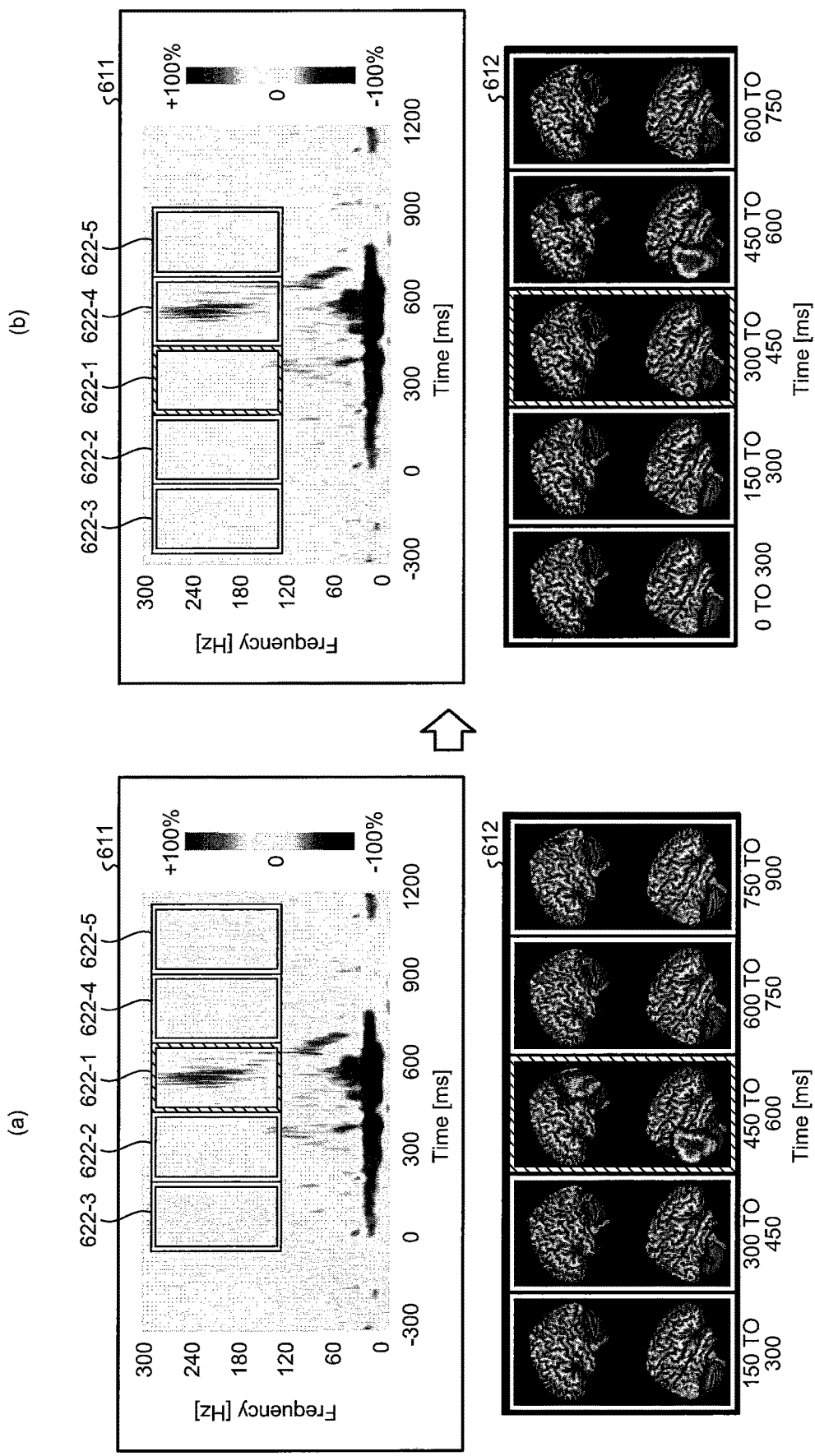
FIG. 24 is a diagram illustrating an example of the state in which the display the stereogram and the display of the rectangular areas in the heat map move as a result of dragging performed in the stereogram.
Figure 25:
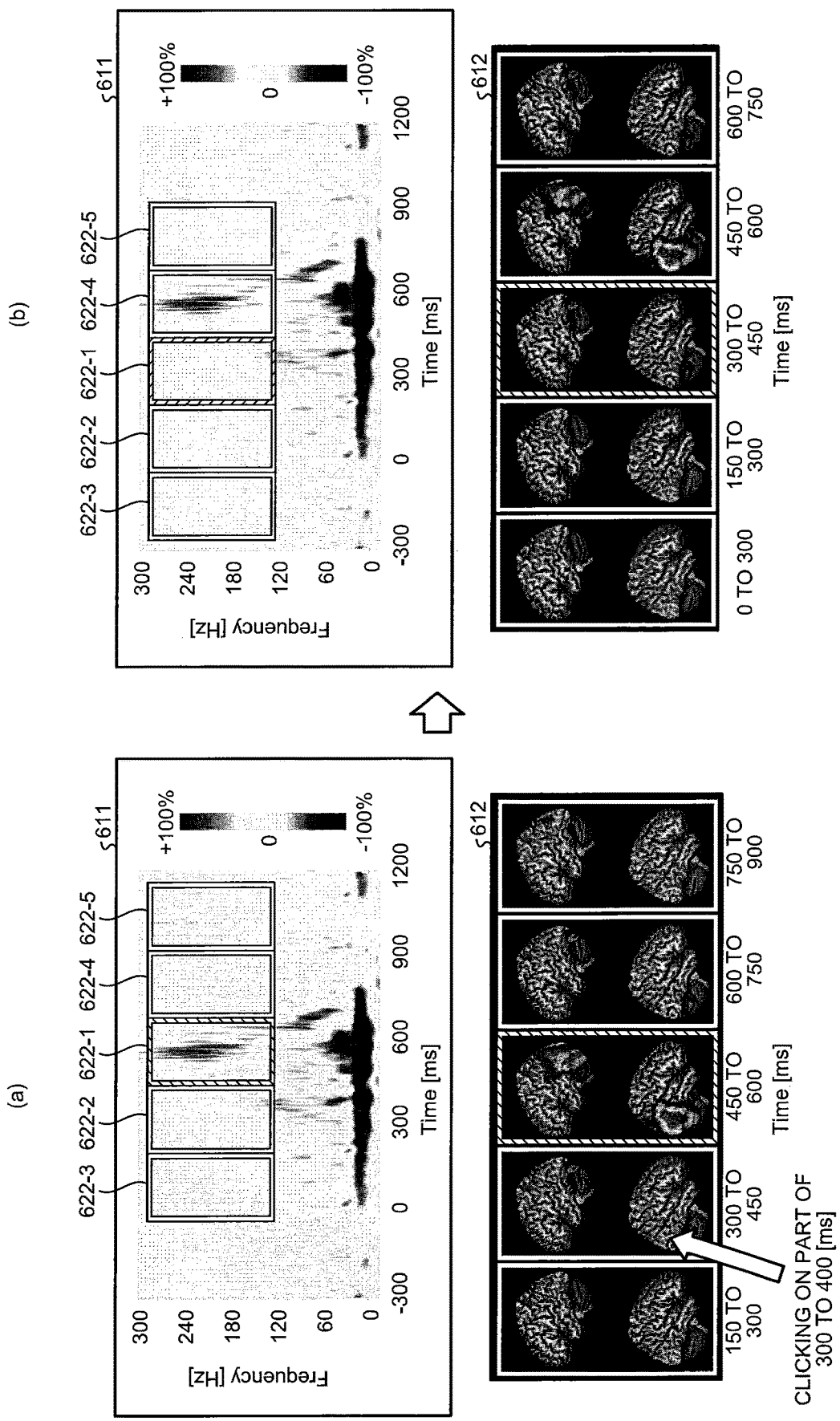
FIG. 25 is a diagram illustrating an example of the state in which the display of the stereogram and the display of the rectangular areas in the heat map move as a result of clicking the display one brain image in the stereogram.

FIG. 19 is a diagram illustrating an example of the stereogram in the time-frequency analysis screen. FIG. 20 is a diagram illustrating an example of the state in which the state of the brain corresponding to the specified position in the heat map is displayed in the center of the stereogram. FIG. 21 is a diagram illustrating an example of the state in which the state of the brain corresponding to the specified range in the heat map is displayed in the center of the stereogram. FIG. 22 is a diagram illustrating an example of the state in which line segments indicate which brain image displayed in the stereogram corresponds to which time and frequency. FIG. 23 is a diagram illustrating an example of the state in which rectangular areas indicate which brain image displayed in the stereogram corresponds to which time and frequency. FIG. 24 is a diagram illustrating an example of the state in which the display the stereogram and the display of the rectangular areas in the heat map move as a result of dragging performed in the stereogram. FIG. 25 is a diagram illustrating an example of the state in which the display of the stereogram and the display of the rectangular areas in the heat map move as a result of clicking the display of any one bran image in the stereogram. Explained below with reference to FIGS. 18 to 24 is are fundamental operations for displaying the stereogram 612 in the time-frequency analysis screen 601.

As illustrated in FIG. 19, the stereogram 612 is a diagram for displaying stereographic images (three-dimensional images) from predetermined viewpoints; and is used in displaying, as a heat map (a second intensity distribution) in a superimposed manner, the specified posit-on (point or range) in the heat map 611 or the signal intensities of the biosignals corresponding to the position of the peak selected from the peak list 614. As illustrated in FIG. 19, in the stereogram 612, stereoscopic images of the brain that are taken from the same viewpoint are displayed in the same row. In the example illustrated in FIG. 19, the stereoscopic images of the brain as displayed in a display area 612-1, which represents the upper row in the stereogram 612, represent the images taken from the viewpoint from the left lateral of the brain; and the stereoscopic images of the brain as displayed in a display area 612-2, which represents the lower row in the stereogram 612, represent the images taken from the viewpoint from the right lateral of the brain. Meanwhile, the operation for displaying the stereogram 612 is controlled by the stereoscopic display control unit 212.

The stereogram 612 illustrated in FIG. 19 is a brain stereogram when viewed from two viewpoints, that is, is a brain stereogram having two rows. However, that is not the only possible case. Alternatively, the stereogram 612 having a different number of rows can be displayed, and the number of rows can be made variable in the settings. For example, regarding the measurement of the speech area, since the measurement from the left-hand side as well as the right-hand side serves as critical information, a brain stereogram from the two viewpoints of the left lateral and the right lateral can be displayed (a stereogram having two rows can be displayed). Given below in (Table 1) is an example of the correspondence between the measurement targets and the viewpoints. A measurement target represents a stimulation given during the measurement to the subject being tested (the stimulation is given using a stimulation device and corresponds to one of No. 1 to No. 4 in (Table 1)), or represents an action of the subject being tested (No. 5 in (Table 1)); and is the item selected in the measurement/collection screen during the measurement. As a result of selecting the measurement target, the brain stereogram of the corresponding viewpoint is displayed. Herein, a viewpoint indicates the direction with the front side of the subject being tested representing the starting point. Meanwhile, it can also be made possible to separately set the number of rows. The stereogram illustrated in FIG. 19 corresponds to No. 2 in (Table 1). In the following explanation, as a matter of convenience, the stereogram 612 is assumed to include two rows (two viewpoints).

TABLE 1

Relationship between measurement target and viewpoint

| No. | Measurement target | Viewpoint |
| --- | --- | --- |
| 1 | Visual sense | Rear (viewpoint toward occipital region from behind) One row |
| 2 | Auditory sense | Left-hand side (viewpoint toward left temporal region from outside of left temporal region) and right-hand side (viewpoint toward right temporal region from outside of right temporal region) One row for left-hand side and one row for right-hand side |
| 3 | Speech perception | Left-hand side and right-hand side |
| 4 | Somatic sense | Upper side |
| 5 | Motor perception | Upper side |

As illustrated in FIG. 20, when the specified portion 621 is specified in the heat map 611, the stereoscopic display control unit 212 displays, in the stereogram 612 and with the time corresponding to the specified portion 621 serving as the center of the display area of the stereogram 612, a heat map of the signal intensities in the brain corresponding to the earlier times and the later times. In the example illustrated in FIG. 20, the time of 560 [ms] is specified in the heat map 611. Hence, with the time of 560 [ms] serving as the center in the stereogram 612, the neighboring display times for the brain, such as 550 [ms], 555 [ms], 560 [ms], 565 [ms], and 570 [ms], are displayed at the interval of 5 [ms]. However, it can be made possible to vary the interval between the neighboring display times for the brain images to 10 [ms] or 25 [ms] in the settings.

As illustrated in FIG. 21, when a range (the specified area 622) is specified in the heat map 611, the heat map of the average signal intensity of the signal intensities in the specified area 622 can be displayed in the stereogram 612. In that case, it can be made possible to adjust and set the times of neighboring stereoscopic images, which are displayed in the stereogram 612, according to the selected range of times. For example, as illustrated in FIG. 21, when the specified area 622 is in the range from 450 [ms] to [600] ms, if the neighboring stereoscopic images to be displayed in the stereogram 612 are set to have the display interval of 150 [ms], then the stereoscopic image displayed in the center of the stereogram 612 corresponds to the range from 450 [ms] to 600 [ms]. With reference to the stereoscopic image in the center of the stereogram 612, the stereoscopic image on the left-hand side can be set to correspond to the range from 300 [ms] to 450 [ms], and the stereoscopic image on the right-hang side can be set to correspond to the range from 600 [ms] to 750 [ms]. Moreover, the heat map displayed in each stereoscopic image represents the average value of the corresponding duration.

Explained below with reference to FIGS. 21 and 22 is the association between a position or a range in the heat map 611 and the stereoscopic images in the stereogram 612. As far as such association is concerned, firstly, as illustrated in FIG. 22, when a specified portion 621-1 representing a particular point position is specified in the heat map 611, a stereoscopic image of the brain corresponding to the time and the frequency of the specified portion 621-1 (a first image) is displayed in the stereogram 612. In that case, with that stereoscopic image of the brain serving as the center, stereoscopic images of the brain corresponding to the earlier times and the later times (second images) are displayed (in the example illustrated in FIG. 22, the brain images corresponding to five time, are displayed). Hence, the heat map display control unit 211 displays, in the heat map 611, the points corresponding to those times of the brain images as corresponding portions 621-2 to 621-5. In that case, frequency positions of the corresponding portions 621-2 to 621-5 are matched with the frequency position of the specified portion 621-1. Moreover, as illustrated in FIG. 22, the heat map display control unit 211 displays line segments 631-1 to 631-5 that loin the specified portion 621-1 and the corresponding portions 621-2 to 621-5, which are displayed in the heat map 611, to the corresponding stereoscopic images of the brain in the stereogram 612. As a result, it becomes possible to check, in one glance, about which state of the brain as displayed in the stereogram 612 corresponds to which position in the heat map 611. In the example illustrated in FIG. 22, although line segments are used, other methods for enabling confirmation of association can include matching the markings of the specified portion 621-1 and the corresponding portions 621-2 to 621-5 to the background colors of the brain images in the stereogram 612. In that case, the specified portion 621-1 that is specified by the analyst can be displayed in a distinguishable manner from the corresponding portions 621-2 to 621-5.

When a specified area 622-1 representing a particular range is specified in the heat map 611, firstly, as illustrated in FIG. 23, a stereoscopic image of the brain corresponding to the time and the frequency of the specified area 622-1 is displayed in the stereogram 612. In that case, with that stereoscopic image of the brain serving as the center, stereoscopic images of the brain corresponding to the earlier time ranges and later time ranges are displayed (in the example illustrated in FIG. 23, the brain images corresponding to five time ranges are displayed). Hence, the heat map display control unit 211 displays the ranges corresponding to the time ranges of the brain images as corresponding areas 622-2 to 622-5 in the heat map 611. Moreover, in that case, the specified area 622-1 that is specified by the analyst can be displayed in a distinguishable manner from the corresponding areas 622-2 to 622-5. For example, the rectangular frame of only the specified area 622-1 can be displayed in a different color. Furthermore, as illustrated in FIG. 23, the stereoscopic display control unit 212 displays rectangles, which are identical to the specified area 622-1 and the corresponding areas 622-2 to 622-5 in the heat map 611, to enclose the corresponding stereoscopic images of the brain in the stereogram 612. As a result, it becomes possible to check, in one glance, about which state of the brain as displayed in the stereogram 612 corresponds to which position in the heat map 611. Meanwhile, when the specified area 622-1 representing a particular area in the heat map 611 is specified, along with displaying the frames for the specified area 622-1 and the corresponding areas 622-2 to 622-5, frames 722-1 to 722-5 and a heat map can also be displayed in the stereogram 612.

Explained below with reference to FIGS. 23 and 24 is an operation of moving the di of the stereogram 612 to the right and left sides in response to a dragging operation, a swiping operation, or a cursor key operation performed on the stereogram 612. FIG. 24 illustrated an example of the state in which the stereoscopic images displayed in the stereogram 612 are moved to the right-hand side in response to a dragging operation, a swiping operation, or a cursor operation performed on the stereogram 612. In that case, as illustrated in FIG. 24, as a result of the movement, the time display also gets updated according to the displayed brain images, and the rectangle get displayed in such a way that the stereogram of the brain displayed in the center of the stereogram 612 gets selected. Moreover, accompanying the movement of the stereoscopic images in the stereogram 612, the stereoscopic display control unit 212 also moves the display of the specified area 622-1 and the corresponding areas 622-2 to 622-5 in the heat map 611.

As illustrated in FIG. 25, if a stereoscopic image other than the central stereoscopic image in the stereogram 612 gets selected as a result of a clicking operation or a tapping operation performed the analyst; the concerned stereoscopic image of the bran moves to the center of the stereogram 612. Meanwhile, it is also possible to have a configuration in which the images of the brain are kept stationary and only the overlapping heat map is moved. In that case, as illustrated in FIG. 25, as a result of the movement, the time display also gets updated according to the displayed brain images, and the rectangles get displayed in such a way that the stereogram of the brain displayed in the center in the stereogram 612 gets selected. Moreover, accompanying the movement of the stereoscopic images in the stereogram 612, the stereoscopic display control unit 212 also moves the display of the specified area 622-1 and the corresponding areas 622-2 to 622-5 in the heat map 611.

As described above, since the in the stereogram can be moved freely, the changes in the state of the bran before and after the concerned time can promptly checked.

Figure 26:
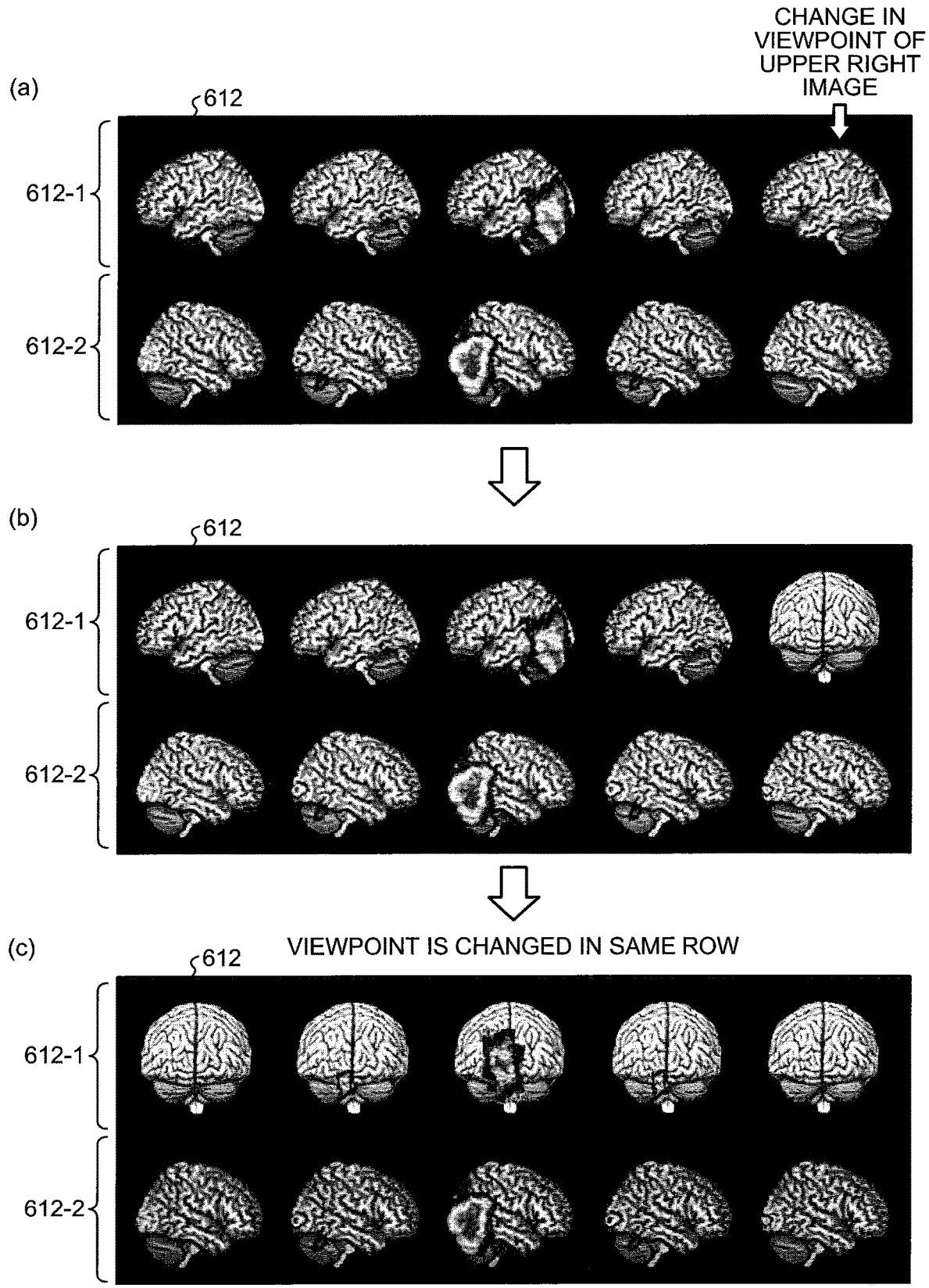
FIG. 26 is a diagram illustrating an example of the state in which, when the viewpoint or any one of the brain images displayed in the stereogram is changed, the viewpoints of all brain images in the same row get changed.
Figure 27:
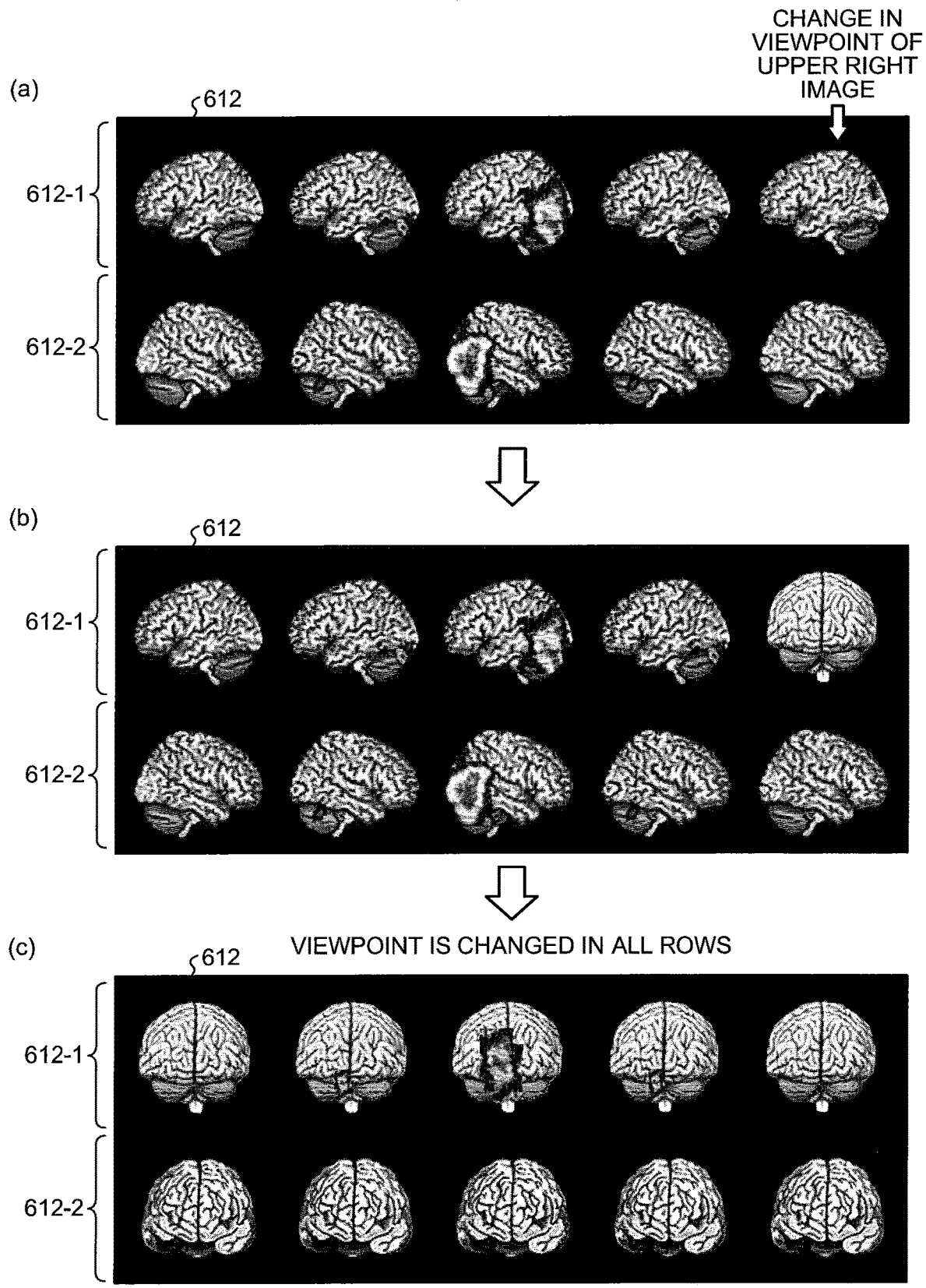
FIG. 27 is a diagram illustrating an example of the state in which, when the viewpoint of any one of the brain images displayed in the stereogram is changed, the viewpoints or all brain images in all rows get changed.
Figure 28:
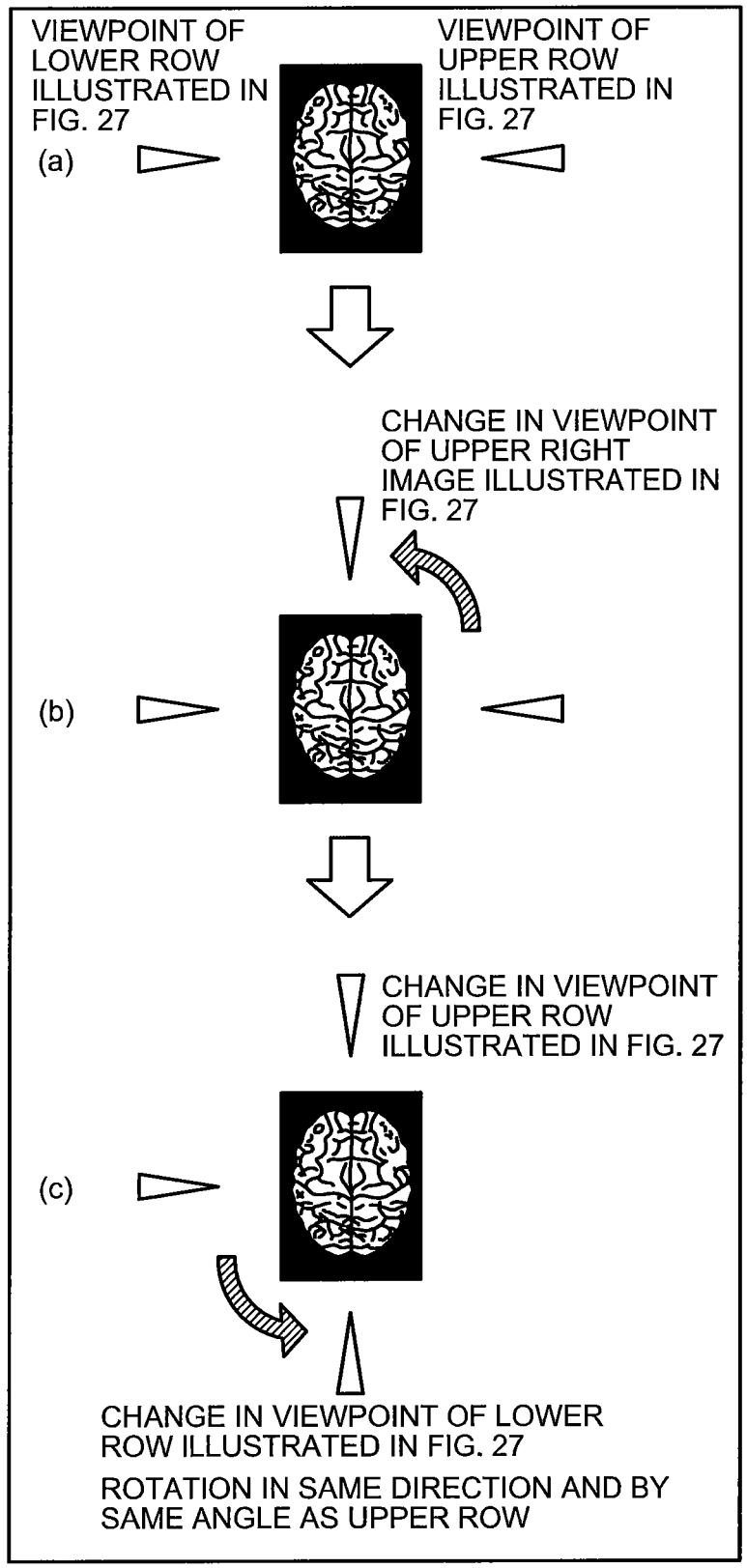
FIG. 28 is a diagram for explaining in a concrete manner the operation of changing the viewpoint in the example illustrated in FIG. 27.
Figure 29:
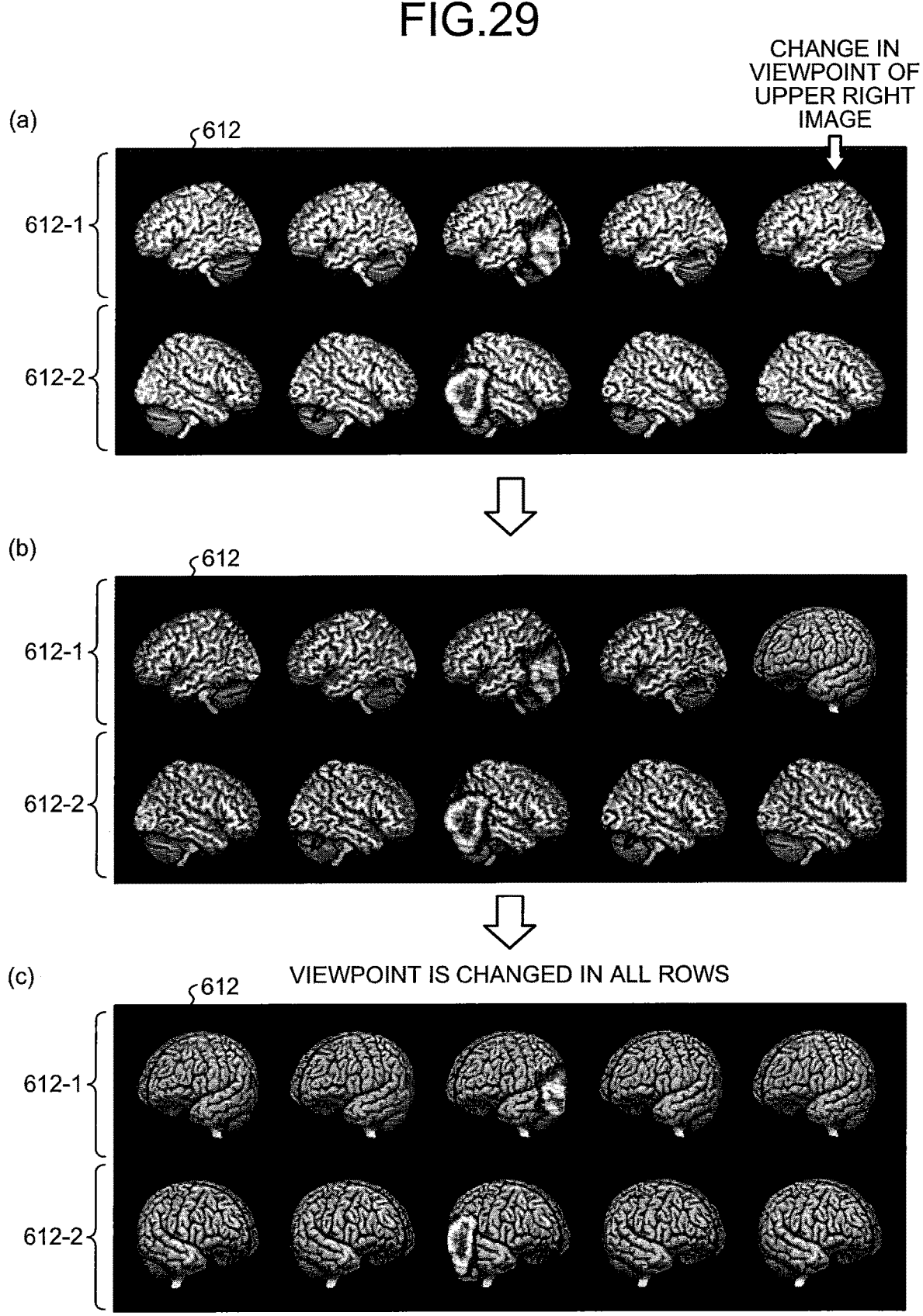
FIG. 29 is a diagram illustrating another example of the state in which, when the viewpoint of any one of the brain images displayed in the stereogram is changed, the viewpoint of all brain images in all rows get changed.
Figure 30:
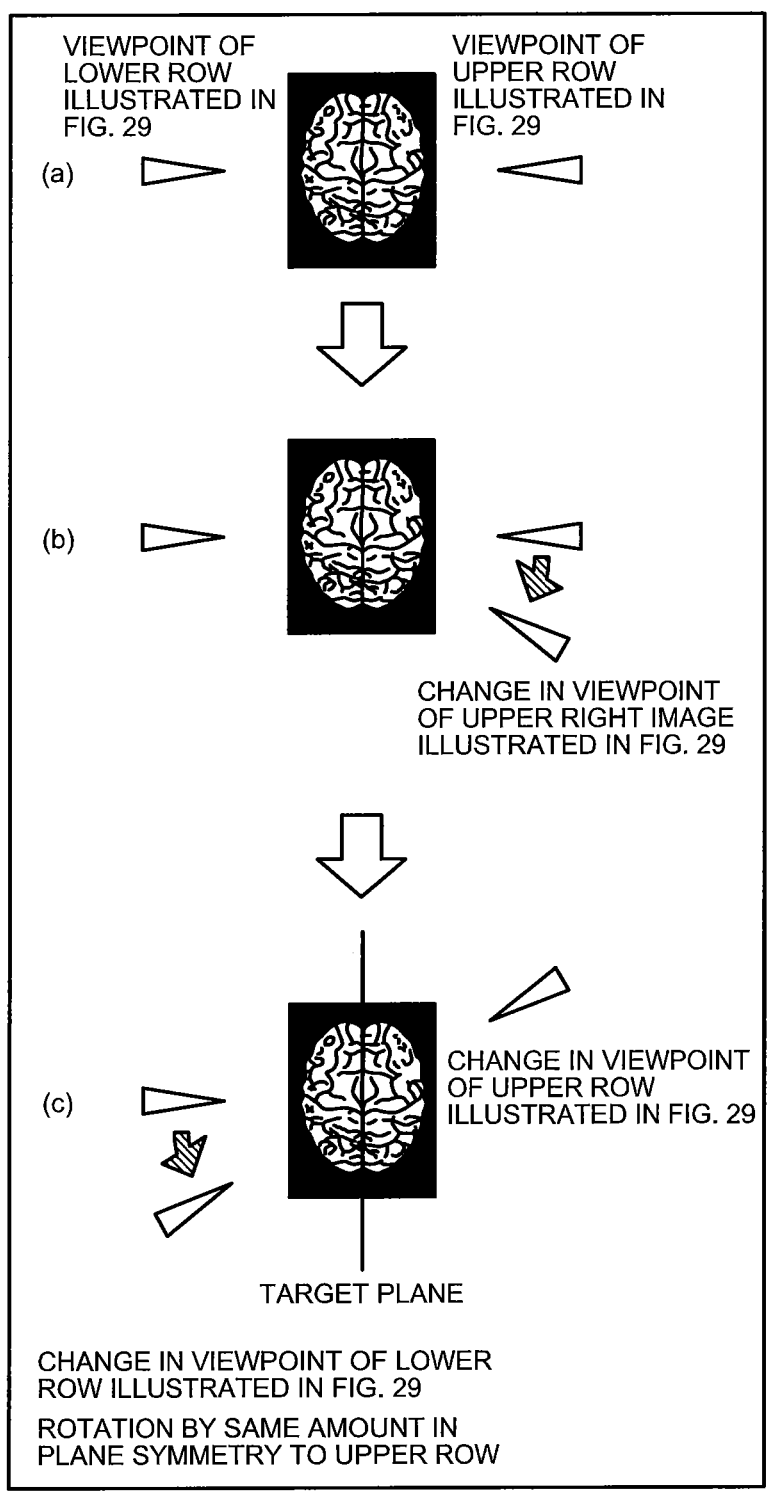
FIG. 30 is a diagram for explaining in a concrete manner the operation of changing the viewpoint in the example illustrated in FIG. 29.
Figure 31:
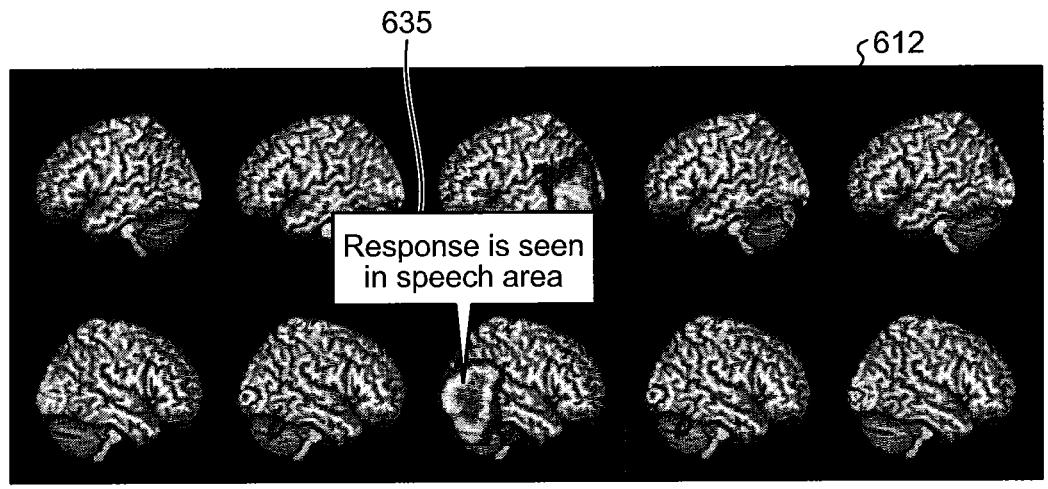
FIG. 31 is a diagram illustrating an example of the state in which a comment is added in the stereogram.

FIG. 26 is a diagram illustrating an example of the state in which, when the viewpoint of any one of the brain images displayed in the stereogram is changed, the viewpoints of all brain images in the same row get changed. FIG. 27 is a diagram, illustrating an example of the state in which, when the viewpoint of any one of the brain images displayed in the stereogram is changed, the viewpoints of all brain images in all rows get changed. FIG. 28 is a diagram for explaining in a concrete manner the operation of changing the viewpoint in the example illustrated in FIG. 27. FIG. 29 is a diagram illustrating another example of the state in which, when the viewpoint of any one of the brain images displayed in the stereogram is changed, the viewpoints of all brain images in all rows get changed. FIG. 30 is a diagram for explaining in a concrete manner the operation of changing the viewpoint in the example illustrated in FIG. 29. FIG. 31 is a diagram illustrating an example of the state in which a comment is added in the stereogram. Explained below with reference to FIGS. 25 to 30 are the operations performed when the viewpoint is changed in a particular stereoscopic image in, the stereogram 612 in the time-frequency analysis is screen 601.

The brain images chat are being displayed as stereoscopic images in the stereogram 612 can subjected to a change in the viewpoint as a result of an operation (such as a dragging operation or a swiping operation) performed by the analyst. Given below is the explanation of a reflection method in which, when the viewpoint of a particular stereoscopic image of the brain is changed in the stereogram 612, the change is reflected in other stereoscopic images.

Firstly, the explanation is given about a case in which, when the viewpoint of a particular stereoscopic image is changed, all other stereoscopic images in the same row are subjected to the same change in the viewpoint. As illustrated at (a) in FIG. 26, in the stereogram 612 having two rows, assume that the analyst performs an operation of changing the viewpoint of the stereoscopic image on the extreme right (hereinafter, sometimes called a "target stereoscopic image") from among the stereoscopic images of the brain displayed in the display area 612-1. In that case, according to the operation performed by the analyst, the stereoscopic display control unit 212 performs viewpoint changing in such a way that the target stereoscopic image, which has the viewpoint from the left lateral of the brain, is displayed as a stereoscopic image having the viewpoint from the dorsal side of the brain as illustrated at (b) in FIG. 26. At that time, the heat map that is overlapping on the images of the brain is also subjected to viewpoint changing in an identical manner. Then, as illustrated at in FIG. 26, with respect to the other stereoscopic images in the same row (the display area 612-1) as the row of the target stereoscopic image, the stereoscopic display control unit 212 implements the same change in the viewpoint as the change implemented with respect to the target stereoscopic image; and displays the stereoscopic images. As a result, by changing the viewpoint of only a particular stereoscopic image (the target stereoscopic image) the same change in the viewpoint gets reflected in the other stereoscopic images of the same row. That leads to an enhancement in the operability, and it becomes easier to check the changes in the activity of the brain before and after in terms of time from the same viewpoint. Meanwhile, as far as the operation for changing the viewpoint of a stereoscopic image is concerned, for example, it is possible to perform a dragging operation or a clicking operation by keeping the mouse on the stereoscopic image for which the viewpoint is to be changed, or it is possible to specify parameters using a popup display.

Given below is explanation of a case in which when the viewpoint of a particular stereoscopic image is changed, all other stereoscopic images are subjected to the same range in the viewpoint. As illustrated at in FIG. 27, in the stereogram 612 having two rows, assume that the analyst performs an operation of changing the viewpoint of the stereoscopic image on the extreme right from among the stereoscopic images of the brain displayed in the display area 612-1. In that case, according to the operation performed by the analyst, the stereoscopic display control unit 212 performs viewpoint changing in such a way that the target stereoscopic image, which has the viewpoint from the left lateral of the brain, is displayed as stereoscopic image having the viewpoint from the dorsal side of the brain as illustrated at (b) in FIG. 27. Then, as illustrated at (c) in FIG. 27, with respect to the other stereoscopic images in the same row (the display area 612-1) as the row of the target stereoscopic image, the stereoscopic display control unit 212 implements the same change in the viewpoint as the change implemented with respect to the target stereoscopic image; and displays the stereoscopic images. That is, regarding the other stereoscopic images in the display area 612-1, the viewpoint from the left lateral of the brain as illustrated at (a) in FIG. 28 is changed to the viewpoint from the dorsal side of the brain as illustrated at (b) in FIG. 28. Moreover, as illustrated at (c) in FIG. 27, also with respect to the stereoscopic images in the other row (the display area 612-2) different than the row of the target stereoscopic image, the stereoscopic control unit 212 implements the same change in the viewpoint as the change implemented with respect to the target stereoscopic image; and displays the stereoscopic images. That is, regarding the stereoscopic images in the display area 612-2 the viewpoint from the right lateral of the brain as illustrated at (a) in FIG. 28 is changed to the viewpoint from the frontal side of the brain as illustrated at (c) in FIG. 28. Meanwhile, if there is some reserve capacity in the processing environment, then the operations illustrated at (a) to in FIG. 28 can be performed at a fast rate, so as to make it appear that the viewpoint or all brain images changing at the same time. However, if the processing environment is poor, the viewpoint is changed only for the image being moved by the user; and, at the timing when the change in the viewpoint is finalized (for example, in the case of changing the viewpoint by rotating a brain image using the dragging operation, the timing when the mouse button is released), the viewpoints of the other images can be changed. At that time, the heat map that is overlapping on the images of the brain is also subjected to viewpoint changing in an identical manner. As a result, by changing the viewpoint or only a particular stereoscopic image (the target stereoscopic image), the same viewpoint changing gets reflected in the other stereoscopic images of the same row as well as in the stereoscopic images of the other row. That leads to an enhancement in the operability, and it becomes easier to check the changes in the activity of the brain before and after in terms of time.

Given below is the explanation of a case in which, when the viewpoint of a particular stereoscopic image is changed, the same change in the viewpoint is implemented in all other stereoscopic images of the same row, and a counterpart change in the viewpoint (more particularly, a change in the viewpoint resulting in plane symmetry with respect to the center plane (target plane) of the brain) is implemented in the stereoscopic images of the other row. As illustrated at (a) in FIG. 29, in the stereogram 612 displayed in two rows, assume that the analyst performs an operation of changing the viewpoint of the stereoscopic image on the extreme right from among the stereoscopic images of the brain displayed in the display area 612-1. In that case, according to the operation performed by the analyst, the stereoscopic display control unit 212 performs viewpoint changing in such a way that the target stereoscopic image, which has the viewpoint from the left lateral of the brain, is displayed as a stereoscopic image having the viewpoint from the left frontal side of the brain as illustrated at (b) in FIG. 29. Then, as illustrated at (c) in FIG. 29, with respect to the other stereoscopic images in the same row (the display area 612-1) as the row of the target stereoscopic image, the stereoscopic display control unit 212 implements the same change in the viewpoint as the change implemented with respect to the target stereoscopic image. That is, regarding the other stereoscopic images in the display area. 612-1, the viewpoint from the left lateral of the brain as illustrated at (a) in FIG. 28 is changed to the viewpoint from the left frontal side of the brain as illustrated at (b) in FIG. 30. Moreover, as illustrated at (c) in FIG. 29, also with respect to the stereoscopic images in the other row (the display area 612-2) different than the row of the target stereoscopic image, the stereoscopic display control unit 212 implements a counterpart change in the viewpoint to the change implemented w respect to the target stereoscopic image; and displays the stereoscopic images. That is, regarding the stereoscopic images in the display area 612-2, the viewpoint from the right lateral of the brain as illustrated at (a) in FIG. 30 is changed to the viewpoint that is in plane symmetry with respect to the center plane (target plane) of the brain, that is, changed to the viewpoint from the right frontal side of the brain as illustrated at (c) in FIG. 30. At that time, the heat map that is overlapping on the images of the brain is also subjected to viewpoint changing in an identical manner. As a result, by changing the viewpoint of only a particular stereoscopic image (the target stereoscopic image), the same change in the viewpoint gets reflected in the other stereoscopic images of the same row and a counterpart change in the viewpoint gets reflected in the stereoscopic images of the other row. That leads to an enhancement in the operability; and, by comparing a plurality of rows, it becomes possible to check the changes in the activity of the brain before and after in terms of time from the counterpart viewpoint.

From among the three reflection methods for reflecting the change in the viewpoint in other stereoscopic images as described above, any one method can be implemented. Alternatively, it can be made possible to switch among the reflection methods using the settings.

In the explanation given above with reference to FIGS. 26 to 30, the stereoscopic image on the extreme right in the display area 612-1 is assumed to be the target stereoscopic image with respect to which the analyst initially performs the operation of changing the viewpoint. However, that is not the only possible case. Alternatively, area any other stereoscopic image in either the display area 612-1 or the display area 612-2 can be treated as the target stereoscopic image. Meanwhile, the stereoscopic images included in the di splay area 612-1 and the stereoscopic images included in the display area 612-2 represent "shape images" or "three-dimensional images" according to the present invention.

The explanation given above is about the operation in which, when the viewpoint of a particular stereoscopic image of the brain changed in the stereogram 612, the change in the viewpoint is reflected in the other stereoscopic images. However, the viewpoint is not the only display aspect that can be changed in a stereoscopic image. Alternatively, display aspects such as expansion/reduction, brightness, or transparency can also be changed. Regarding changes in such display aspects too, the changes can be reflected in the other stereoscopic images without deviating from the purpose explained above with reference to viewpoint changing.

Meanwhile, as described above, the setting can be such that, when a change is made the stereoscopic images displayed in the stereogram 612, the analyst is allowed to write a note regarding a particular stereoscopic image by operating the input, unit 208 as illustrated in FIG. 31 (for example, a comment 635 illustrated in FIG. 31). As a result, regarding the site of the brain showing worrisome activity, the analyst (the doctor) can store a comment in a corresponding manner to the concerned stereoscopic image. That can be useful during the brain surgery, or during a conference held in regard to the disorder in the concerned bran.

<Regarding Head Region Trihedral Figure>

Figure 32:
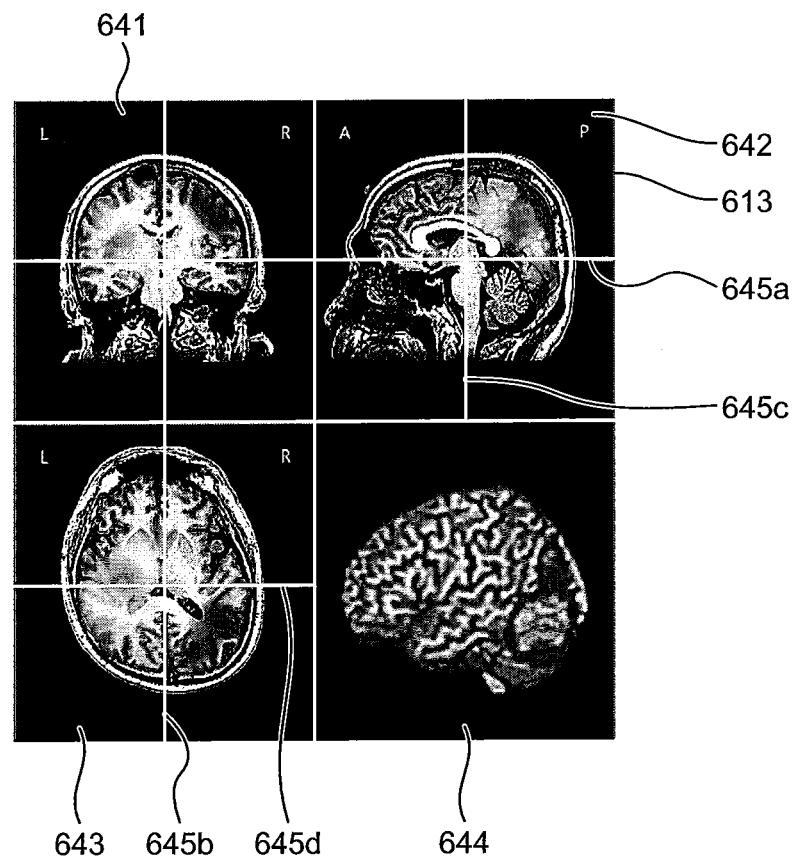
FIG. 32 is a diagram illustrating an example of the head region trihedral figure in the time-frequency analysis screen.
Figure 33:
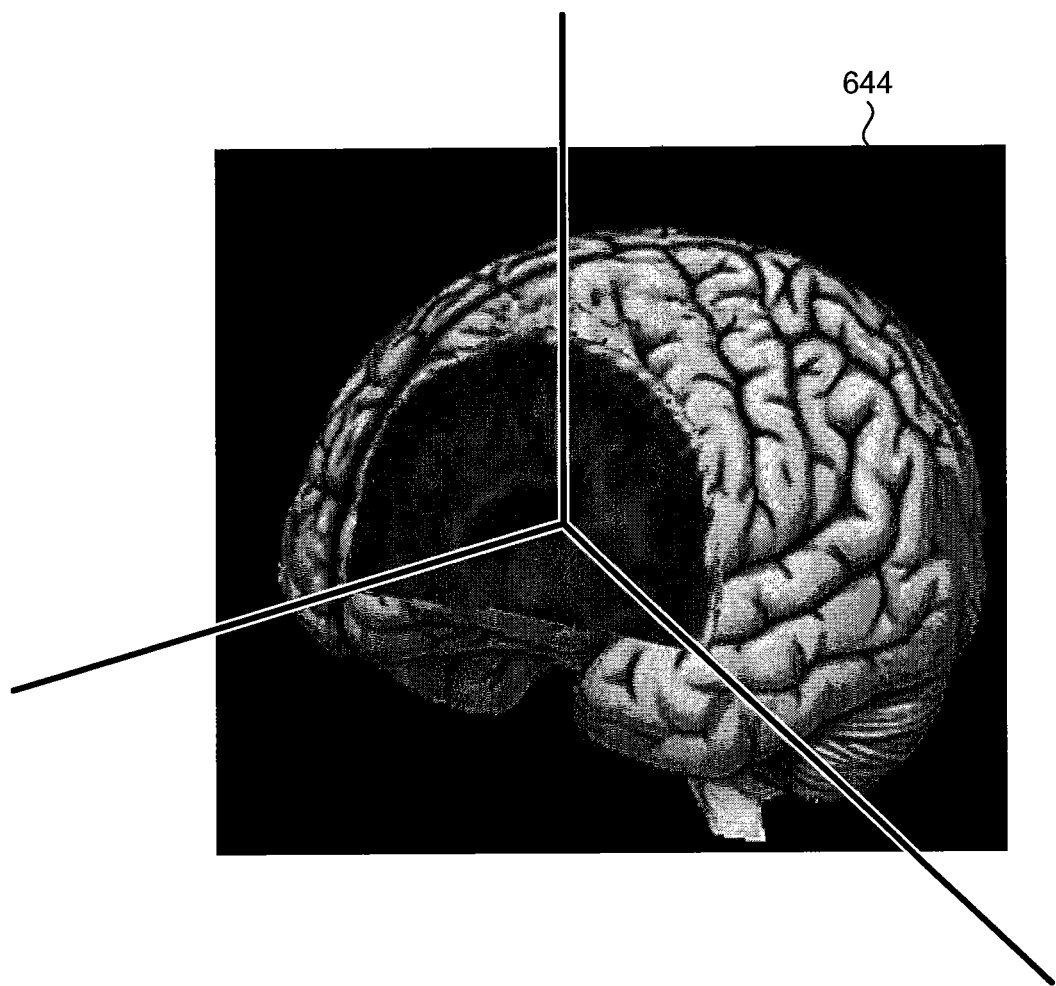
FIG. 33 is a diagram illustrating an example of the state in which a cut model image is displayed as the stereoscopic image in the head portion trihedral figure.
Figure 34:
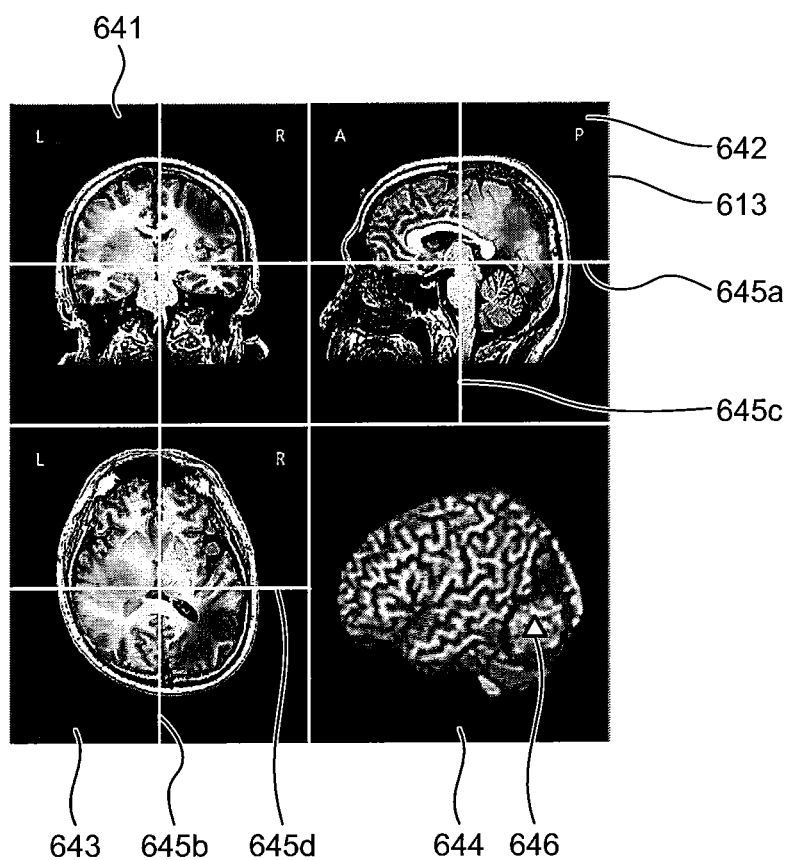
FIG. 34 is a diagram illustrating an example of the state in which the positions of the peaks selected from the peak list are displayed in the head region trihedral figure.
Figure 35:
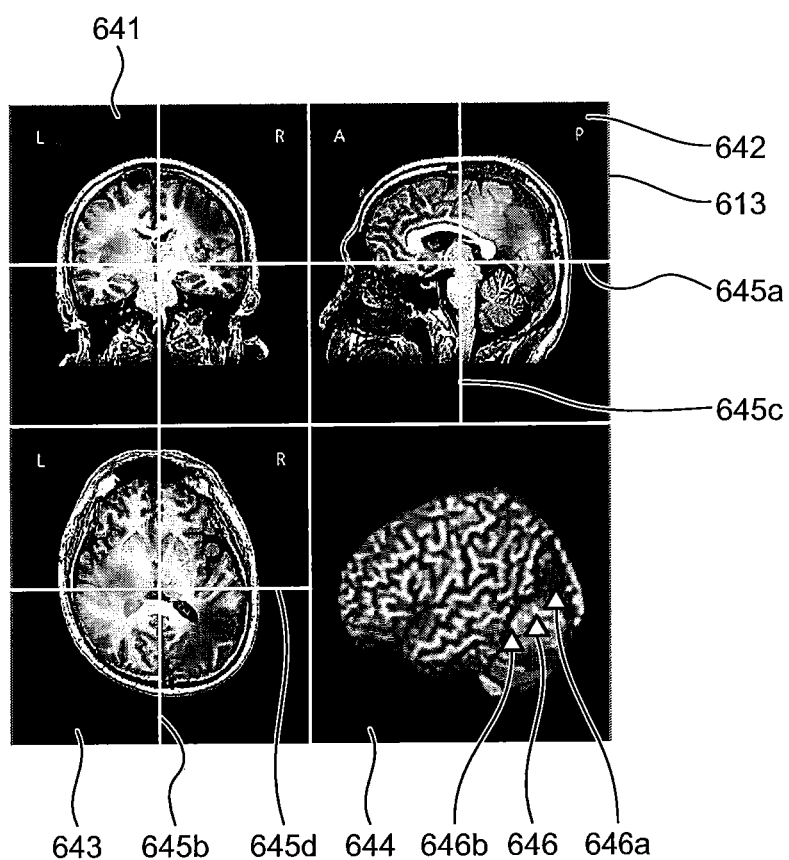
FIG. 35 is a diagram illustrating an example of the state in which the positions of the peaks selected from the peak list and the positions of the peaks present before and after in terms of time are displayed in the head region trihedral figure.
Figure 36:
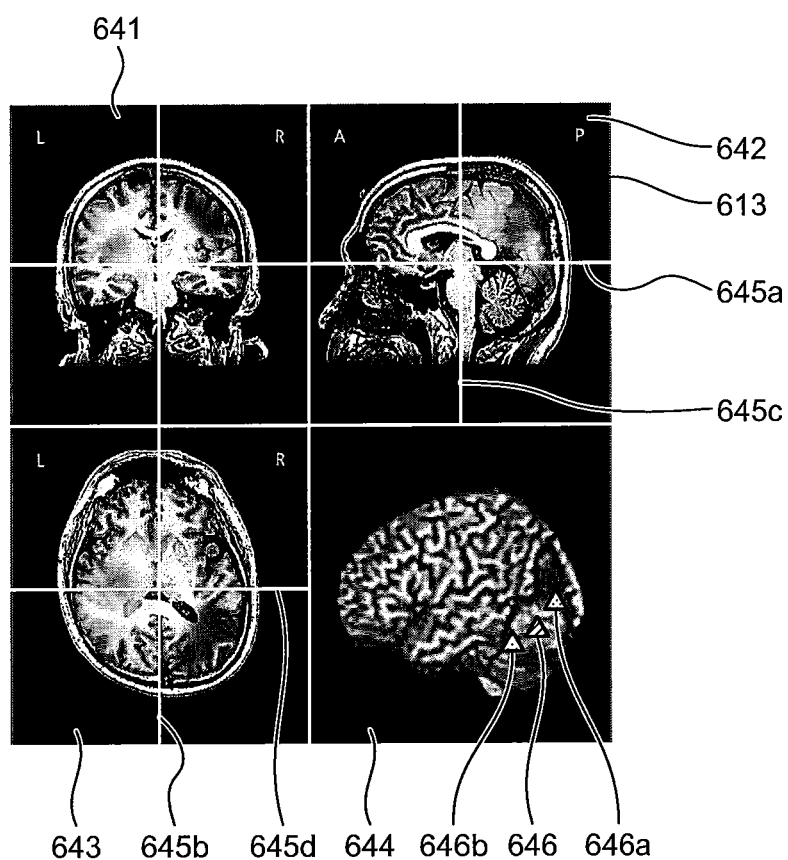
FIG. 36 is a diagram illustrating an example of the state in which the positions of the peaks selected from the peak list and the positions of the peaks present before and after in terms of time are displayed in different colors in the head region trihedral figure.
Figure 37:
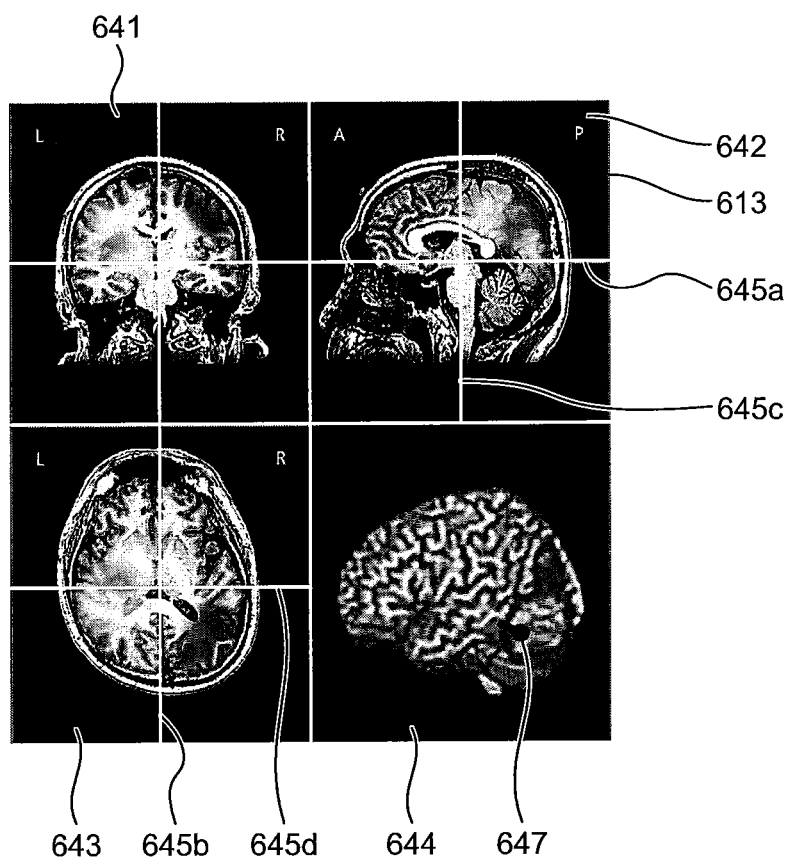
FIG. 37 is a diagram illustrating an example of the state in which the result of dipole estimation is displayed in a superimposed manner on the stereoscopic image in the head region trihedral figure.

FIG. 32 is a diagram illustrating an example of the head region trihedral figure in the time-frequency analysis screen. FIG. 33 is a diagram illustrating an example of the state in which a cut model image is displayed as the stereoscopic image in the head portion trihedral figure. FIG. 34 is a diagram illustrating an example of the state in which the positions of the peaks selected from the peak list are displayed in the head region trihedral figure FIG. 35 is a diagram illustrating an example of the state in which the positions of the peaks selected from the peak list and the positions of the peaks present before and after in terms of time are displayed in the head region trihedral figure. FIG. 36 is a diagram illustrating an example of the state in which the positions of the peaks selected from the peak list and the positions of the peaks present before and after in terms of time are displayed in different colors in the head region trihedral figure. FIG. 37 is a diagram illustrating an example of the state in which the result of dipole estimation is displayed in a superimposed manner on the stereoscopic image in the head region trihedral figure. FIGS. 38A to 38D are diagrams illustrating an example of the state in which the result of a plurality of measurement targets (a heat map) is displayed in a superimposed manner on the stereoscopic image in the head region trihedral figure. Explained below with reference to FIGS. 31 to 37 are explained the fundamental display operations for displaying the head region trihedral figure 613 in the time-frequency analysis screen 601.

As illustrated in FIG. 32, the head region trihedral figure 613 is a diagram including cross-sectional views in three directions at a predetermined position (point) of the brain (hereinafter, sometimes collectively referred to as a "trihedral figure"), and including a stereoscopic image 644 that represents a three-dimensional image. In the example illustrated in FIG. 32, the head region trihedral FIG. 613 includes, as the cross-sectional views in three directions at a particular position of the brain, the following: a cross-sectional view 641 that represents the cross-section perpendicular to the anteroposterior direction of the brain; a cross sectional view 642 that represents the cross-section perpendicular to the crosswise direction of the brain; and a cross-sectional view 643 that represents the cross-section perpendicular to the vertical direction of the brain. The cross-sectional view 641 has reference lines 645a and 645b drawn therein to pass through the particular position. The cross-sectional view 642 has reference lines 645a and 645c drawn therein to pass through the particular position. The cross-sectional view 642 has reference lines 645b and 645d drawn therein to pass through the particular position. On each of the cross-sectional views 641 to 643; a heat map (different than the heat map 611) (a third intensity distribution), which represents the distribution of signal intensities of the biosignals at the time and the frequency corresponding to the position (a point or a range) specified in the heat map 611, is displayed in a superimposed manner. Meanwhile, the operation of displaying the head region trihedral figure 613 is controlled by the cross-section display control unit 213.

The reference line 645a is meant for defining the positions in the vertical direction with reference to the particular position of the brain, and is thus drawn as a continuous line across the cross-sectional views 641 and 642. The reference line 645b is meant for defining the positions in the crosswise direction with reference to the particular position of the brain, and is thus drawn as a continuous line across the cross-sectional views 641 and 643. The reference line 645c is meant for defining the anteroposterior positions with reference to the particular position of the brain in the cross-sectional view 642. The reference line 645d is meant for defining the anteroposterior positions with reference to the particular position of the brain n the cross-sectional view 643. As described above, in the head region trihedral figure 613, the cross-sectional views are arranged as illustrated in FIG. 32 because of the fact that the reference lines 645a and 645b can be drawn as continuous lines across a plurality of cross-sectional views. However, that is not the only possible case, and it is possible to have an arbitrary arrangement. In that case, the reference lines can be drawn to pass through the particular position of the brain in each cross-sectional view. Meanwhile, it is not always necessary to draw the reference lines. Alternatively, in each cross-sectional view, a mark indicating the particular position of the brain can be displayed.

The stereoscopic image 644 is a three-dimensional image of the brain. As described later, according to an operation performed with respect to the stereoscopic image 644, the viewpoint of the stereoscopic images drawn in the stereogram 612 is changed. Moreover, on the stereoscopic image 644; a heat map (different than the heat map 611) (a fourth intensity distribution), which represents the distribution of signal intensities of the biosignals at the time and the frequency corresponding to the specified position (a point or a range) in the heat map 611, is displayed in a superimposed manner. Meanwhile, the stereoscopic image 644 is not limited to be displayed as a stereoscopic image of the particular viewpoint of the brain. Alternatively, for example, as illustrated in FIG. 33, the stereoscopic image 644 can be a cut model image formed by cutting a portion in three-dimensional directions centering around the identified position of the brain, which is identified in the trihedral figure.

In the head region trihedral figure 613 illustrated in FIG. 32, such a trihedral figure is displayed in which the position of each peak selected from among the peaks registered in the peak list 614 is identified. As illustrated in FIG. 34, a peak point 646 indicating the selected peak position can be displayed in the stereoscopic image 644. Alternatively, for example, the positions of N number of upper-level peaks from the peak selected in the peak list 614 can be displayed in the stereoscopic image 644. In FIG. 35 is displayed an example in which the positions of the upper three peaks (peak points 646, 646a, and 646b) are displayed. Alternatively, in FIG. 35, instead of displaying the upper free peak positions, the peak positions at the times before and after the peak selected from the peak list 614 can be displayed as the peak points 646, 646a, and 646b (i.e., the trajectory of the peaks can be displayed. Meanwhile, the manner of displaying the positions of the peaks can be decided depending on the settings. For example, other than the examples given above, it is possible to switch to the setting of not displaying the peaks, or to the setting of displaying the peaks having the signal intensity of M or higher.

Moreover, as illustrated in FIG. 36, regarding a plurality of peaks displayed in the stereoscopic image 644, the display form of the peaks can be varied according to the attribute information thereof. In FIG. 36 is illustrated an example in which the mark is displayed in a different color for each displayed peak.

As illustrated in FIG. 37, the cross-section display control unit 213 displays dipole 647, which represents the result of dipole estimation performed in other analysis screens, in a superimposed manner on the stereoscopic image 644. As a result, it becomes possible to understand the positional relationship between the heat map representing the conservation site indicated by the stereoscopic image 644 and the dipole representing the site of disorder (the target site). That information can be put to use during a surgery.

Meanwhile, the analyst can perform a clicking operation or a tapping operation using the input unit 208 and, in any one cross-sectional view of the trihedral figure, can specify a particular position in the three-dimensional space of the brain. When a particular position in the trihedral figure is specified, the distribution of the signal intensities of the biosignals related to the time and the frequency corresponding to the specified position (point) gets reflected in the heat map 611.

Moreover, the analyst can perform a clicking operation or a tapping operation using the input unit 208 and, in any one cross-sectional view of the trihedral figure, can specify a particular range in the three-dimensional space of the brain. When a particular range in the trihedral figure specified, the distribution of the signal intensities (the average signal intensity in that range) of the biosignals related to the time and the frequency corresponding to the specified position (point) gets reflected in the heat map 611.

Figure 38A:
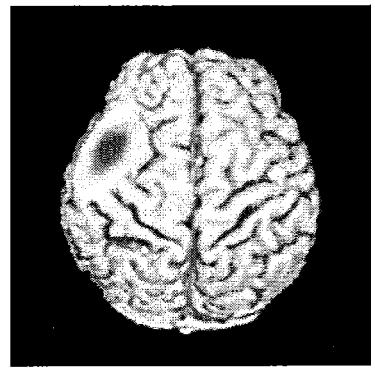
FIGS. 38A to 38D are diagrams illustrating an example of the state in which the result of a plurality of measurement targets (a heat map) is displayed in a superimposed manner on the stereoscopic image in the head region trihedral figure.
Figure 38B:
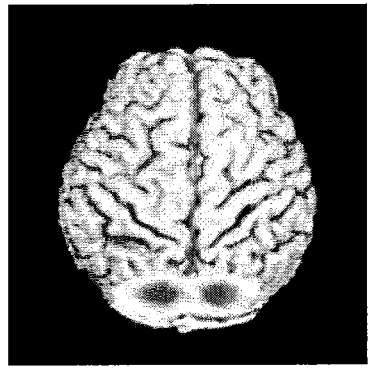
Figure 38C:
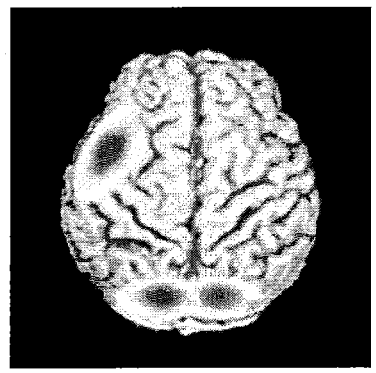
Figure 38D:
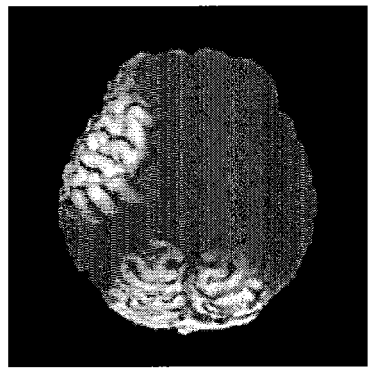

The heat map (a contour map indicating the levels or intensities) drawn in the stereoscopic image 644 (and the trihedral figure) can be used to display, in a superimposed manner, the result of stimulation given so as to ensure that there is more activity of each site of the brain. For example, after obtaining the result of giving verbal stimulation (during measurement) with respect to the signals and after obtaining the result of giving visual stimulation (during measurement) with respect to the signals, the cross-section display control unit 213 can display, in a superimposed manner as illustrated at (c) in FIG. 38C, the heat map obtained as a result of stimulating the speech area as illustrated in FIG. 38A and the heat map obtained as a result of stimulating the visual area as illustrated in FIG. 38B. Thus, the sites represented by the heat map, which is displayed in a superimposed manner as illustrated in FIG. 38C, can be confirmed to be the conservation sites. As far as the operation method for superimposition is concerned, if the currently-displayed measurement result is about the speech area, a different measurement result (for example, about the visual area) can be made selectable using a menu. Meanwhile, at the time of superimposition, the response time by the measurement target width respect to the stimulation may differ. In that regard, if it is made possible to set a time lag in the case of adding a measurement target, the superimposition can be done in a more appropriate manner. Moreover, if the stereoscopic image that represents the result of superimposing the heat map as illustrated in FIG. 38C is reverse-displayed as illustrated in FIG. 38D, then it conversely becomes possible to indicate the excisable sites not representing the conservation sites.

The cross-sectional views in the head region trihedral figure 613 represent a trihedral figure having three cross-sectional views in three different cross-sectional directions. However, that is not the only possible case. Alternatively, there can be a cross-sectional view in one particular cross-sectional direction, or there can be cross-sectional views in two different cross-sectional directions, or there can be cross-sectional views in four or more different cross-sectional directions.

Figure 39:
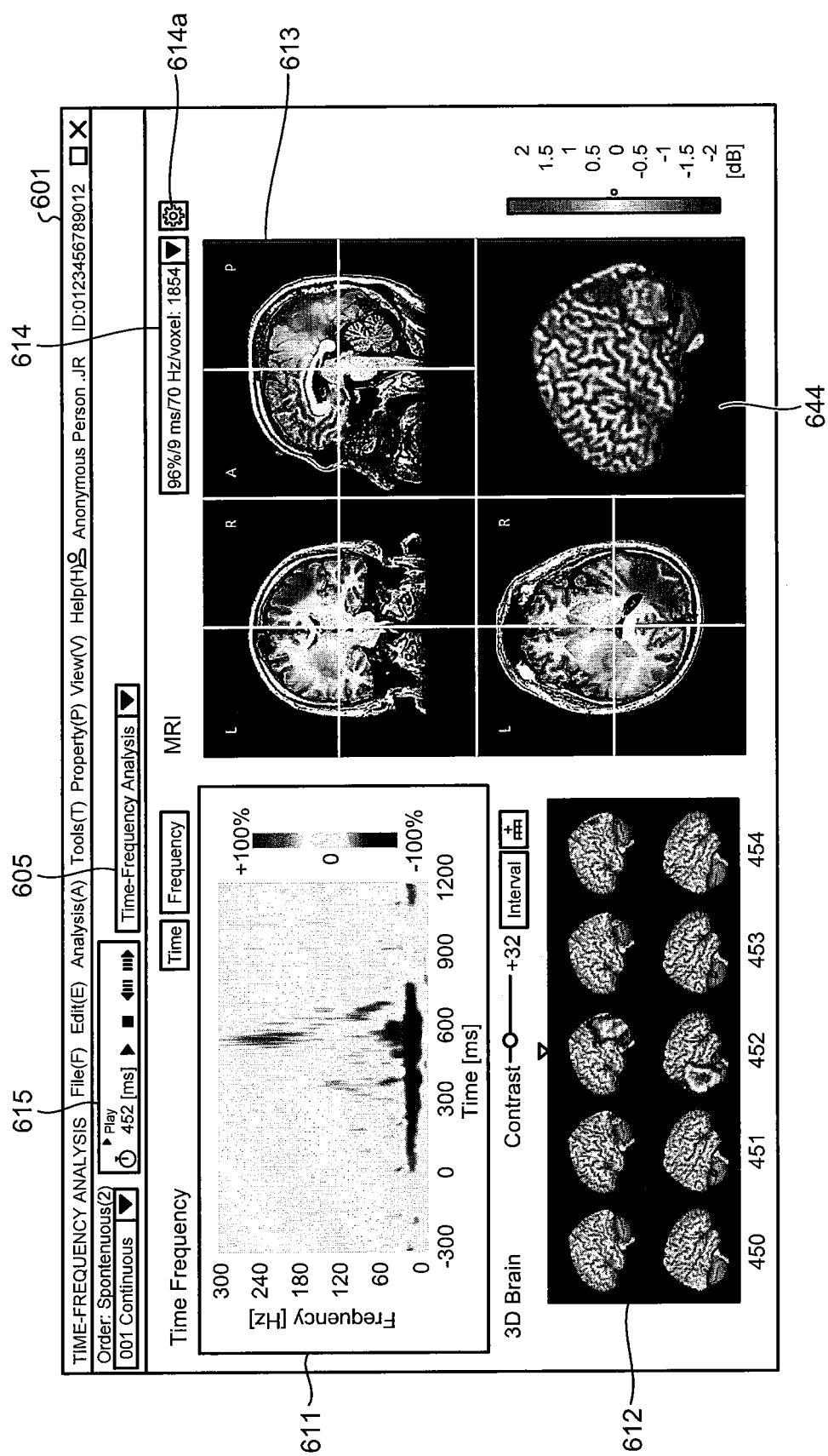
FIG. 39 is a diagram indicating an example of the state before making a change in the viewpoint of the stereoscopic image in the head region trihedral figure.
Figure 40:
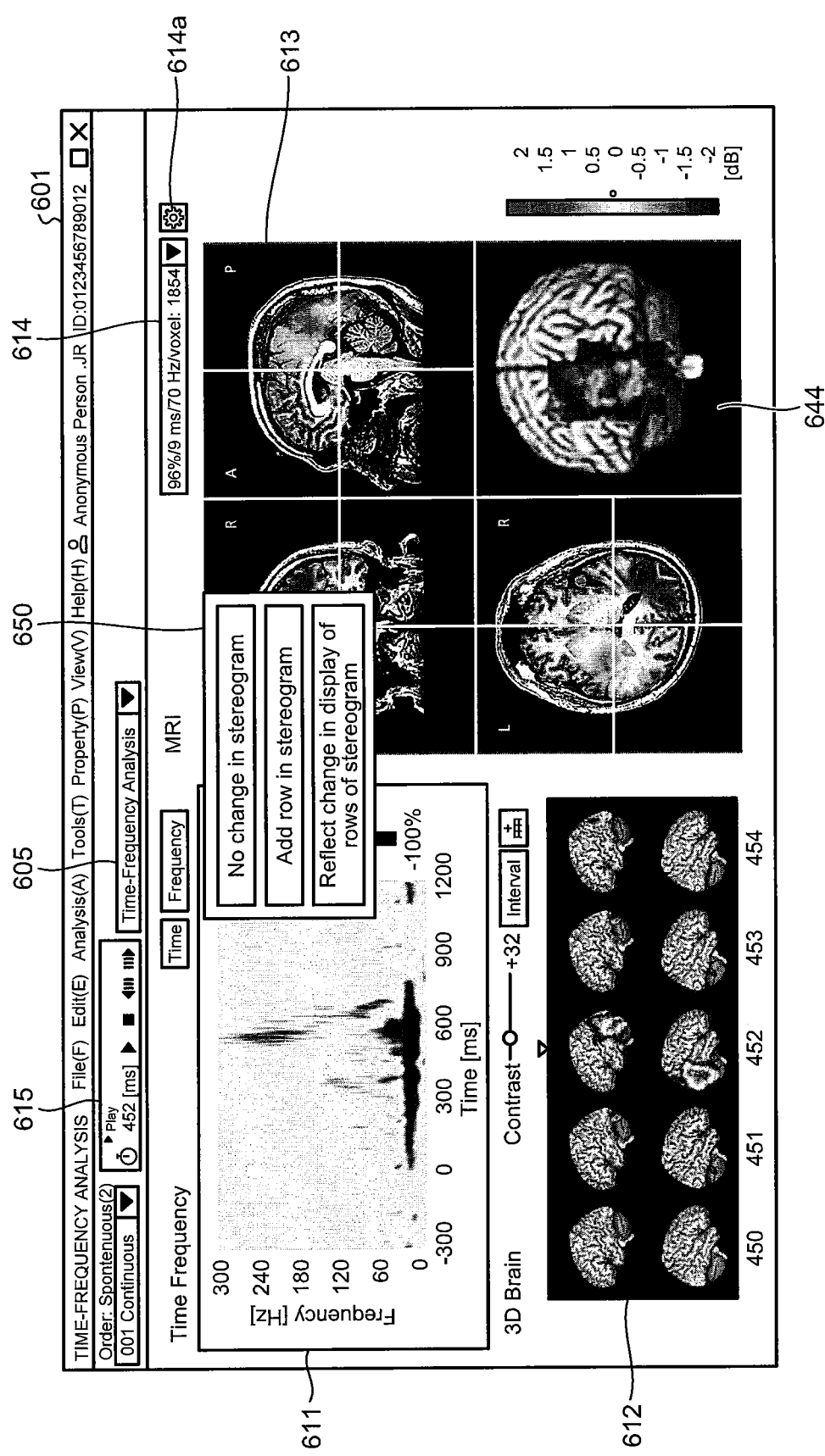
FIG. 40 is a diagram illustrating a dialog box that is displayed when the viewpoint of the stereoscopic image in the head region trihedral figure is changed.
Figure 41:
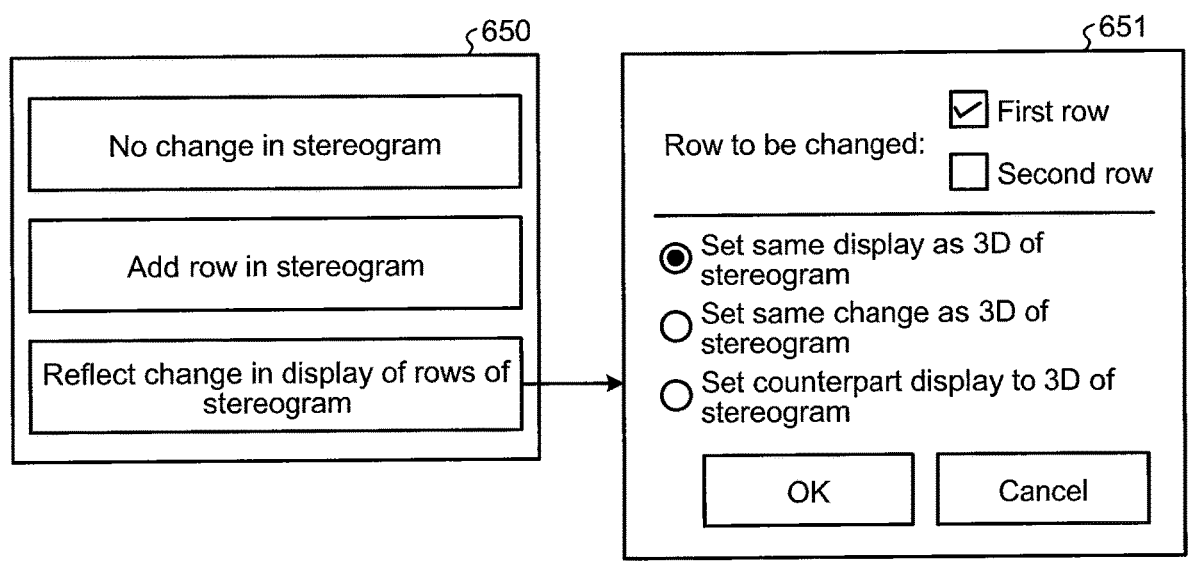
FIG. 41 is a diagram illustrating an example of the setting that, in response to a change in the viewpoint of stereoscopic image, enables reflection of the same display in the first row of the stereogram.
Figure 42:
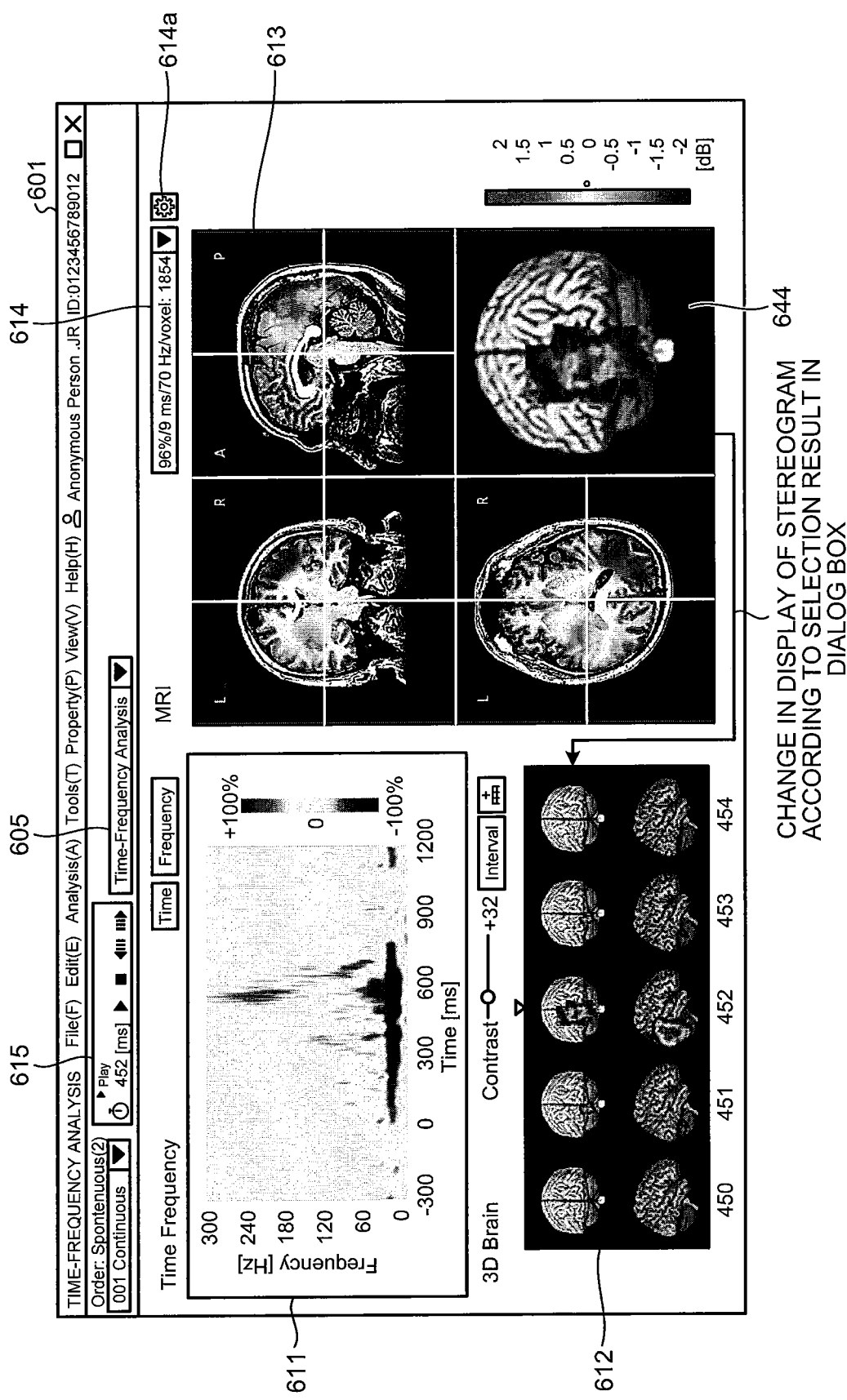
FIG. 42 is a diagram illustrating the state in which, when the viewpoint of the stereoscopic image in the head region trihedral figure is changed, the same display is reflected in the first row of the stereogram.
Figure 43:
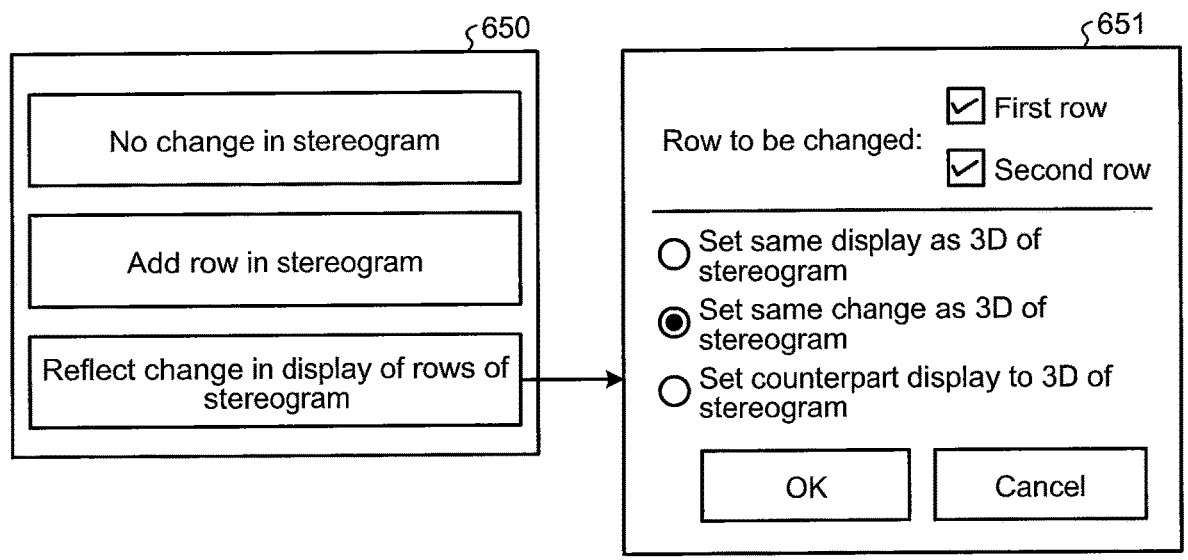
FIG. 43 is a diagram illustrating an example of the setting that, in response to a change in the viewpoint of a stereoscopic image, enables reflection of the same change in the first and second rows of the stereogram.
Figure 44:
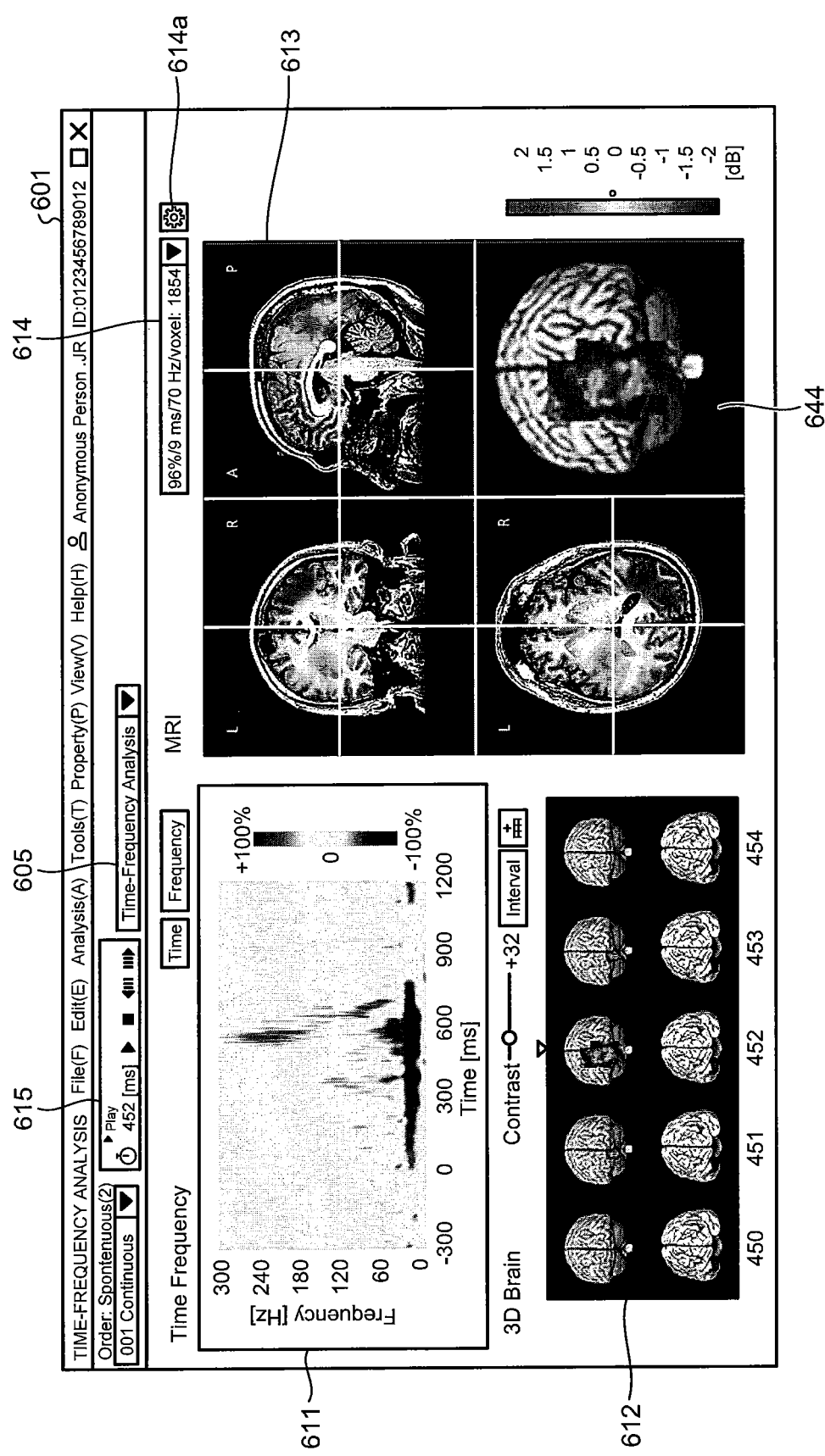
FIG. 44 is a diagram illustrating the state in which, when the viewpoint of the stereoscopic image in the head region trihedral figure is changed, the same display is reflected in the first and second rows of the stereogram.
Figure 45:
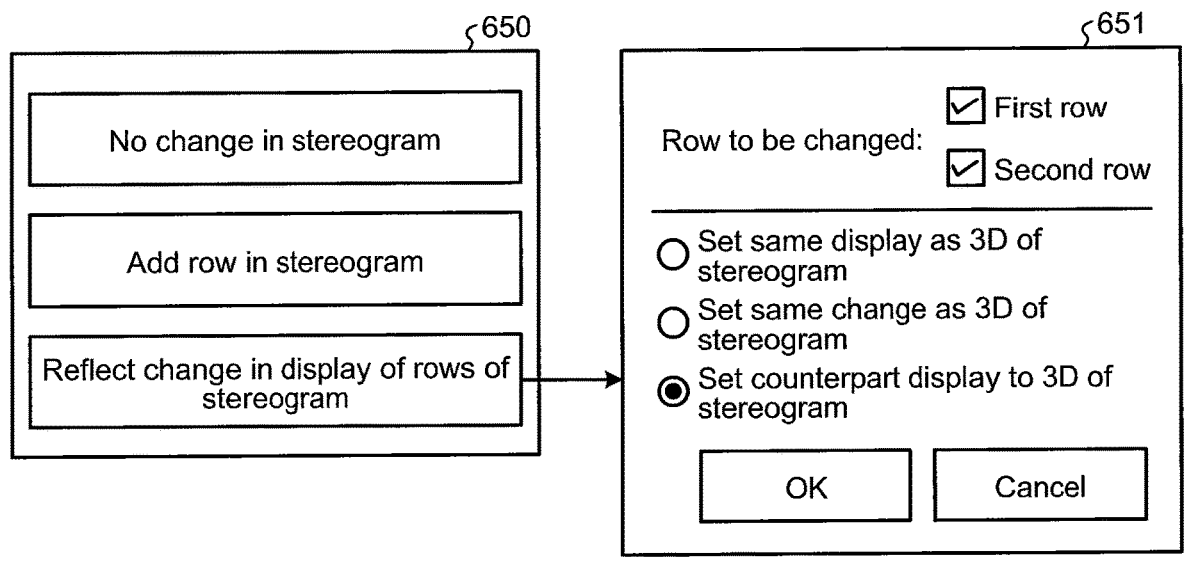
FIG. 45 is a diagram illustrating an example of the setting that, in response to a change in the viewpoint of a stereoscopic image, enables reflection of the counterpart change in the first and second rows of the stereogram.
Figure 46:
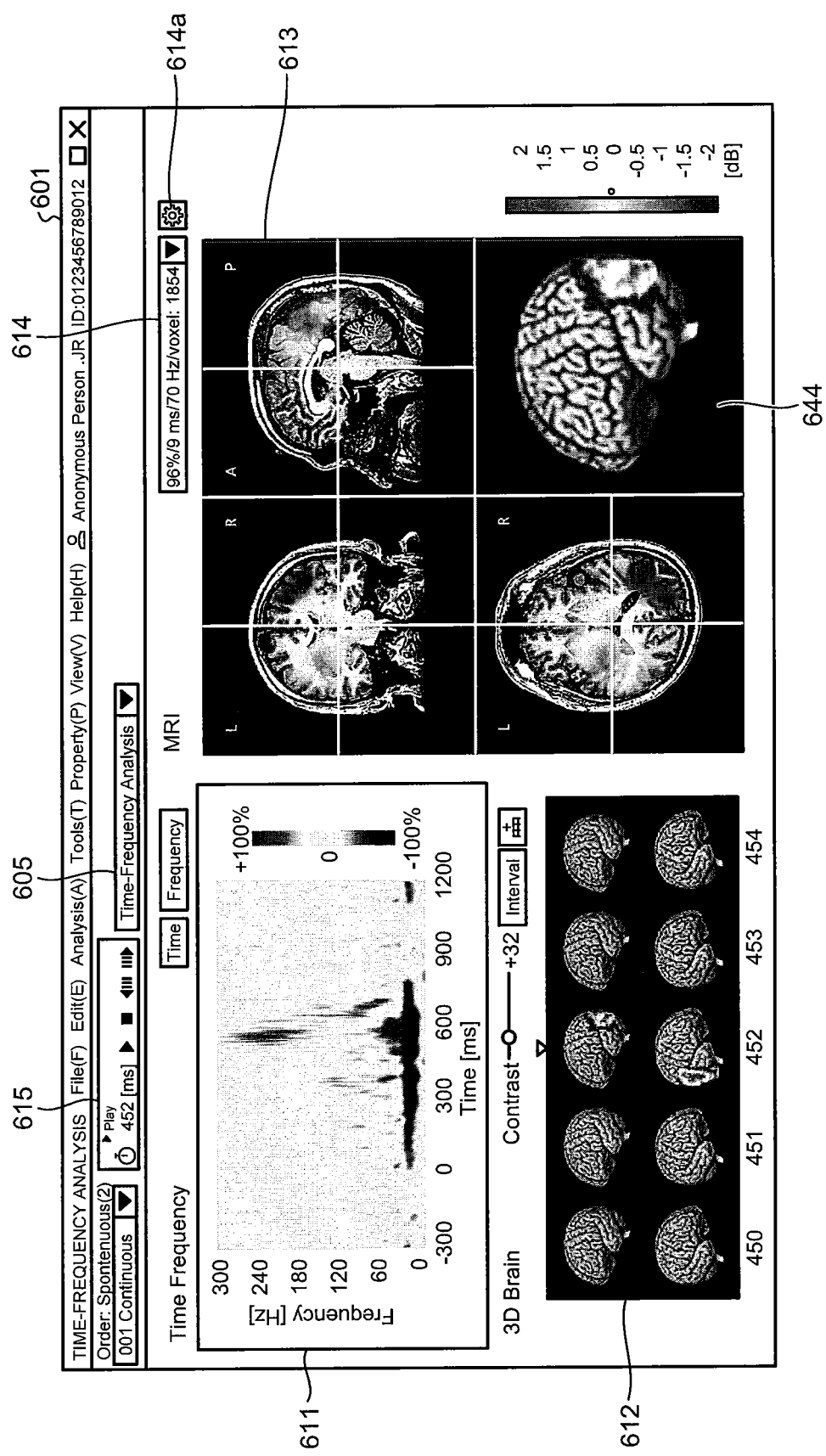
FIG. 46 is a diagram illustrating the state in which, when the viewpoint of the stereoscopic image in the head region trihedral figure is changed, the counterpart change is reflected in the first and second rows of the stereogram.
Figure 47:
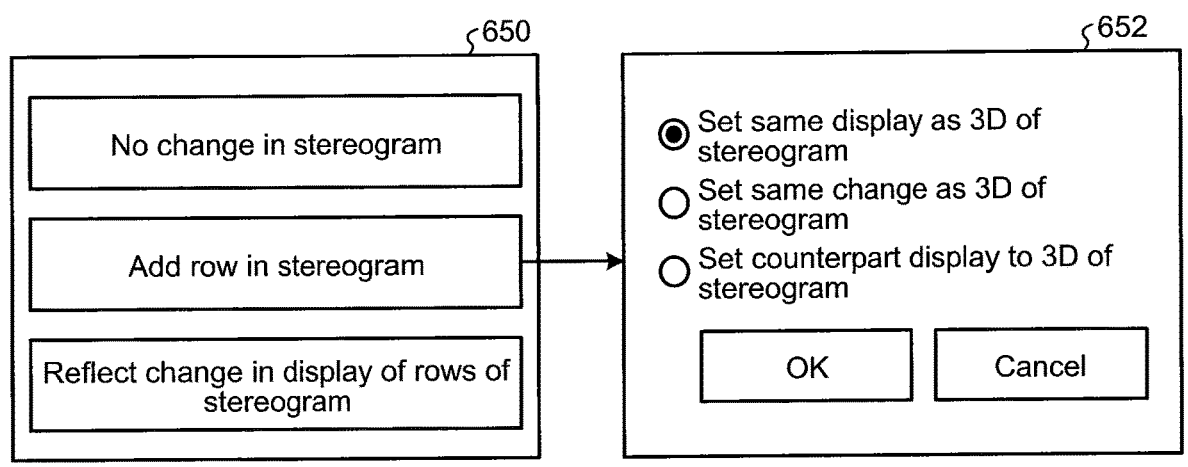
FIG. 47 is a diagram illustrating an example of the setting that, in response to a change in the viewpoint of a stereoscopic image, enables addition of a new row of the same display in the stereogram.
Figure 48:
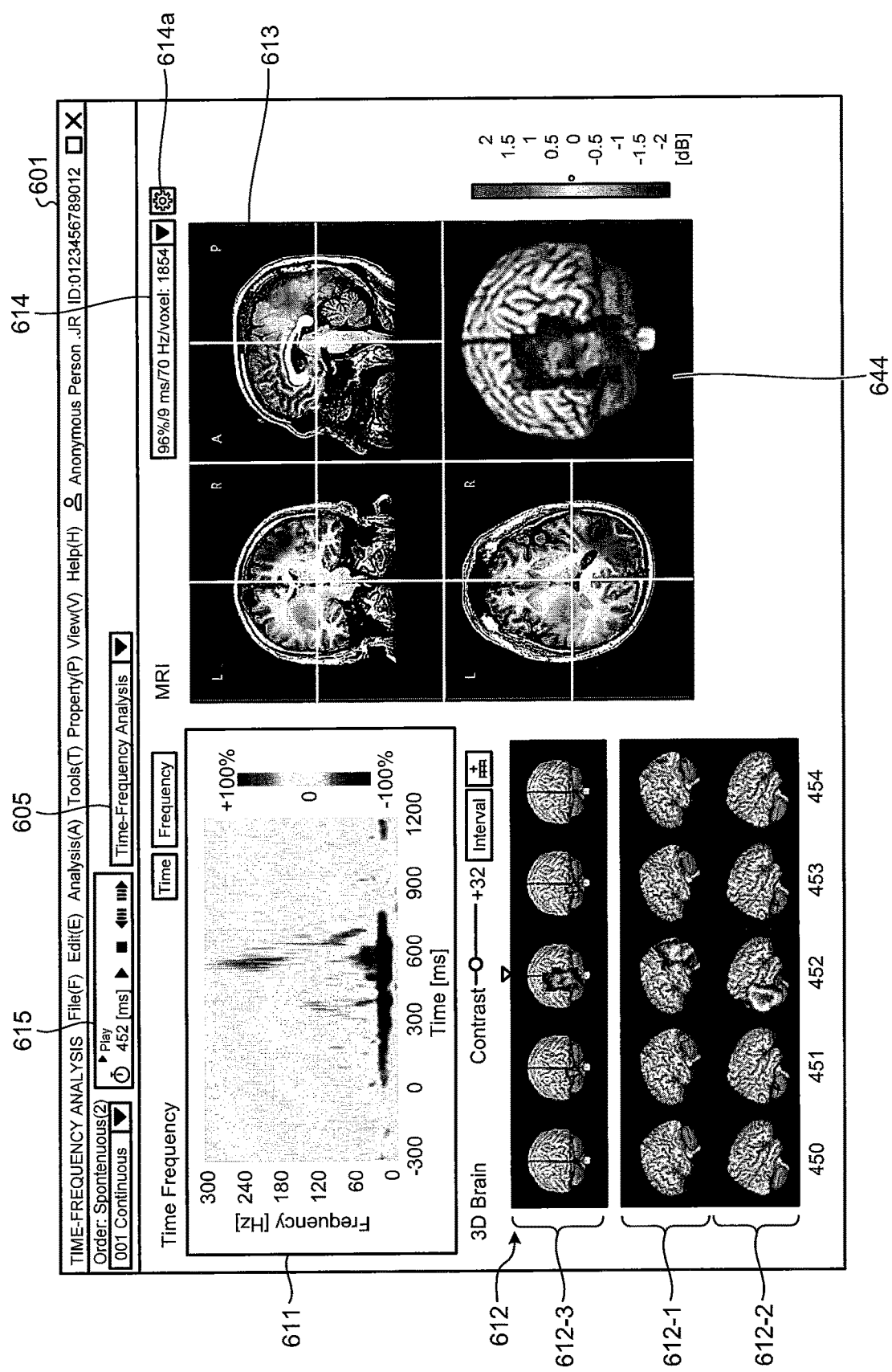
FIG. 48 is a diagram illustrating the state in which, when the viewpoint of the stereoscopic image in the head region trihedral figure is changed, a new row of the same display is added in the stereogram.

FIG. 39 is a diagram indicating an example of the state before making a change in the viewpoint of the stereoscopic image in the head region trihedral figure. FIG. 40 is a diagram illustrating a dialog box that is displayed when the viewpoint of the stereoscopic image in the head region trihedral figure is changed. FIG. 41 is a diagram illustrating an example of the setting that, in response to a change in the viewpoint of a stereoscopic image, enables reflection of the same display in the first row of the stereogram. FIG. 42 is a diagram illustrating the state in which, when the viewpoint of the stereoscopic image in the head region trihedral figure is changed, the same display is reflected in the first row of the stereogram. FIG. 43 is a diagram illustrating an example of the setting that, in response to a change in the viewpoint of a stereoscopic image, enables reflection of the same change in the first and second rows of the stereogram. FIG. 44 is a diagram illustrating the state in which, when the viewpoint of the stereoscopic image in the head region trihedral figure is changed, the same display is reflected in the first and second rows of the stereogram, FIG. 45 is a diagram illustrating an example of the setting that, in response to a change in the viewpoint of a stereoscopic image, enables reflection of the counterpart change in the first and second rows of the stereogram. FIG. 46 is a diagram illustrating the state in which, when the viewpoint of the stereoscopic image in the head region trihedral figure is changed, the counterpart change is reflected in the first and second rows of the stereogram. FIG. 47 is a diagram illustrating an example of the setting that, in response to a change in the viewpoint of a stereoscopic image, enables addition of a new row of the same display in the stereogram. FIG. 48 is a diagram illustrating the state in which, when the viewpoint of the stereoscopic image in the head region trihedral figure is changed, a new row of the same display is added in the stereogram. Explained below with reference to FIGS. 38 to 47 are the operations in which, when there is a change in the viewpoint of the stereoscopic image in the head region trihedral figure 613 of the time-frequency analysis screen 601, the change in the viewpoint is reflected in the stereogram 612.

The brain visible in the stereoscopic image 644 of the head region trihedral figure 613 can be subjected to a change in the viewpoint in an identical manner to the stereogram 612 as a result of an operation (for example, a dragging operation or a swiping operation) performed by the analyst. In that case, when the viewpoint of the brain is changed in the stereoscopic image 644, the change can be reflected in the viewpoint of the brain displayed in the stereogram 612. Given below is the explanation of a reflection method for reflecting the change.

When the analyst performs an operation (such as a dragging operation or a swipe operation) with respect to the stereoscopic image 644 of the head region trihedral figure 613 displayed in the time-frequency analysis screen 601 as illustrated in FIG. 39, the cross-section display control unit 213 displays a dialog box 650 as illustrated in FIG. 40. The dialog box 650 is a screen that, when there is a change in the viewpoint of the brain displayed in the stereoscopic image 644, enables decision on the manner of reflecting the change in the stereogram 612. For example, if a "no change in stereogram" button is pressed, then the viewpoint of the stereographic images in the stereogram 612 is not changed. Herein, as illustrated in FIG. 40, it is assumed that the analyst changes the viewpoint in such a way that the stereoscopic image 644, which has the viewpoint from the left lateral of the brain, is displayed as a stereoscopic image having the viewpoint from the dorsal side of brain.

Firstly, illustrated in FIG. 41, assume that a "reflect change in di y of rows of stereogram" button pressed. The as illustrated in FIG. 41, the cross-section display control unit 213 displays a dialog box 651 meant for setting the details regarding the manner of reflecting the change in the stereogram 612. As Illustrated in FIG. 41, in the dialog box 651, assume that the analyst selects the first row of the stereogram 612 as the row to be changed and selects "set same display as 3D of stereogram". In that case, as illustrated in FIG. 42, the stereoscopic display control unit 212 displays the stereoscopic images in the first row (the upper row) of the stereogram 612 from the same viewpoint as the changed viewpoint of the stereoscopic image 644.

Subsequently, from the state of the changed viewpoint as illustrated in FIG. 40; assume that the analyst presses the "reflect change in display of rows of stereogram" button in the dialog box 650, selects the first and second rows of the stereogram 612 as the rows to be changed in the dialog box 651, and selects "set same display as 3D of stereogram" as illustrated in FIG. 43. In that case, as illustrated in FIG. 44, with respect to the stereoscopic images in the first row of the stereogram 612 that originally had the same viewpoint as the stereoscopic image 644, the stereoscopic display control unit 212 changes the viewpoint to be same as the changed viewpoint of the stereoscopic image 644, and then displays the stereoscopic images in the first row of the stereogram 612. That is, as illustrated in FIG. 44, the view point is changed to the viewpoint from the dorsal side of the brain. Moreover, as illustrated in FIG. 44, with respect to the stereoscopic images in the second row of the stereogram 612 that originally had the viewpoint from the right lateral of the brain, the stereoscopic display control unit 212 changes the viewpoint to be same as the changed viewpoint of the stereoscopic image 644, and then displays the stereoscopic images in the second row of the stereogram 612. That as illustrated in FIG. 44, the viewpoint changed to the viewpoint from the frontal side of the brain.

The selection in dialog box 651 following the press of the [Reflect change in display of rows of stereogram] button may be initially set or be enabled to be initially set, and then a [link of views] button/a [unlink of views] button may provided to enable to display the selection result. According to this configuration, is possible to omit (simplify) the selection operation repeated every time.

Subsequently as illustrated in FIG. 46, assume that the arranges the viewpoint in such a way that the stereoscopic image 644, which has the viewpoint from the left lateral of the brain, is displayed as a stereoscopic image having the viewpoint from the left frontal side of the brain. Then, from this state, as illustrated in FIG. 45, assume that the analyst presses the "reflect change in display of rows of stereogram" button in the dialog box 650, selects the first and second rows of the stereogram 612 as the rows to be changed in the dialog box 651, and selects "set same display as 3D of stereogram". In that case, as illustrated in FIG. 46, with respect to the stereoscopic images in the first row of the stereogram 612 that originally had the same viewpoint as the stereoscopic image 644, the stereoscopic display control unit 212 changes the viewpoint to be same as the changed viewpoint of the stereoscopic image 644, and then displays the stereoscopic images in the first row of the stereogram 612. That is, as illustrated in FIG. 46, the viewpoint is changed to the viewpoint from the left frontal side of the brain. Moreover, as illustrated in FIG. 46, with respect to the stereoscopic images in the second row of the stereogram 612 that originally had the viewpoint from the right lateral of the brain, the stereoscopic display control unit 212 changes the viewpoint to be a counterpart of the changed viewpoint of the stereoscopic image 644, and then displays the stereoscopic images in the second row of the stereogram 612. That is, as illustrated in FIG. 46, the viewpoint is changed to the viewpoint that is in plan symmetry with respect to the center plane (target plane) of the brain, that is, to the viewpoint from the right frontal side of the brain.

Subsequently, from the state of the changed viewpoint as illustrated in FIG. 40, assume that the analyst presses an "add row in stereogram" in the dialog box 650 and selects "set same display 3D of stereogram" in a dialog box 652 that gets displayed as illustrated in FIG. 47. In that case, as illustrated in FIG. 48, as a result of the change in the viewpoint of the stereoscopic image 644, the stereoscopic display control unit 212 displays, as a new row in a display area 612-3 of the stereogram 612, stereoscopic images of the brain having the same viewpoint. That as illustrated in FIG. 48, stereoscopic images having the viewpoint from the dorsal side of the brain are displayed in the new row in the display area 612-3.

As described above, the change in the viewpoint of the stereoscopic image 644 in the head region trihedral figure 613 can be reflected, according to various settings, in the viewpoint of the stereoscopic images of the brain that are arranged in chronological order in the stereogram 612. As a result, the change in the viewpoint of the stereoscopic image 644 need not be again implemented with respect to the stereogram 612. That leads to an enhancement in the operability, and the changes in the state of the brain can be checked in chronological order in the stereogram 612 from either the identical viewpoint or the counterpart viewpoint to the changed viewpoint of the stereoscopic image 644.

Meanwhile, the reflection method for reflecting the viewpoint of the brain images displayed in the stereogram 612 as set using the dialog boxes 650 to 652 illustrated in FIGS. 40, 42, 44, and 46 is only exemplary; and some other reflection method can also be implemented.

The explanation given above is about the operation in which, when the viewpoint of the stereoscopic image 644 is changed, the change in the viewpoint is reflected in the stereoscopic images in the stereogram 612. However, the viewpoint is not the only display aspect that can be changed in the stereoscopic image 644. Alternatively, display aspects such as expansion/reduction, brightness, or transparency can also be changed. Regarding changes in such display aspects too, the changes can be reflected in the stereoscopic images in the stereogram 612 without deviating from the purpose explained above with reference to viewpoint changing.

<Regarding Peak List>

Figure 49:
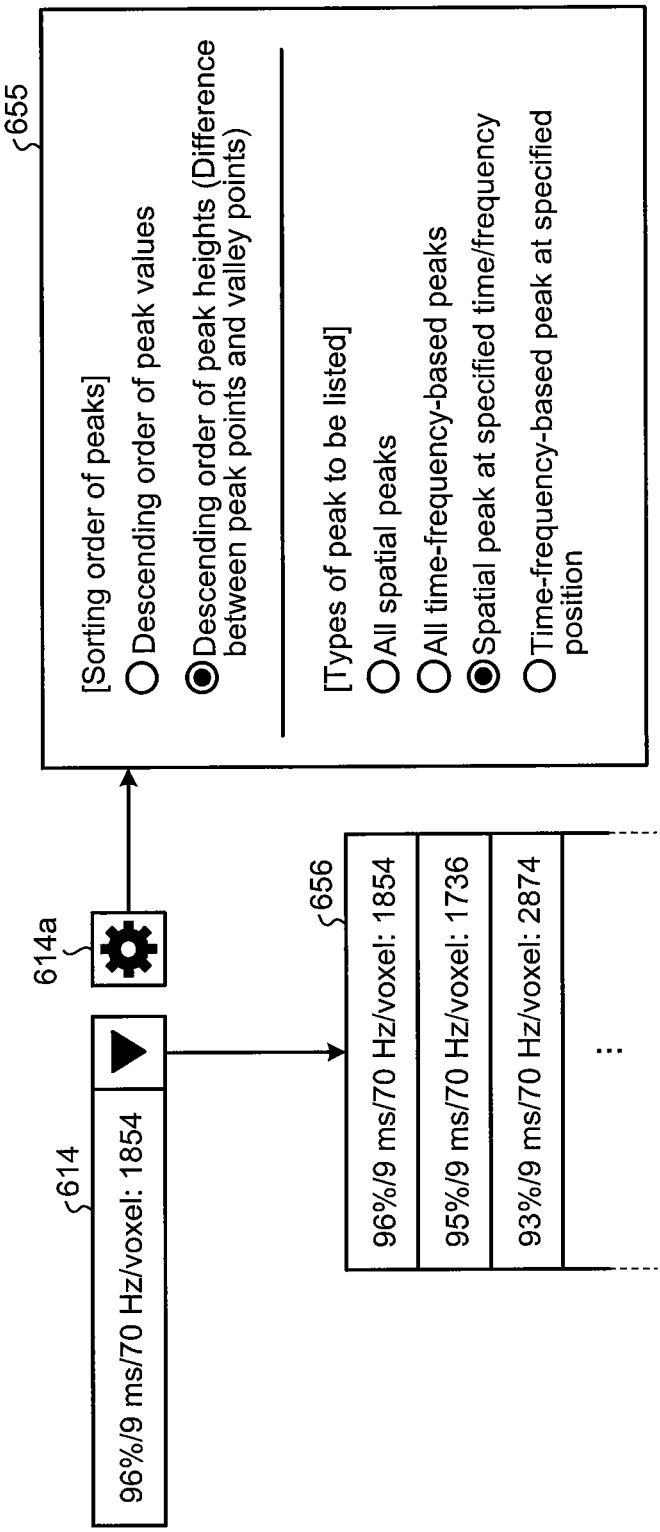
FIG. 49 is a diagram illustrating an example of the setting of the peak list.
Figure 50:
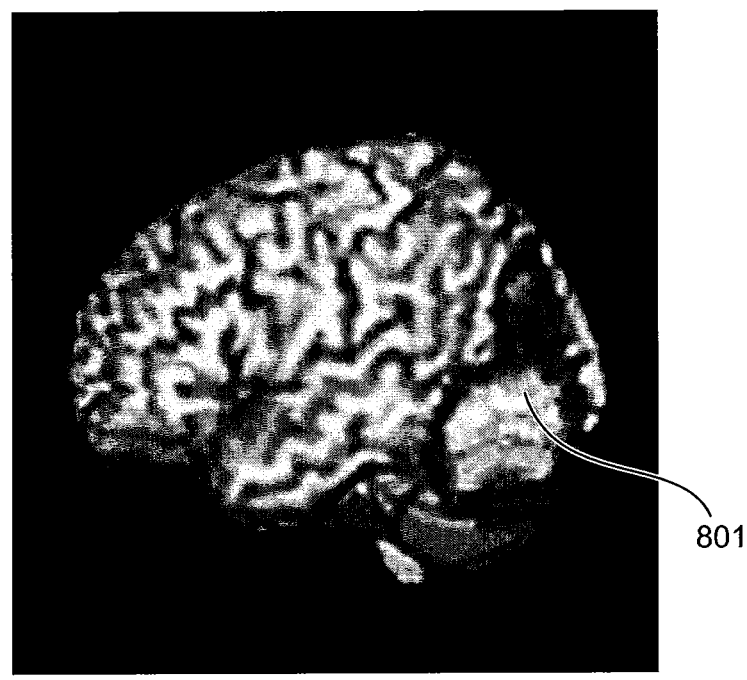
FIG. 50 is a diagram for explaining a spatial peak.
Figure 51:
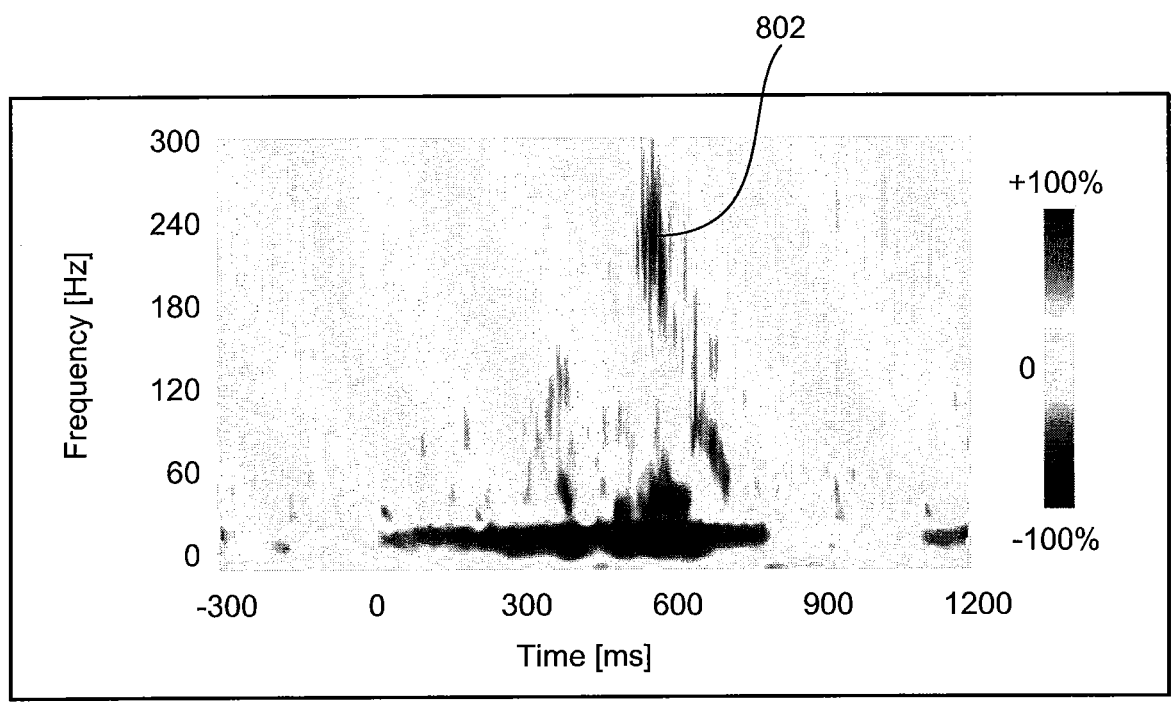
FIG. 51 is a diagram for explaining a time-frequency-based peak.
Figure 52:
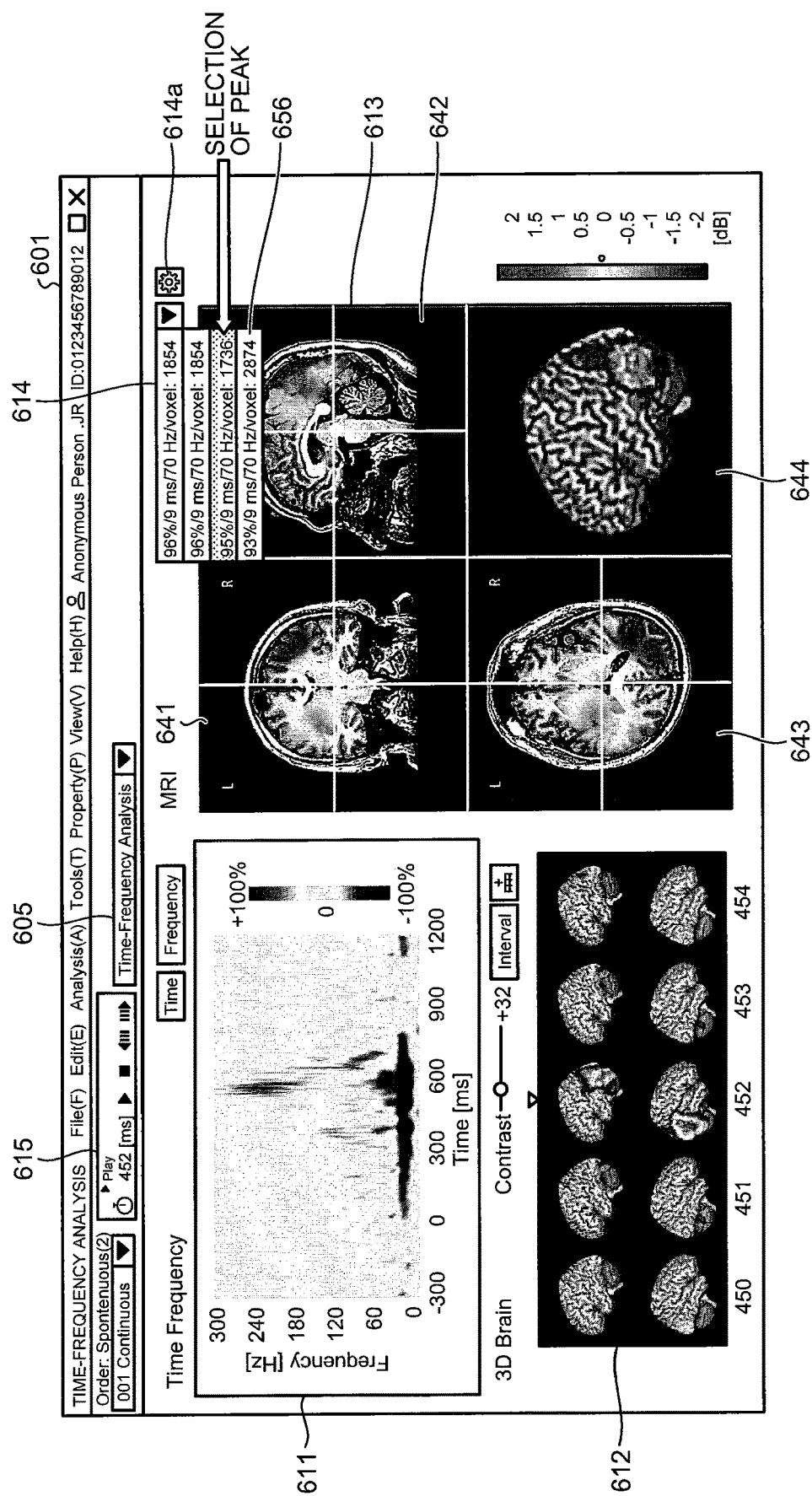
FIG. 52 is a diagram illustrating the state in which a particular peak is selected from a peak list in the pulled-down state.
Figure 53:
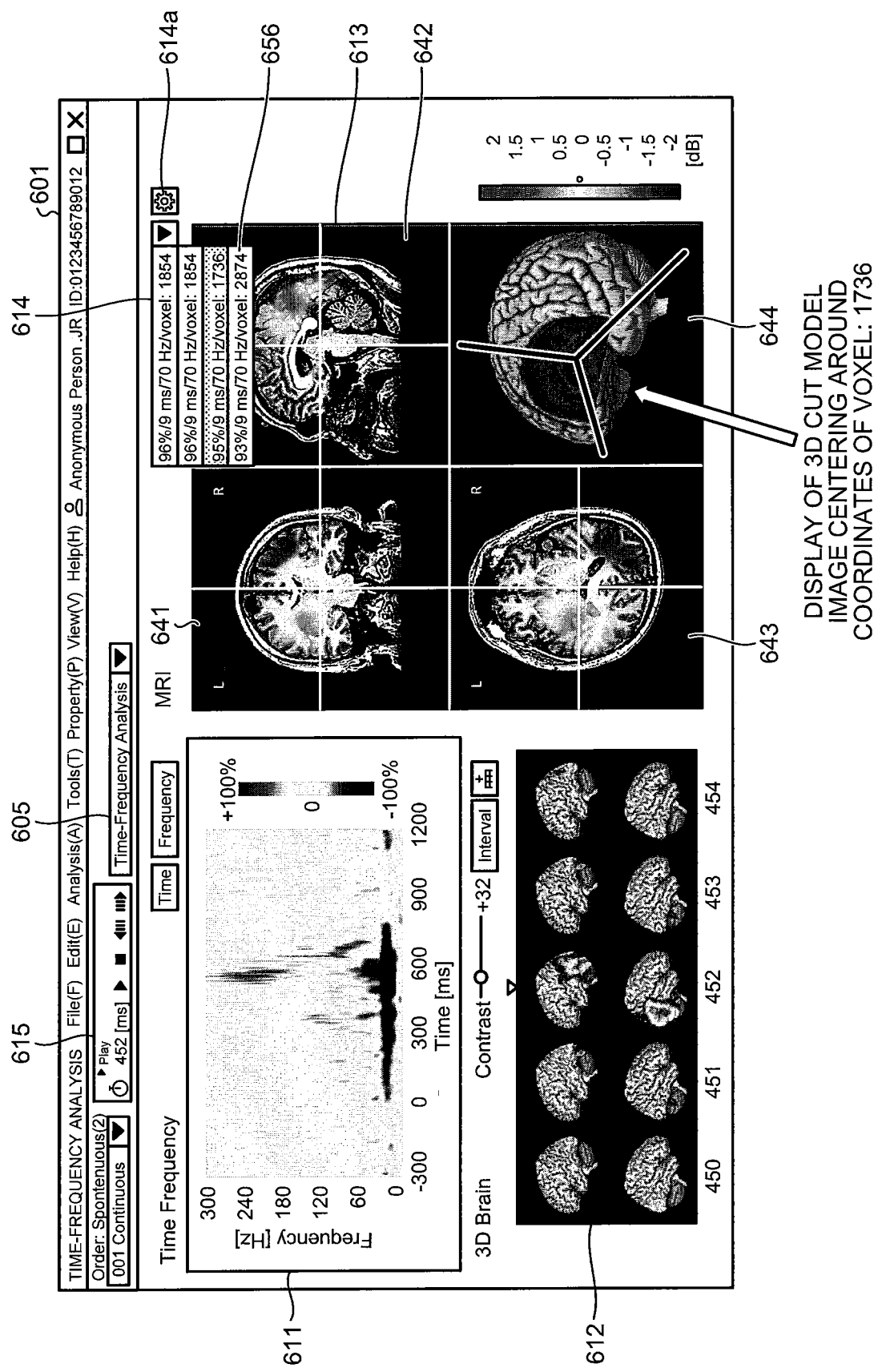
FIG. 53 is a diagram illustrating the state of reflection in the heat map, the stereogram, and the head region trihedral figure regarding the peak selected from the peak list in the pulled-down state.

FIG. 49 is a diagram illustrating an example of the setting of the peak list. FIG. 50 is a diagram for explaining a spatial peak. FIG. 51 is a diagram for explaining a time-frequency-based peak. FIG. 52 is a diagram illustrating the state in which a particular peak is selected from a peak list in the pulled-down state. FIG. 53 is a diagram illustrating the state of reflection in the heat map, the stereogram, and the head region trihedral figure regarding the peak selected from the peak list in the pulled-down state. Explained below with reference to FIGS. 48 to 52 are the fundamental operations regarding the peak list 614 in the time-frequency analysis screen 601.

The peak list 614 is a list for registering the peaks of signal intensities that are extracted by the peak list control unit 203 and that satisfy set conditions. As illustrated in FIG. 49, the peak list control unit 203 displays a pull-down list 656 that represents a list of signal intensities registered in the peak list 614 as a result of a pull-down operation.

The conditions for the peaks of the signal intensities as extracted by the peak list control unit 203 can be set by pressing the peak list setting button 614a. When the peak list setting button 614a is pressed, the peak list control unit 203 displays a dialog box 655 meant for setting the conditions for the to-be-extracted peaks of intensities.

In the dialog box 655, firstly, it is possible to set the manner of sorting the peak information registered in the peak list 614. In the dialog box 655, if "descending order of peak values" is selected, then the peak list control unit 203 sorts the sets of peak information, which are registered in the peak list 614, in descending order of the signal intensities of the peaks. On the other hand, in the dialog box 655, if "descending order of peak heights (difference between peak points and valley points)" is selected, then the peak list control unit 203 sorts the sets of peak information, which are registered in the peak list 614, in descending order of differences in the signal intensities of the peak points and the signal intensities of the valley portion of the respective peaks.

Moreover, in the dialog box 655, it is possible to set the type of peak information to be registered (listed) in the peak list 614. In the dialog box 655, if "all spatial peaks" is selected, then the peak list control unit 203 extracts spatial peaks in the entire brain at each time/each frequency of the time-frequency plane, and registers the spatial peaks in the peak list 614. As illustrated by a peak portion 801 in FIG. 50, a spatial peak implies the peak of signal intensities of the biosignals in the entire brain at the time/frequency of interest. The signal intensities in the peak portion 801 are higher than the surrounding signal intensities.

In the dialog box 655, if "all time-frequency-based peaks" is selected, then the peak list control unit 203 extracts the time-frequency-based peak in the time-frequency plane at each position of the entire brain, and registers the extracted peaks in the peak list 614 illustrated by a peak portion 802 illustrated in FIG. 51, a time-frequency-based peak implies the peak of signal intensities of the biosignals in the time-frequency plane at the position of interest in the brain. The signal intensities in the peak portion 802 are higher than the surrounding signal intensities.

In the dialog box 655, if "spatial peak at specified time/frequency" is selected, then the peak list control unit 203 extracts the spatial peak in the entire brain at the specified time/frequency in the time/frequency plane, and registers the peak in the peak list 614. The specified time/frequency is not limited to one point, and sometimes a range is also selected.

In the dialog box 655, if "time-frequency-based peak at specified position" is selected, then the peak list control unit 203 extracts the time-frequency-based peak in the time-frequency plane at the specified position in the brain, and registers the peak in the peak list 614. However, the specified position is not limited to one point, and sometimes a range is also selected. For example, in the case of extracting the peak regarding the visual area, if the range of the entire occipital region of the head is specified, then it becomes easier to extract the desired peak.

Given below is the explanation of the operations performed in response to the selection of particular peak information from the peak list 614 in which sets of peak information are registered. When the analyst selects particular peak information (for example, "95%/9 ms/70 Hz/voxel: 1736" illustrated in FIG. 52) from the pull-down list 656 that is displayed from the peak list 614, the heat map display control unit 211 displays the heat map 611 corresponding to the particular position of the brain as indicated by the particular peak information. In that case, as explained earlier with reference to FIG. 14, the heat map display control unit 211 can concretely illustrate, in the heat map 611, the peak position indicated by the particular peak information.

The stereoscopic display control unit 212 displays, in the center of each row of the stereogram 612, the stereoscopic image of the brain corresponding to the time/frequency indicated by the selected peak information; and also displays the stereoscopic images of the brain that are present before and after in terms of time. In that case, the heat map that is superimposed on each stereoscopic image of the brain in the stereogram 612 can correspond to the signal intensities of the biosignals having the frequency indicated by the peak information.

The cross-section display control unit 213 displays, in the head region trihedral figure 613, the trihedral figure passing through the position of the brain indicated by the selected peak information. Meanwhile, as illustrated in FIG. 53, the cross-section display control unit 213 can display, in the stereoscopic image 644, a cut model image formed by cutting a portion in three-dimensional directions centering around the position of the brain indicated by the selected peak information.

As described above, by selecting particular peak information from among the sets of peak information registered in the peak list 614; it results in the display of the heat map 611, the stereogram 612, and the head region trihedral figure 613 corresponding to the selected peak information. As a result, it becomes possible to instantly recognize the position and the time/frequency of the selected peak. Besides, in the heat map 611, the state of the signal intensities at the concerned peak and the surrounding times/frequencies as well as the state of the signal intensities at the concerned peak position and the surrounding positions in the brain can also be understood.

<Regarding Reproduction Control Panel>

Figure 54:
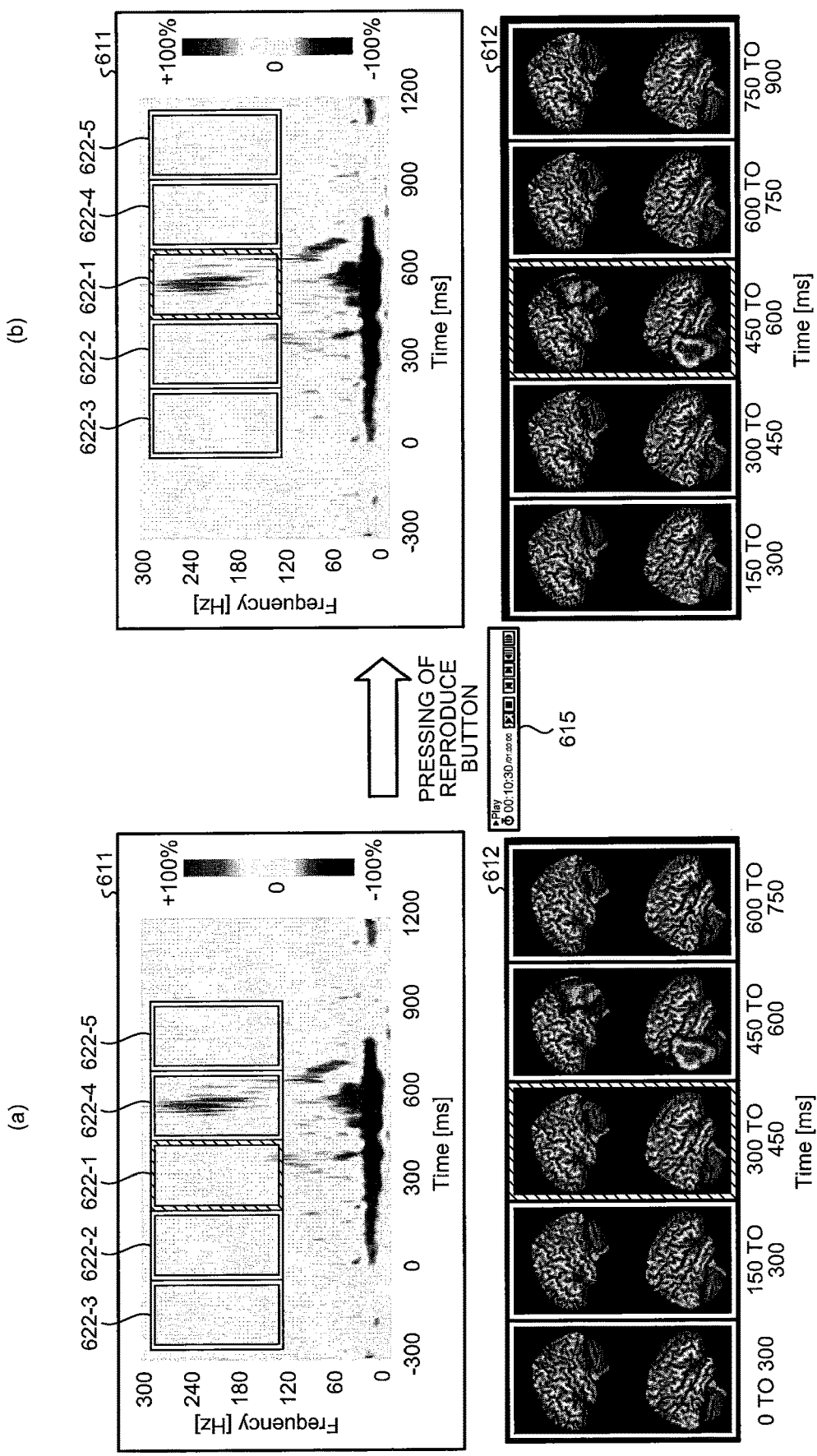
FIG. 54 is a diagram illustrating the state in which the heat map and the stereogram are reproduced in response to an operation of a reproduction control panel.
Figure 55:
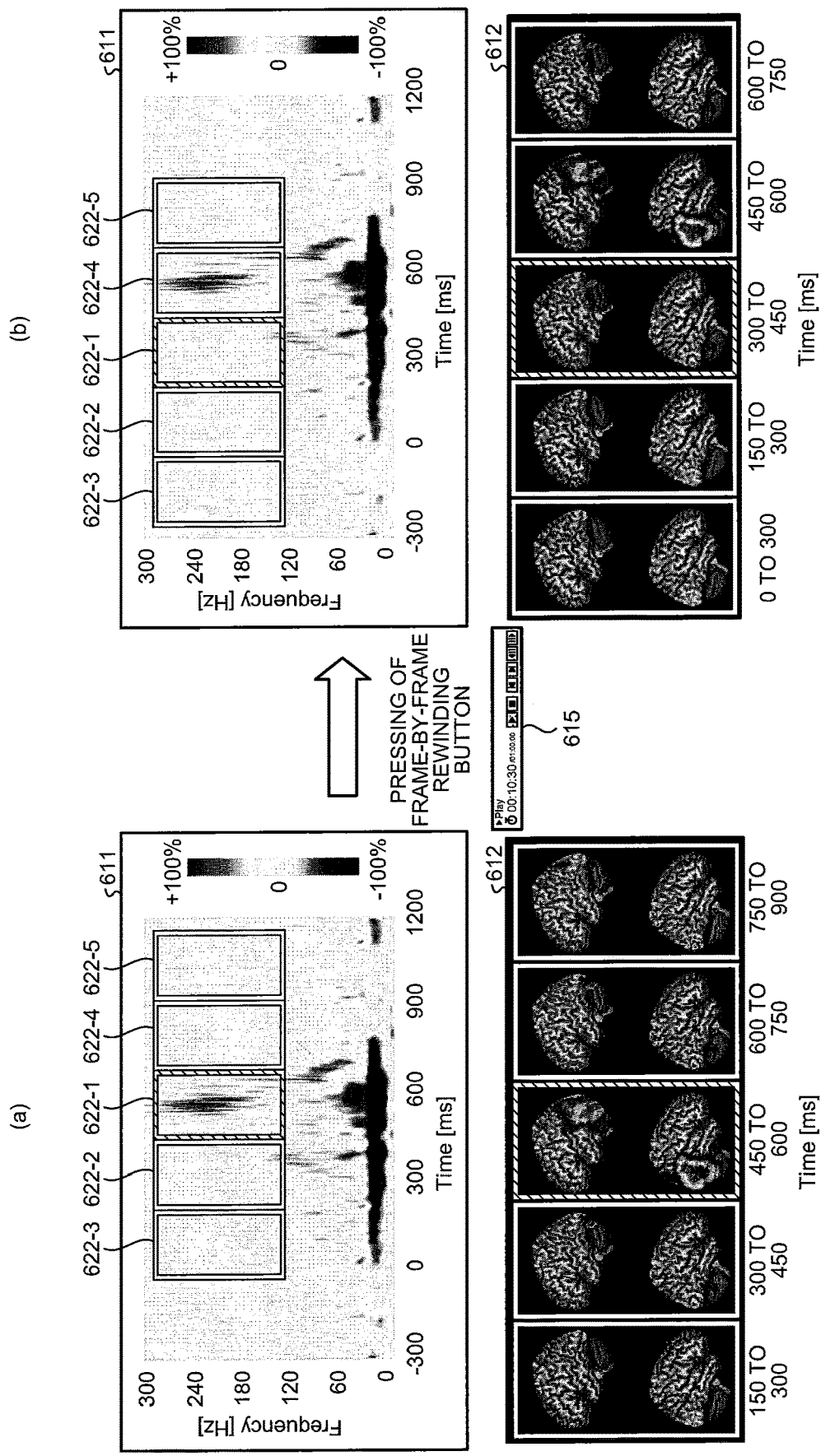
FIG. 55 is a diagram illustrating the state in which the heat map and the stereogram are rewound frame by frame in response to an operation of the reproduction control panel.
Figure 56:
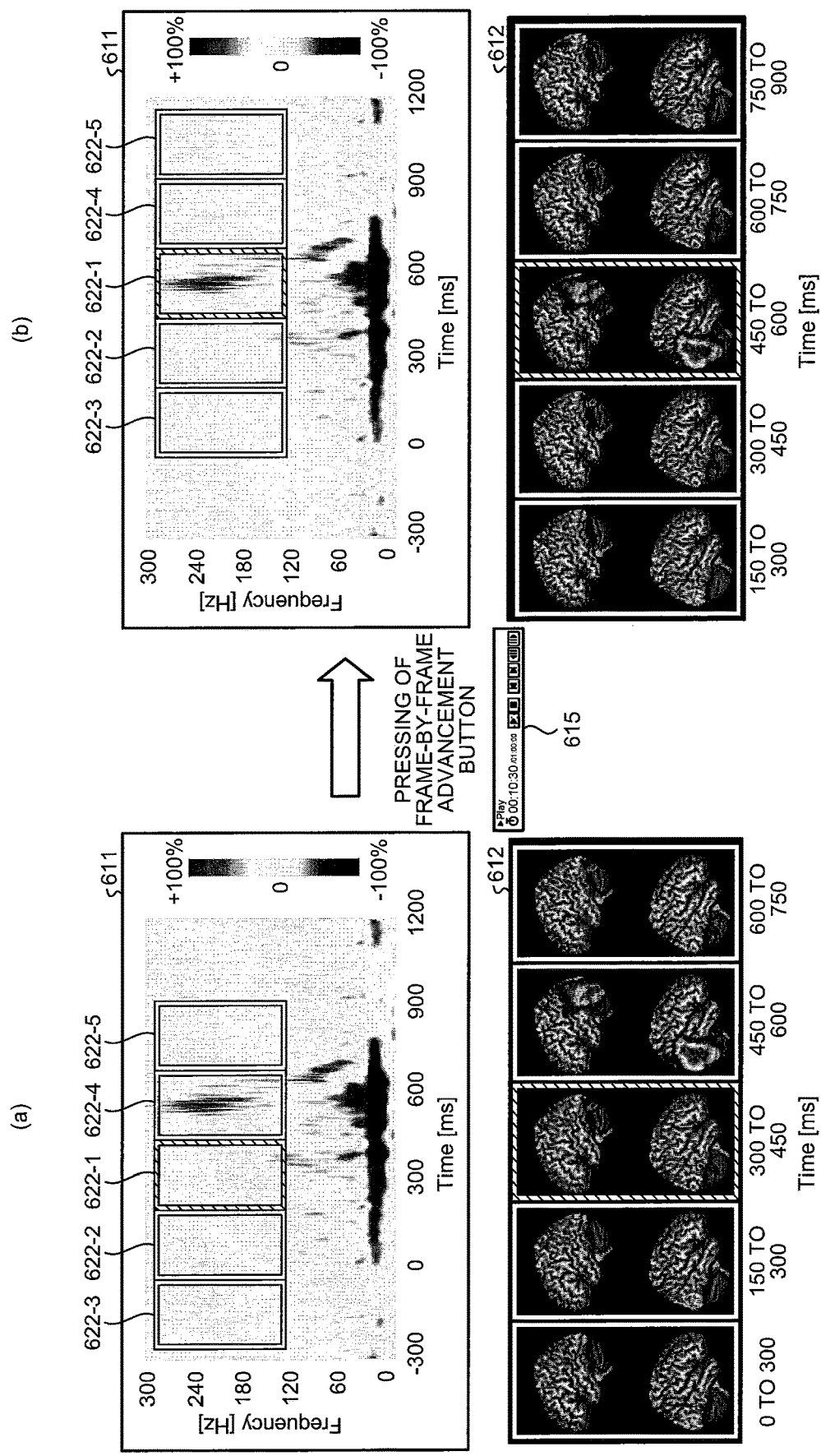
FIG. 56 is a diagram illustrating the state in which the heat map and the stereogram are advanced frame by frame in response to an operation of the reproduction control panel.

FIG. 54 is a diagram illustrating the state in which the heat map and the stereogram are reproduced in response to an operation of the reproduction control panel. FIG. 55 is a diagram illustrating the state in which the heat map and the stereogram are rewound frame by frame in response to an operation of the reproduction control panel. FIG. 56 is a diagram illustrating the state in which the heat map and the stereogram are advanced frame by frame in response to an operation of the reproduction control panel. Explained below with reference to FIGS. 53 to 55 are the operations performed when the reproduction control panel 615 of the time-frequency analysis screen 601 is operated.

The reproduction control panel 615 is a user interface that, in response to an operation thereof performed by the analyst reproduces, with time, the states of the heat map 611, the stereogram 612, and the head region trihedral figure 613.

For example, when a "reproduce" button on the reproduction control panel 615 is pressed, the reproduction display control unit 214 instructs the heat map display control unit 211 to move, with time, the specified area 622-1, which is specified in the heat map 611, and the surrounding corresponding areas 622-2 to 622-5 in the right-side direction (the direction of travel of time) as illustrated at (a) and (b) in FIG. 53. Moreover, accompanying the movement of the specified area 622-1 and the corresponding areas 622-2 to 622-5 in the heat map 611, the reproduction display control unit 214 instructs the stereoscopic display control unit 212 to switch to the display of the stereoscopic images of the brain corresponding to the areas as illustrated at (a) and (b) in FIG. 53. Furthermore, accompanying the movement of the specified area 622-1 in the heat map 611, the reproduction display control unit 214 instructs the cross-section display control unit 213 to display, in the trihedral figure and the stereoscopic image 644, the heat map of the signal intensities corresponding to the range of times/frequencies corresponding to the moving specified area 622-1.

When the analyst presses a "frame-by-frame rewinding" button, the reproduction display control unit 214 instructs the heat map display control unit 211 to move the specified area 622-1, which is specified in the heat map 611, and the surrounding corresponding areas 622-2 to 622-5 in the left-side direction (the direction of return of time) by a predetermined amount of time as illustrated at (a) and (b) in FIG. 54. Moreover, accompanying the movement of the specified area 622-1 and the corresponding areas 622-2 to 622-5 in the heat map 611, the reproduction display control unit 214 instructs the stereoscopic display control unit 212 to switch to the di of the stereoscopic images of the brain corresponding to the areas as illustrated at (a) and (b) in FIG. 54. Furthermore, accompanying the movement of the specified area 622-1 in the heat map 611, the reproduction display control unit 214 instructs the cross-section display control unit 213 to display, in the trihedral figure and the stereoscopic image 644, the heat map of the signal intensities corresponding to the range of times/frequencies corresponding to the post-movement specified area 622-1.

When the analyst presses "frame-by-frame advancement" button, the reproduction display control unit 214 instructs the heat map display control unit 211 to move the specified ea 622-1, which is specified in the heat map 611, and the surrounding corresponding areas 622-2 to 622-5 in the right-side direction (the direction of travel of time) by a predetermined amount of time as illustrated at (a) and (b) in FIG. 55. Moreover, accompanying the movement of the specified area 622-1 and the corresponding areas 622-2 to 622-5 in the heat map 611, the reproduction display control unit 214 instructs the stereoscopic display control unit 212 to switch to the display of the stereoscopic images of the brain corresponding to the areas illustrated at (a) and (b) in FIG. 55. Furthermore, accompanying the movement of the specified area 622-1 in the heat map 611, the reproduction display control unit 214 instructs the cross-section display control unit 213 to display, in the trihedral figure and the stereoscopic image 644, the heat map of the signal intensities corresponding to the range of times/frequencies of the post-movement specified area 622-1.

When the analyst presents a "stop" button on the reproduction control panel 615, the reproduction display control unit 214 instructs the heat map display control unit 211, the stereoscopic display control unit 212, and the cross-section display control unit 213 to stop the reproduction operation in the heat map 611, the stereogram 612, and the head region trihedral figure 613, respectively.

When the analyst presses a "move to beginning" button on the reproduction control panel 615, the reproduction display control unit 214 instructs the heat map display control unit 211 to move the specified area 622-1, which is specified in the heat map 611, to the beginning of the times. Moreover, accompanying the movement of the specified area 622-1 in the heat map 611, the reproduction display control unit 214 instructs the stereoscopic display control unit 212 to switch to the display of the stereoscopic image of the brain corresponding to the specified area 622-1. Furthermore, accompanying the movement of the specified area 622-1 in the heat map 611, the reproduction display control unit 214 instructs the cross-section display control unit 213 to display, in the trihedral figure and the stereoscopic image 644, the heat map of the signal intensities corresponding to the range of time/frequencies corresponding to the post-movement specified area 622-1.

When the analyst presses "move to end" button on the reproduction display panel 615, the reproduction display control unit 214 instructs the heat map display control unit 211 to move the specified area 622-1, which is specified in the heat map 611, to the end of the times. Moreover, accompanying the movement of the specified area 622-1 in the heat map 611, the reproduction display control unit 214 instructs the stereoscopic display control unit 212 to switch to the display of the stereoscopic image of the brain corresponding to the specified area 622-1. Furthermore, accompanying the movement of the specified area 622-1 in the heat map 611, the reproduction display control unit 214 instructs the cross-section display control unit 213 to display, in the trihedral figure and the stereoscopic image 644, the heat map of the signal intensities corresponding to the range of time/frequencies corresponding to the post-movement specified area 622-1.

As described above, as a result of such reproduction, the changes with time in the distribution (heat map) of the signal intensities displayed in the stereogram 612 and in the head region trihedral figure 613 can be checked in the form of a video, thereby enabling visual confirmation of the movement of the peaks with time.

<Regarding Initial Display>

Figure 57:
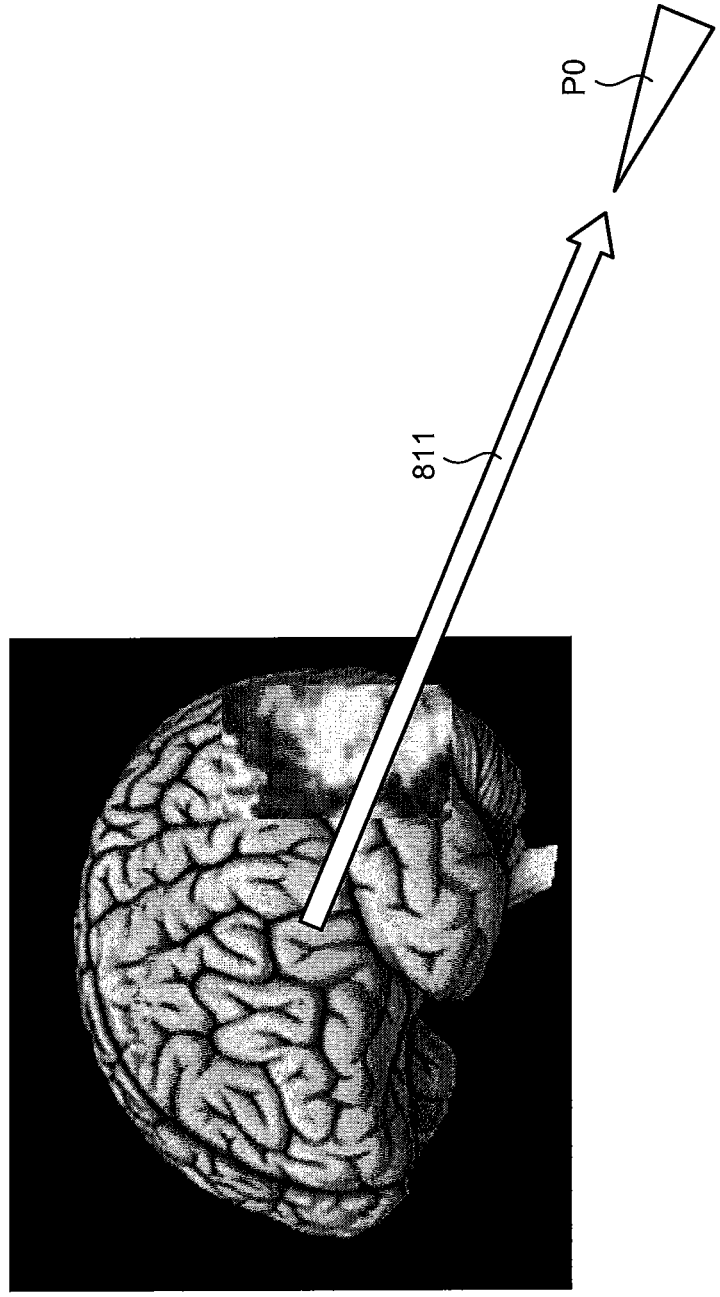
FIG. 57 is a diagram for explaining about deciding the viewpoint from which an image is to be initially displayed in regard to a peak.
Figure 58:
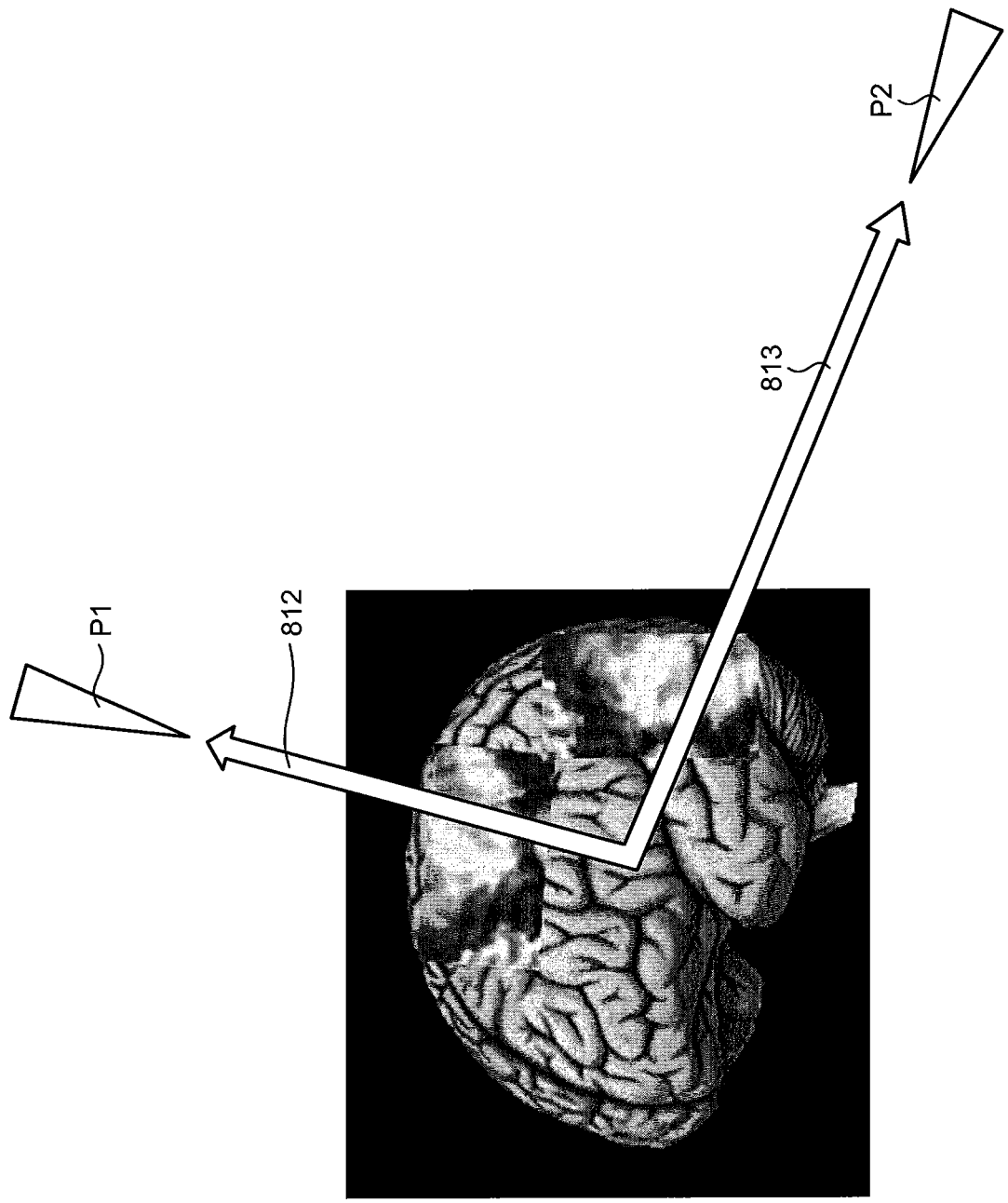
FIG. 58 is a diagram for explaining about deciding the viewpoint from which an image is to be initially displayed in regard to two peaks.
Figure 59:
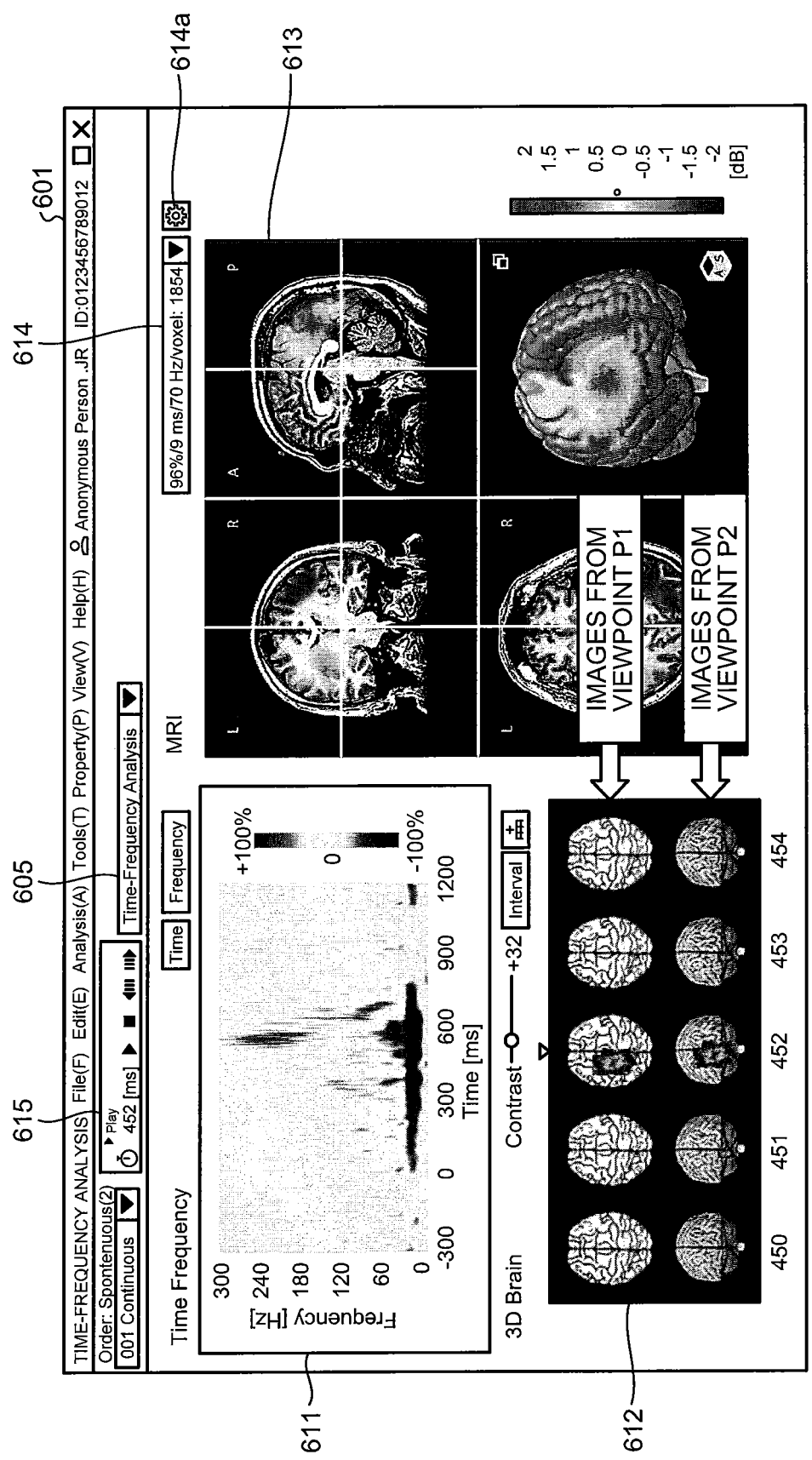
FIG. 59 is a diagram illustrating the state in which an image from the viewpoint illustrated in FIG. 58 is initially displayed in the stereogram.

FIG. 57 is a diagram for explaining about deciding the viewpoint from which an image is to be initially displayed in regard to a peak. FIG. 58 is a diagram for explaining about deciding the viewpoint from which an image is to be initially displayed in regard to two peaks. FIG. 59 is a diagram illustrating the state in which an image from the viewpoint illustrated in FIG. 58 is initially displayed in the stereogram. Explained below with reference to FIGS. 56 to 58 is the initial display of the heat map 611, the stereogram 612, and the head region trihedral FIG. 613 in response to the activation (opening) of the time-frequency analysis screen 601.

The following explanation is given about the image displayed as the initial display of the heat map 611, the stereogram 612, and the head region trihedral figure 613 when the analyst activates (opens) the time-frequency analysis screen 601.

For example, the analysis display control unit 202 obtains, from the overall times/frequencies, the time/frequency and the in-brain position at which the signal intensity is the highest across the entire brain. In that case, the heat map display control unit 211 displays the heat map 611 corresponding to the position in the brain as obtained by the analysis display control unit 202. The stereoscopic display control unit 212 displays, in the stereogram 612, the stereoscopic image of the brain corresponding to the time/frequency of the highest signal intensity as obtained by the analysis display control unit 202. The cross-section display control unit 213 displays, in the head region trihedral figure 613, a trihedral figure that passes through the in-brain position obtained by the analysis display control unit 202; and superimposes, on the trihedral figure and the stereoscopic image 644, the heat map corresponding to the time/frequency of the highest signal intensity as obtained by the analysis display control unit 202.

Meanwhile, the analysis display control unit 202 can obtain the in-brain position at which the average of the signal intensities across all times/frequencies is the highest. In that case, the heat map display control unit 211 displays the heat map 611 corresponding to the in-brain position obtained by the analysis display control unit 202. The stereoscopic display control unit 212 displays, in the stereogram 612, the stereoscopic image of the brain corresponding to the time/frequency at which the signal intensity is the highest in the displayed heat map 611. The cross-section display control unit 213 displays, in the head region trihedral figure 613, a trihedral figure that passes through the in-brain position obtained by the analysis display control unit 202; and superimposes, on the trihedral figure and the stereoscopic image 644, the heat map corresponding to the time/frequency at which the signal intensity is the highest in the displayed heat map 611.

Alternatively, the analysis display control unit 202 can obtain the time/frequency at which the average value of the signal intensities across the entire brain the highest. In that case, the stereoscopic display control unit 212 displays in the stereogram 612, the stereoscopic image of the brain corresponding to the time/frequency obtained by the analysis display control unit 202. The heat map display control unit 211 obtains the in-brain position having the highest signal intensity in the heat map that is displayed on the stereoscopic images in the stereogram 612 and that corresponds to the time/frequency obtained by the analysis display control unit 202; and displays the heat map 611 corresponding to the concerned in-brain position. The cross-section display control unit 213 displays, in the head region trihedral FIG. 613, a trihedral figure passing through the in-brain position obtained by the heat map display control unit 211; and superimposes, on the trihedral figure and the stereoscopic image 644, the heat map corresponding to the time/frequency obtained by the analysis display control unit 202.

Alternatively, the stereoscopic display control unit 212 can display the heat map 611 corresponding to the in-brain position indicating the initial set of peak information from among the sets of peak information registered in the peak list 614. Moreover, the stereoscopic display control unit 212 displays, in the stereogram 612, the stereoscopic image of the brain corresponding to the time/frequency indicated by the initial set of peak information. The cross-section display control unit 213 displays, in the head region trihedral figure 613, a trihedral figure passing through the in-brain position indicated by the initial set of peak information from among the sets of peak information registered in the peak list 614; and superimposes, on the trihedral figure and the stereoscopic image 644, the heat map corresponding to the time/frequency indicated by the initial set of peak information.

Alternatively, the stereoscopic display control unit 212 can display the heat map 611 corresponding to the in-brain position that is set in advance according to the measurement target (the visual area, the auditory area, the somatosensory area, the motor area, or the speech area). The cross-section display control unit 213 displays, in the head region trihedral figure 613, a trihedral figure passing through the in-brain position set in advance according to the measurement target (the visual area, the auditory area, the somatosensory area, the motor area, or the speech area); and superimposes, on the trihedral figure and the stereoscopic image 644, the heat map corresponding to the time/frequency indicated by the peak information.

Given below is the explanation about the initial viewpoint for the display of the stereoscopic images in the stereogram 612 and the display of the stereoscopic image 644 in the head region trihedral figure 613 when the analyst activates (opens) the time-frequency analysis screen 601.

For example, the viewpoint set in advance according to the measurement target (the visual area, the auditory area, the somatosensory area, the motor area, or the speech area) can be used as the initial viewpoint. In that case, regarding the stereogram 612, the number of rows (viewpoints) can also be set in advance. If the stereogram 612 has two rows, two viewpoints need to be set in advance. For example, if the speech area represents the measurement target, the viewpoints from the left lateral and the right lateral of the brain are set in advance.

Alternatively, the viewpoint in which the initially-registered peak in the peak list 614 is most clearly visible can be used as the initial viewpoint. More particularly, as illustrated in FIG. 57, a viewpoint PO can be set as the initial viewpoint on a straight line 811 joining the center of the brain and the peak.

Alternatively, the viewpoint that is set using such a peak in the peak list 614 at which a predetermined parameter (for example, the value (the signal intensity) or the height of the peak illustrated in FIG. 50) exceeds a predetermined threshold value can used as the initial viewpoint. For example, when there are two peaks that exceed the threshold value, the stereogram 612 is displayed to have two rows and, as illustrated in FIG. 58, viewpoints P1 and P2 can be set as initial viewpoints on straight lines 812 and 813, respectively, that join the center of the brain and the respective peaks. In that case, in FIG. 59 is illustrated an example in which the stereoscopic images of the brain from the viewpoint P1 are displayed in the upper row of the stereogram 612 and the stereoscopic images of the brain from the viewpoint P2 are displayed in the lower row of the stereogram 612.

As described above, the heat map 611 is displayed that is related to the times/frequencies of the signal intensities at a particular position or in a particular range in the brain; and, centering around the stereoscopic image on which a heat map indicating the activity of the brain corresponding to the point or the range specified in the heat map 611 is superimposed, stereoscopic images indicating the activity of the brain before and after in terms of time are displayed, that is, still images (herein, stereoscopic images) indicating the activity of the brain are displayed in a frame-by-frame advancing manner or a frame-by-frame rewinding manner. As a result, still images indicating the activity of the brain can be extracted in an appropriate and prompt manner, thereby making it easier to analyze the activity of the bran. Moreover, it becomes easier to use such information as the basis of discussion during a conference.

From the sets of peak information registered in the peak list 614, when particular peak information is selected; it results in the display of the heat map 611, the stereogram 612, and the head region trihedral figure 613 corresponding to the selected peak information. As a result, it becomes possible to instantly recognize the in-brain position and the time/frequency of the selected peak. Besides, in the heat map 611, the state of the signal intensities at the concerned peak and the surrounding times/frequencies as well as the state of the signal intensities at the concerned peak position and the surrounding positions in the brain can also be understood.

Moreover, the viewpoint of the brain can be freely changed in the stereogram 612, and the same change can be reflected in the brain images present in the same row or in different rows. As a result, by changing the viewpoint of only a particular stereoscopic image (the target stereoscopic image), the same change is reflected in the other stereoscopic images. That leads to an enhancement in the operability and, as a result of comparing a plurality of rows, it becomes easier to check the changes in the activity of the brain from the counterpart viewpoint before and after in terms of time. Moreover, the viewpoint of the brain drawn in the stereoscopic images is freely changed so as to enable checking of the fire position not visible in particular viewpoints.

Furthermore, a change in the viewpoint implemented with respect to the stereoscopic image 644 in the head region trihedral figure 613 can be reflected, according to various settings, in the viewpoints of the stereographic images of the brain that are arranged in chronological order in the stereogram 612. As a result, the same change in the viewpoint as the change implemented with respect to the stereoscopic image 644 need not be again performed with respect to the stereogram 612. That leads to an enhancement in the operability, and the changes in the state of the brain in the stereogram 612 can be checked in chronological order from either the identical viewpoint or the counterpart viewpoint to the changed viewpoint in the stereoscopic image 644.

Figure 60:
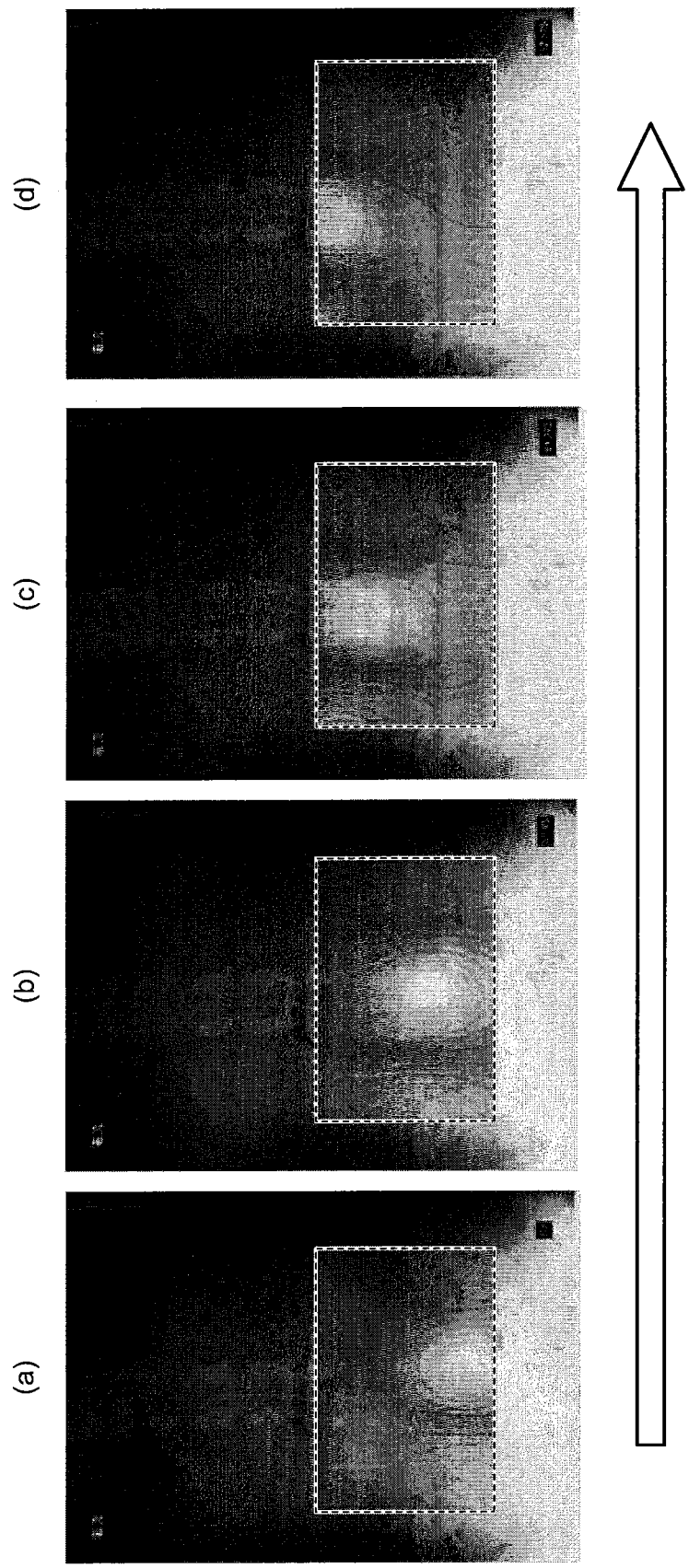
FIG. 60 is a diagram illustrating a state in which a signal of lumbar vertebra is transmitted upward in a time series.

Meanwhile, the embodiment described above deals with the biosignals regarding the brain that represents the biological site. However, that is not the only possible case. Alternatively, for example, the embodiment can be implemented for the biosignals from other biological sites such as the spinal cord or the muscles. For example, the stereogram 612 described with the drawing of the brain can be displayed as in FIG. 60. FIG. 60 illustrates a state in which a signal of lumbar vertebra is transmitted upward in an order of (a) to (d) in FIG. 60.

In the embodiment described above, at least one of the functional units of the biosignal measurement system 1 is implemented by executing a computer program, that computer program is stored in advance in a read only memory (ROM). Alternatively, the computer program executed in the biosignal measurement system 1 according to the embodiment can recorded as an installable file or an executable file in a computer-readable recording medium such as a compact disk read only memory (CD-ROM), a flexible disk (FD), a compact disk recordable (CD-R), or a digital versatile disc (DVD). Still alternatively, the computer program executed in the biosignal measurement system 1 according to the embodiment can be stored in a downloadable manner in a computer connected to a network such as the Internet. Still alternatively, the computer program executed in the biosignal measurement system 1 according to the embodiment can be distributed via a network such as the Internet. Meanwhile, the computer program executed in the biosignal measurement system 1 according to the embodiment contains a module of at least one of the functional units. As far as the actual hardware is concerned, a CPU reads the computer program from a ROM and executes it, so that the functional units are loaded and generated in a main memory device.

According to an embodiment, still images indicating the activity of the brain are displayed in a frame-by-frame advancing manner or a frame-by-frame rewinding manner, thereby making it easier to analyze the activity of the brain.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. An information processing device comprising:
   a first display control unit configured to display, in a display device, a first intensity distribution which is at least per unit time and which is regarding a biosignal coming from a particular source; and
   a second display control unit configured to display, side-by-side in the display device,
      first image which has a shape of the source and on which a second intensity distribution of the biosignal corresponding to time corresponding to a point or an area specified in the first intensity distribution is superimposed, and
      second images which have the shape of the source and on which second intensity distributions of the biosignal before and after the time are superimposed.

2. The information processing device according to claim 1, wherein the second display control unit is configured to display, when a plurality of points or a plurality of areas is specified in the first intensity distribution, side-by-side in the display device,
   the first image corresponding to the biosignal corresponding to time corresponding to each of the plurality of points or each of the plurality of areas, and
   the second images corresponding to the biosignal before and after the time.

3. The information processing device according to claim 1, wherein the second display control unit is configured to change a display form of at least one of the first image and the second image, according to an operation input performed from an input device.

4. The information processing device according to claim 3, wherein the second display control unit is configured to
   display shape images, in which the first image and the second images form a set, in the same display form, and
   display a third image having a different display form than the display form of the shape images.

5. The information processing device according to claim 4, wherein the second display control unit is configured to, when a change of a display form of any one image included in the shape images is made according to an operation input performed from the input device, change, based on the change, a display form of at least any one image included in other images included in the shape images and the third image that is different than the shape images.

6. The information processing device according to claim 3, wherein the second display control unit is configured to, according to an operation input performed from the input device, change at least any one of a viewpoint with respect to the shape of the source, size of the shape of the source, brightness of the source, and transparency of the source as the display form of at least either the first image or the second image.

7. The information processing device according to claim 1, further comprising a third display control unit configured to display in the display device, a cross-section image of the source on which a third intensity distribution of the biosignal corresponding to time corresponding to a point or an area specified in the first intensity distribution is superimposed.

8. The information processing device according to claim 7, wherein the third display control unit configured to display, in the display device, a stereoscopic image of the source on which a fourth intensity distribution of the biosignal corresponding to time corresponding to a point or an area specified in the first intensity distribution is superimposed.

9. The information processing device according to claim 7, wherein the first display control unit is configured to display the first intensity distribution of the biosignal at a position in the source, the position being identified by a point or an area specified in the cross-section image displayed by the third display control unit.

10. The information processing device according to claim 8, wherein the second display control unit is configured to, when a change of a display form of the stereoscopic image is made according to an operation input performed from an input device, change, based on the change, the display form of the first image and the display form of the second image.

11. The information processing device according to claim 8, wherein the second display control unit is configured to, when a display form of the stereoscopic image is changed according to an operation input performed from an input device, display, apart from the first image and the second image that are already displayed, a new first image and a new second image having the same display form as the changed display form of the stereoscopic image.

12. The information processing device according to claim 8, wherein the third display control unit configured to display the stereoscopic image that is formed by cutting a portion in three-dimensional directions with a position in the source as a center, the position being identified in the cross-section image.

13. The information processing device according to claim 1, wherein the first display control unit is configured to display the first intensity distribution that is broken down into time and a frequency regarding the biosignal.

14. The information processing device according to claim 13, further comprising a peak control unit configured to extract at least one peak from the biosignal according to a standard based on time, a frequency, and a position in the source, wherein
the first display control unit is configured to display the first intensity distribution of the biosignal at a position in the source, the position being indicated by a peak selected from the at least one peak extracted by the peak selecting unit according to an operation input performed from an input device, and
the second display control unit is configured to display the first image and the second image corresponding to time and a frequency indicated by the selected peak.

15. The information processing device according to claim 8, wherein
the first display control unit is configured to display the first intensity distribution that is broken down into time and a frequency regarding the biosignal,
the information processing device further comprises a peak control unit configured to extract at least one peak from the biosignal according to a standard based on time, a frequency, and a position in the source, and
the third display control unit is configured to, according to an operation input performed from an input device,
display the cross-section image corresponding to a position in the source, the position being indicated by a peak selected from the at least one peak extracted by the peak control unit, and
display the stereoscopic image on which the fourth intensity distribution of the biosignal corresponding to time and a frequency indicated by the selected peak is superimposed.

16. The information processing device according to claim 15, wherein the third display control unit is configured to display toe selected peak in a superimposed manner on the stereoscopic image.

17. The information processing device according to claim 1, further comprising a calculating unit configured to calculate the biosignal in the source from a measured signal.

18. The information processing device according to claim 1, wherein the source is a biological site.

19. An information processing method comprising:
first displaying, in a display device, a first intensity distribution which is at least per unit time and which is regarding a biosignal coming from a particular source; and
second displaying, side-by-side in the display device,
a first image which has a shape of the source and on which a second intensity distribution of the biosignal corresponding to time corresponding to a point or an area specified in the first intensity distribution is superimposed, and
second images which have the shape of the source and on which second intensity distributions of the biosignal before and after the time are superimposed.

20. A computer program product comprising a non-transitory computer-readable medium containing an information processing program, the program causing a computer to perform:
first displaying, in a display device, a first intensity distribution which is at least per unit time and which is regarding a biosignal coming from a particular source; and
second displaying, side-by-side in the display device,
image which has a shape of the source and on which a second intensity distribution of the biosignal corresponding to time corresponding to a point or an area specified in the first intensity distribution is superimposed, and
second images which have the shape of the source and on which second intensity distributions of the biosignal before and after the time are superimposed.

21. A biosignal measurement system comprising:
a measurement device configured to measure, as the biosignal, biosignals of one or more types from a subject being tested; and
the information processing device according to claim 1.

* * * * *